(12) United States Patent
Chan et al.

(10) Patent No.: US 8,193,377 B2
(45) Date of Patent: *Jun. 5, 2012

(54) (−)-EPIGALLOCATECHIN GALLATE DERIVATIVES FOR INHIBITING PROTEASOME

(75) Inventors: Tak-Hang Chan, Hung Hom (HK); Wai-Har Lam, Hung Hom (HK); Larry Ming-Cheung Chow, Hung Hom (HK); Qing Ping Dou, Detroit, MI (US); Deborah Joyce Kuhn, Detroit, MI (US); Aslamuzzaman Kazi, Tampa, FL (US); Sheng Biao Wan, Hung Hom (HK); Kristin R. Landis-Piwowar, Detroit, MI (US)

(73) Assignees: The Hong Kong Polytechnic University, Hung Hom, Kowloon (HK); Wayne State University, Detroit, MI (US); University of South Florida, Tampa, FL (US)

(*) Notice: Subject to any disclaimer, the term of this patent is extended or adjusted under 35 U.S.C. 154(b) by 829 days.

This patent is subject to a terminal disclaimer.

(21) Appl. No.: 11/660,513

(22) PCT Filed: Aug. 15, 2005

(86) PCT No.: PCT/CN2005/001262
§ 371 (c)(1),
(2), (4) Date: Nov. 13, 2007

(87) PCT Pub. No.: WO2006/017981
PCT Pub. Date: Feb. 23, 2006

(65) Prior Publication Data
US 2008/0176931 A1 Jul. 24, 2008

Related U.S. Application Data

(62) Division of application No. 10/921,332, filed on Aug. 19, 2004, now Pat. No. 7,544,816.

(60) Provisional application No. 60/649,569, filed on Feb. 4, 2005.

(51) Int. Cl.
*C07D 311/00* (2006.01)
*A01N 43/16* (2006.01)

(52) U.S. Cl. .................. 549/399; 514/456
(58) Field of Classification Search .............. 549/399; 514/456
See application file for complete search history.

(56) References Cited

U.S. PATENT DOCUMENTS
7,544,816 B2 * 6/2009 Chan et al. ........... 549/399
2006/0041010 A1 2/2006 Chan et al.

FOREIGN PATENT DOCUMENTS
JP 10-254087 A 9/1998
WO WO 99/22728 A1 5/1999
WO WO 2006/017981 A1 2/2006

OTHER PUBLICATIONS

Weinges et al. STN Accession No. 1968:459534, Document No. 69:59534, Abstract of Justus Liebigs Annalen der Chemie (1968).*
Danne et al. Phytochemistry (1994), 37(2), 533-8.*
JP 57118580 (Kanebo Ltd). STN Accession No. 1983:53519, Document No. 98:53519, Abstract of JP 57118580 (Kanebo Ltd).*
Okushio et al., "Methylation of Tea Catechins by Rat Liver Homogenates," Biosci. Biotechnol. 1999, 63 (2), pp. 430-432.
Kohri et al., "Metabolic Fate of (−)-[4-$^3$H] Epigallocatechin Gallate in Rats after Oral Administration," J. Agric. Food Chem., 2001, vol. 49, No. 8, pp. 4102-4112, American Chemical Society.
Li et al., "Analysis of Urinary Metabolites of Tea Catechins by Liquid Chromatography/Electrospray Ionization Mass Spectrometry," Chem. Res. Toxicol., 2001, 14, pp. 702-707, American Chemical Society.
Kohri et al., Identification of Metabolite of (−)-Epicatechin Gallate and Their Metabolic Fate in the Rat, J. Agric. Food Chem., 2003, vol. 51, No. 18, pp. 5561-5566, American Chemical Society.

(Continued)

*Primary Examiner* — Nizal Chandrakumar
(74) *Attorney, Agent, or Firm* — Buchanan Ingersoll & Rooney PC

(57) ABSTRACT

(−)-EGCG, the most abundant catechin, was found to be chemopreventive and anticancer agent. However, (−)-EGCG has at least one limitation: it gives poor bioavailability. This invention provides compounds of generally formulae below, wherein $R_{11}$, $R_{12}$, $R_{13}$, $R_{21}$, $R_{22}$, $R_2$, $R_3$, and $R_4$ are each independently selected from the group consisting of —H, and $C_1$ to $C_{10}$ acyloxyl group; and $R_5$ is selected from the group consisting of —H, $C_1$-$C_{10}$-alkyl, $C_2$-$C_{10}$-alkenyl, $C_2$-$C_{10}$-alkynyl, $C_3$-$C_7$-cycloalkyl, phenyl, benzyl and $C_3$-$C_7$-cycloalkenyl, whereas each of the last mentioned 7 groups can be substituted with any combination of one to six halogen atoms; at least one of $R_{11}$, $R_{12}$, $R_{13}$, $R_{21}$, $R_{22}$, $R_2$, $R_3$ and $R_4$ is —H, which were found to be more potent than their non-protected counterparts, which can be used as proteasome inhibitors to reduce tumor cell growth.

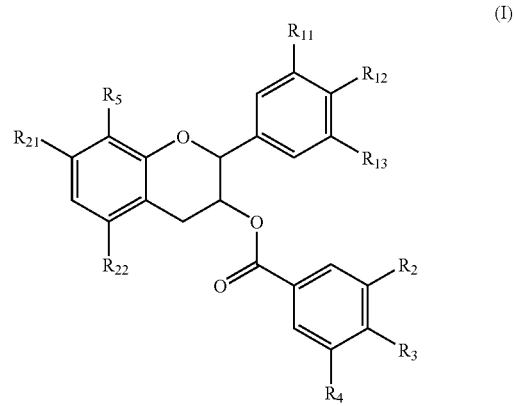

(I)

10 Claims, 21 Drawing Sheets

OTHER PUBLICATIONS

Lu et al., Enzymology of Methylation of Tea Catechins and Inhibition of Catechol-o-methyltransferase by (−)-Epigallocatechin Gallate, Drug Metabolism and Disposition, 2003, vol. 31, No. 5, pp. 572-579, American Society for Pharmacology and Experimental Therapeutics.

Meng, et al., "Identification and Characterization of Methylated and Ring-Fission Metabolites of Tea Catechins Formed in Humans, Mice, and Rats," Chem. Res. Toxicol., 2002, vol. 15, No. 8, pp. 1042-1050, American Chemical Society.

Wu et al., "Tea Intake, COMT Genotype, and Breast Cancer in Asian-American Women," Cancer Research, Nov. 1, 2003, 63, pp. 7526-7529, American Association for Cancer Research.

Landis-Piwowar et al., "Methylation Suppresses the Proteasome-Inhibitory Function of Green Tea Polyphenols," Journal of Cellular Physiology, 2007, 213(1), pp. 252-260, Wiley-Liss, Inc.

Kuhn et al., "Synthetic Peracetate Tea Polyphenols as Potent Proteasome Inhibitors and Apoptosis Inducers in Human Cancer Cells," Frontiers in Bioscience 10, May 1, 2005, pp. 1010-1023.

International Preliminary Report of Patentability, International Application No. PCT/CN2005/001262 (Forms PCT/IPEA/416 and 409) dated Mar. 8, 2006.

International Search Report, International Application No. PCT/CN2005/001262 Dated Dec. 1, 2005.

Andreas, D. et al., "Flavan-3-ols, prodelphinidins and further polyphenols from *Cistus salvifolius*", CA 122:5467 (1995).

Smith et al., *Molecular Medicine*, "Synthetic Analogs of Green Tea Polyphenols as Proteasome Inhibitors", vol. 8, No. 7 (2002), pp. 382-392.

Kuhn et al., *Frontiers in Bioscience 10*, "Synthetic Peracetate Tea polyphenols as Potent Proteasome Inhibitirs and Apoptosis Inducers in Human Cancer Cells", (May 1, 2005), pp. 1010-1023.

Kohri et al., *J.Agric. Food Chem.*, "Synthesis of (−)-[4-$^3$H]Epigallocatechin Gallate and its Metabolic Fate in Rates after Intravenous Administration", vol. 49, No. 2 (2001), pp. 1042-1048.

Hiipakka et al., *Biochemical Pharmacology*, "Structure-activity relationships for inhibition of human 5α-reductases by polyphenols", vol. 63 (2002), pp. 1165-1176.

Kreimeyer et al., "Separations of flavan-3-ols and dimeric proanthocyanidins by capillary electrophoresis", CA 128:221701 (1998).

Smith et al., *Proteins: Structure Function and Bioinformatics*, "Docking Studies and Model Development of Tea Polyphenol Proteasome Inhibitors: Applications to Rational Drug Design", 54:58-70 (2004).

Nam et al., *The Journal of Biological Chemistry*, "Ester Bond-containing Tea Polyphenols Potently Inhibit Proteasome Activity in Vitro and in Vivo", vol. 276, No. 16 (2001), pp. 13322-13330.

Kazi et al., "Potential molecular targets of tea polyphenols in human tumor cells: significance in cancer proliferation", PMID:12494882 (2002).

Danne et al., *Phytochemistry*, "Flavan-3-ols, Prodelphinidins and Further Polyphenols from *Cistus salvifolius*," vol. 37, No. 2 (1994), pp. 533-538.

U.S. Appl. No. 10/921,332, filed Feb. 23, 2006, Chan et al.

Wang et al., *Natural Product Research and Development*, "The synthesis of liposoluble tea polyphenols (LTP) and its resistance to autoxidation of oil," vol. 13, No. 4 (2001), pp. 12-15 (with abstract).

Wang et al., *Fine Chemicals*, "Synthesis of liposoluble tea polyphenols with varying aliphatic groups and their antioxidation activity," vol. 19, No. 2 (2002), pp. 86-89 (with abstract).

De Groot et al., Bulletin of Magnetic Resonance, "Advantages of Long-Range-INEPT Measurements for Structure Determination of Catechin Esters," vol. 17, No. 1-4 (1995), pp. 242-243.

Lam et al., *Bioorganic & Medicinal Chemistry*, "A potential prodrug for a green tea polyphenol proteasome inhibitor: evaluation of the peracetate ester of (−)-epigallocatechin gallate [(−)-EGCG]," vol. 12, No. 21 (2004), pp. 5587-5593.

Jung et al. *International Journal of Experimental Pathology*, "Inhibition of Tumor Invasion and Angiogenesis by Epigalocatechin Gallage (EGCG), A Major Component of Green Tea", vol. 52 (2001), pp. 309-316.

* cited by examiner

DMSO (-)EGCG 1

A.

B.

C.

D.

A.

B.

C.

D.

(−)-EPIGALLOCATECHIN GALLATE DERIVATIVES FOR INHIBITING PROTEASOME

FIELD OF THE INVENTION

This invention relates to derivates of (−)-epigallocatechin gallate, particularly for use as proteasome inhibitors and/or for inhibition of cancer cell growth.

BACKGROUND OF THE INVENTION

The polyphenols found in green tea extracts are (−)-epicatechin (EC), (−)-epigallocatechin (EGC), (−)-epicatechin-3-gallate (ECG) and (−)-epigallocatechin-3-gallate (EGCG). In particular, (−)-EGCG, the most abundant catechin, was found to be chemopreventive and anticancer agent among the green tea catechins (GTCs) (4. Fujiki, H. *J Cancer Res Clin Oncol.* 999, 125, 589-97).

Proteasome is a large protein complex with multicatalytic activities that are responsible for the degradation of not only obsolete and misfolded proteins, but also regulatory proteins involved in cell cycle and apoptosis. In proteasome-dependent proteolysis, ubiquitin is first conjugated to the substrate, followed by degradation of the substrate and recycling of the amino acids and ubiquitin. The ubiquitin/proteasome-dependent degradation pathway plays an essential role in up-regulation of cell proliferation, down-regulation of cell death, and development of drug resistance in human tumor cells. Therefore, proteasome inhibitors show great potential as novel anticancer drugs (Dou, Q. P.; Li, B. *Drug Resist Update* 1999, 2, 215-23). It has been shown that natural (−)-EGCG and synthetically derived (+)-EGCG are potent inhibitors of the proteasomal chymotrypsin activity, leading to growth arrest and/or apoptosis (Smith, D. M.; Wang, Z.; Kazi, A.; Li, L.; Chan, T. H.; Dou, Q. P. *Mol Med* 2002, 8: 382-92.). US patent publication no. 20040110790 (Zaveri et al.) describes synthetic analogs of green tea polyphenols as chemotherapeutic and chemopreventive agents, but the synthesis provided only racemic compounds, and do not use natural occurring catechins derived from green tea.

The P13K/Akt signaling is a widely known tumor cell survival pathway (Vanhaesebroeck, B.; Alessi, D. R. *Biochem J* 2000, 346, 561-76). Blocking this pathway is considered as an important mechanism for inhibiting tumor growth. Phosphorylated Akt (p-Akt) is the activated form of Akt. Once Akt is activated, it can mediate cell cycle progression by phosphorylation and consequent inhibition of the cyclindependent kinase inhibitor p 27.24 Recently, (−)-EGCG has been found to inhibit the Akt kinase activity via reducing the phosphatidylinositol 3-kinase signals in MMTV-Her-2/neu mouse mammary tumor NF639 cells, leading to reduced tumor cell growth (Pianetti, S.; Guo, S.; Kavanagh, K. T.; Sonenshein, G. E. *Cancer Res* 2002, 62, 652-5).

However, (−)-EGCG has at least one limitation: it gives poor bioavailability. A study by Nakagawa et al. showed that only 0.012% of (−)-EGCG could be absorbed in rats given 56 mg of (−)-EGCG orally (Nakagawa, K.; Miyazawa, T. *Anal Biochem.* 1997, 248, 41-9). This low absorption was thought to be due to the poor stability of (−)-EGCG in neutral or alkaline solutions. As pH value of the intestine and body fluid is neutral or slightly alkaline, GTCs will be unstable inside the human body, thus leading to reduced bioavailability.

OBJECTS OF THE INVENTION

Therefore, it is an object of this invention to provide a (−)-EGCG derivative that is able to resolve at least one or more of the problems as set forth in the prior art. As a minimum, it is an object of this invention to provide the public with a useful choice.

SUMMARY OF THE INVENTION

Accordingly, this invention provides a compound for inhibiting proteasome having the formula:

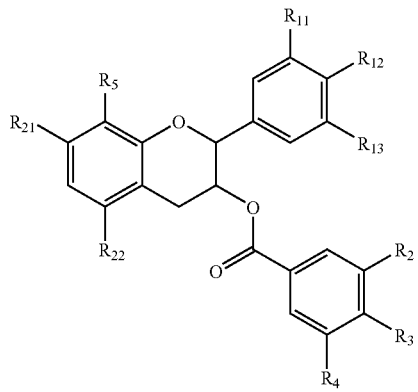

wherein $R_{11}$, $R_{12}$, $R_{13}$, $R_{21}$, $R_{22}$, $R_2$, $R_3$, and $R_4$ are each independently selected from the group consisting of —H, and $C_1$ to $C_{10}$ acyloxyl group; and $R_5$ is selected from the group consisting of —H, $C_1$-$C_{10}$-alkyl, $C_2$-$C_{10}$-alkenyl, $C_2$-$C_{10}$-alkynyl, $C_3$-$C_7$-cycloalkyl, phenyl, benzyl and $C_3$-$C_7$-cycloalkenyl, whereas each of the last mentioned 7 groups can be substituted with any combination of one to six halogen atoms;

at least one of $R_{11}$, $R_{12}$, $R_{13}$, $R_{21}$, $R_{22}$, $R_2$, $R_3$, and $R_4$ is $C_1$ to $C_{10}$ acyloxyl group; and at least one of $R_{11}$, $R_{12}$, $R_{13}$, $R_{21}$, $R_{22}$, $R_2$, $R_3$, and $R_4$ is —H.

Preferably each of $R_{11}$, $R_2$, and $R_4$ is —H, and each of $R_{12}$, $R_{13}$, $R_{21}$, $R_{22}$, and $R_3$ is an acetate or benzoate group.

Optionally, $R_{11}$, is —H, and each of $R_{12}$, $R_{13}$, $R_{21}$, $R_{22}$, $R_2$, $R_3$, and $R_4$ is an acetate or benzoate group.

Additionally each of $R_{11}$, $R_{13}$, $R_2$, and $R_4$ is —H, and each of $R_{12}$, $R_{21}$, $R_{22}$, and $R_3$ is an acetate or benzoate group.

Optionally, each of $R_{11}$, and $R_{13}$ is —H, and each of $R_{12}$, $R_{21}$, $R_{22}$, $R_2$, $R_3$, and $R_4$ is an acetate or benzoate group.

Each of $R_{11}$, $R_{12}$, and $R_{13}$ can be —H, and each of $R_{21}$, $R_{22}$, $R_2$, $R_3$, and $R_4$ can be an acetate or benzoate group.

In one embodiment of the above compound this invention, $R_5$ is —H, and each of $R_{11}$, $R_{12}$, $R_{13}$, $R_{21}$, and $R_{22}$ is an acetate group. This particular embodiment also provides the following three variations:

$R_2$ is an acetate group, and each of $R_3$ and $R_4$ is —H;

$R_3$ is an acetate group, and each of $R_2$ and $R_4$ is —H; or each of $R_2$ and $R_4$ is an acetate group, and $R_3$ is —H.

It is another aspect of this invention to provide a method of reducing tumor cell growth including the step of administering an effective amount of a compound having the formula:

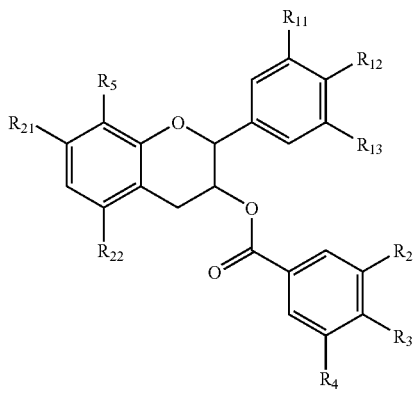

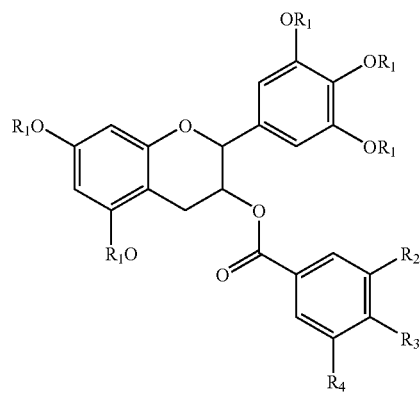

wherein $R_{11}$, $R_{12}$, $R_{13}$, $R_{21}$, $R_{22}$, $R_2$, $R_3$, and $R_4$ are each independently selected from the group consisting of —H, and $C_1$ to $C_{10}$ acyloxyl group; and $R_5$ is selected from the group consisting of —H, $C_1$-$C_{10}$-alkyl, $C_2$-$C_{10}$-alkenyl, $C_2$-$C_{10}$-alkynyl, $C_3$-$C_7$-cycloalkyl, phenyl, benzyl and $C_3$-$C_7$-cycloalkenyl, whereas each of the last mentioned 7 groups can be substituted with any combination of one to six halogen atoms; and at least one of $R_{11}$, $R_{12}$, $R_{13}$, $R_{21}$, $R_{22}$, $R_2$, $R_3$, and $R_4$ is $C_1$ to $C_{10}$ acyloxyl group.

It is yet another aspect of this invention to provide a use of a compound of having the formula:

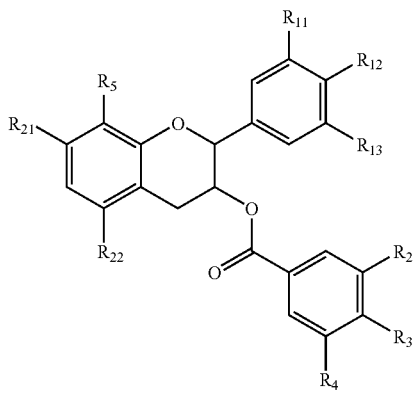

wherein $R_{11}$, $R_{12}$, $R_{13}$, $R_{21}$, $R_{22}$, $R_2$, $R_3$, and $R_4$ are each independently selected from the group consisting of —H, and $C_1$ to $C_{10}$ acyloxyl group; and $R_5$ is selected from the group consisting of —H, $C_1$-$C_{10}$-alkyl, $C_2$-$C_{10}$-alkenyl, $C_2$-$C_{10}$-alkynyl, $C_3$-$C_7$-cycloalkyl, phenyl, benzyl and $C_3$-$C_7$-cycloalkenyl, whereas each of the last mentioned 7 groups can be substituted with any combination of one to six halogen atoms; and least one of $R_{11}$, $R_{12}$, $R_{13}$, $R_{21}$, $R_{22}$, $R_2$, $R_3$, and $R_4$ is $C_1$ to $C_{10}$ acyloxyl group in the manufacturing of a medicament for reducing tumor cell growth.

This invention also provides a compound for inhibiting proteasome having the formula:

wherein $R_1$ is —H;

$R_2$, $R_3$, and $R_4$ are each independently selected from the group consisting of —H and —OH; and at least one of $R_2$, $R_3$, and $R_4$ is —H.

Preferably, $R_2$ can be —OH, and $R_3$=$R_4$=—H. Optionally, $R_3$ may be —OH, and $R_2$=$R_4$=—H; or $R_3$ may be —H, and $R_2$=$R_4$=—OH.

This invention also provides a method of reducing tumor cell growth including the step of administering an effective amount of a compound having the formula:

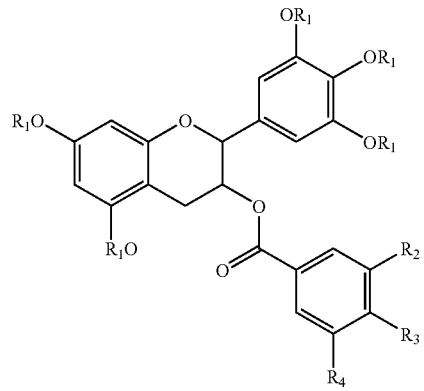

wherein $R_1$ is —H;

$R_2$, $R_3$, and $R_4$ are each independently selected from the group consisting of —H and —OH; and if $R_2$=$R_3$=$R_4$, then $R_2$ is not —OH.

It is another aspect of this invention to provide the use of a compound of having the formula:

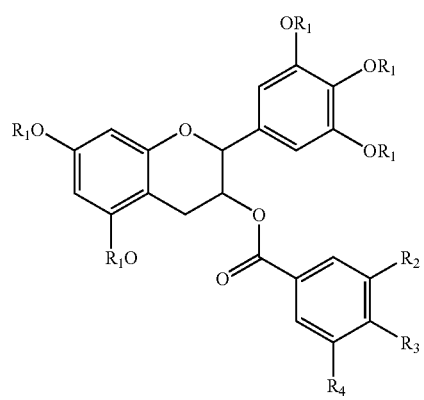

wherein $R_1$ is —H;

$R_2$, $R_3$, and $R_4$ are each independently selected from the group consisting of —H and —OH; and if $R_2$=$R_3$=$R_4$, then $R_2$ is not —OH in the manufacturing of a medicament for reducing tumor cell growth.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENT

Figure 1:
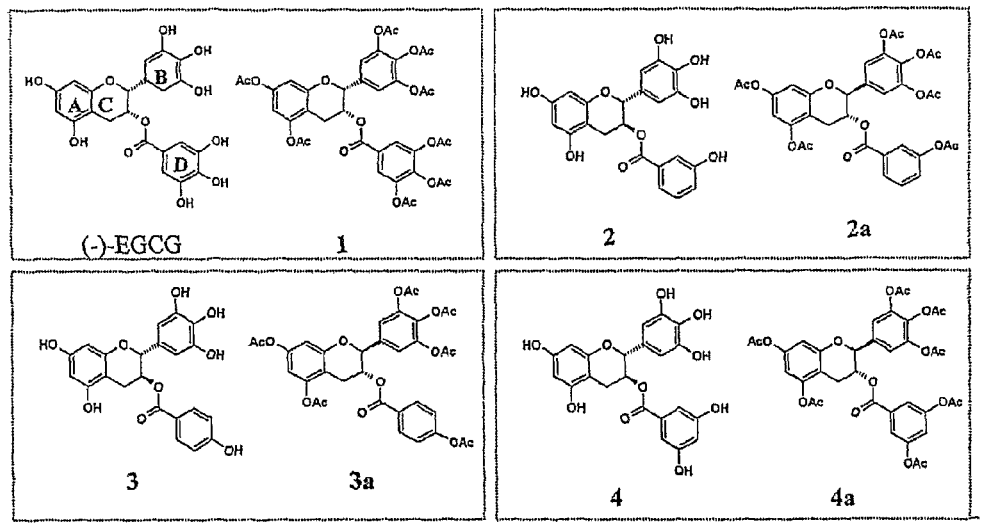
FIG. 1 shows the structures of the (−)-EGCG, and examples of the (−)-EGCG derivatives of this invention.

This invention is now described by way of example with reference to the figures in the following paragraphs.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

In this invention, prodrugs form of (−)-EGCG is synthesized that improves its bioavailability. The prodrugs exhibit: [i] improved stability in physiological conditions at a neutral pH; [ii] remain biologically inactive until enzymatic hydrolysis in vivo, leading to the release of the parent drug; [iii] and lastly, the promoiety groups possess low systemic toxicity Further, three derivatives of (−)-EGCG and their prodrug forms are synthesized, and surprisingly, are found to have higher potency than the natural form of (−)-EGCG itself.

The general formula of the derivatives of (−)-EGCG of this invention in alcohol form has the formula:

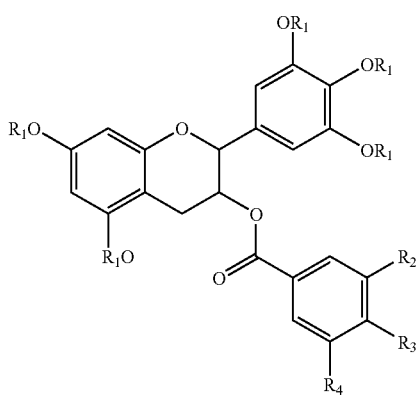

wherein
R is —H; and
$R_2$, $R_3$, and $R_4$ are each independently selected from the group consisting of —H and —OH.

Of course, when $R_2=R_3=R_4$, $R_2$ is —OH, the compound becomes (−)-EGCG, and therefore is not the subject of this invention.

The general formula of the derivatives of (−)-EGCG of this invention in ester form has the formula:

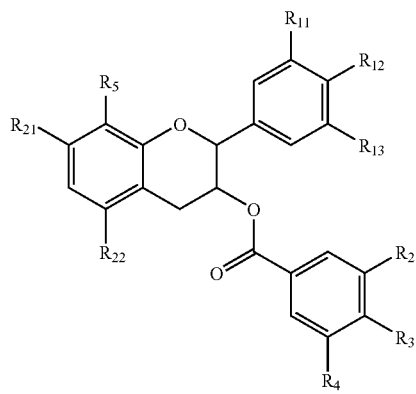

wherein
$R_{11}$, $R_{12}$, $R_{13}$, $R_{21}$, $R_{22}$, $R_2$, $R_3$, and $R_4$ are each independently selected from the group consisting of —H, and $C_1$ to $C_{10}$ acyloxyl group; and
$R_5$ is selected from the group consisting of —H, $C_1$-$C_{10}$-alkyl, $C_2$-$C_{10}$-alkenyl, $C_2$-$C_{10}$-alkynyl, $C_3$-$C_7$-cycloalkyl, phenyl, benzyl and $C_3$-$C_7$-cycloalkenyl, whereas each of the last mentioned 7 groups can be substituted with any combination of one to six halogen atoms;
at least one of $R_{11}$, $R_{12}$, $R_{13}$, $R_{21}$, $R_{22}$, $R_2$, $R_3$, and $R_4$ is $C_1$ to $C_{10}$ acyloxyl group; and
at least one of $R_{11}$, $R_{12}$, $R_{13}$, $R_{21}$, $R_{22}$, $R_2$, $R_3$, and $R_4$ is —H.

In the definitions of the compounds above, collective terms were used which generally represent the following groups:

$C_1$-$C_6$ acyl: having the structure —(CO)—R, wherein R is hydrogen or straight-chain or branched alkyl groups having 1 to 5 carbon atoms, such as methyl, ethyl, propyl, 1-methylethyl, butyl, 1-methylpropyl, 2-methylpropyl, 1,1-dimethylethyl, pentyl, 2-methylbutyl. The alkyl group R can be partially or fully halogenated". The term "partially or fully halogenated" is meant to express that in the groups characterized in this manner the hydrogen atoms may be partially or fully replaced by identical or different halogen atoms, for example chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$-$C_{10}$ acyloxyl: having the structure —O—(CO)—R, wherein R can be any one of —H, $C_1$-$C_9$-alkyl, $C_2$-$C_9$-alkenyl, $C_2$-$C_9$-alkynyl, $C_3$-$C_7$-cycloalkyl, phenyl, benzyl and $C_3$-$C_7$-cycloalkenyl, whereas each of the last mentioned 7 groups can be substituted with any straight chain or branched alkyl groups, such as methyl, ethyl, propyl, 1-methylethyl, butyl, 1-methylpropyl, 2-methylpropyl, 1,1-dimethylethyl, pentyl, 2-methylbutyl. The alkyl group R can be partially or fully halogenated". The term "partially or fully halogenated" is meant to express that in the groups characterized in this manner the hydrogen atoms may be partially or fully replaced by identical or different halogen atoms, for example chloromethyl, dichloromethyl, trichloromethyl, fluoromethyl, difluoromethyl, trifluoromethyl, chlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl. The alkyl group R can be partially or fully substituted by hydroxy, or alkoxy or amino groups, for example, hydroxymethyl, 2-aminoethyl, or 3-methoxypropyl groups.

According to this invention, peracetate (−)-EGCG, 1 was synthesized (FIG. 1). 1 was found to be more stable than (−)-EGCG. The prodrug was biologically inactive against a purified 20S proteasome, but potently inhibited the proteasome in intact tumor cells. Furthermore, administration of the prodrug, but not its parent compound, to intact tumor cells resulted in the loss of phosphorlyated Akt (p-Akt), indicating inactivation of this cancer-associated kinase. Finally, treatment of leukemia Jurkat T cells with 1 induced cell death.

In order to evaluate whether other peractete protected tea polyphenols possessed greater bioactivity than their unprotected parent, several synthetic analogs to (−)-EGCG that possess deletions of the hydroxyl groups on the gallate ring were synthesized. Additionally, to enhance the stability of the molecules, the hydroxyl groups were converted to acetate or benzoate groups to create a prodrug. Surprisingly, the protected analogs were found to be more potent proteasome inhibitors in intact tumor cells than their unprotected counterparts.

The synthesis and characterization of the compounds of this invention will be detailed in the following sections.

Materials and Methods

Reagents

Fetal Bovine Serum was purchased from Tissue Culture Biologicals (Tulare, Calif.). Mixture of penicillin-streptomycin-1-Glutaxnine, RPMI, and DMEM are from Invitrogen (Carlsbad, Calif.). Dimethyl sulfoxide (DMSO), N-acetyl-L-cysteine (NAC), Hoechst 33342, 3-((4,5)-dimethylthiazol-2-yl)-2,5-diphenylteolium bromide (MTT), bovine serum albumin (BSA), and (−)-EGCG were purchased from Sigma (St. Louis, Mo.). Suc-Leu-Leu-Val-Tyr-AMC (for the proteasomal chyrnotrypsin-like activity) was obtained from Biomol (Plymouth Meeting, Pa.). Purified 20s proteasome from rabbit was acquired from Boston Biochem (Cambridge, Mass.). Arnplex Red H202 assay kit was purchased fiom Molecular Probes (Eugene, Oreg.). Monoclonal antibodies to Bax (H280) and Ubiquitin (P4D1), and polyclonal antibodies to IKB-a (C15), and Actin (C11) as well as anti-goat, anti-rabbit, and anti-mouse IgG-horseradish peroxidase were purchased from Santa Cruz Biotechnology (Santa Cruz, Calif.). Monoclonal antibody to p27 (554069) was purchased from BD Biosciences (San Diego, Calif.). Vectashield Mounting Medium with DAPI was purchased from Vector Laboratories, Inc. (Burlingame, Calif.). The Polyclonal antibody, specific to the PARP cleavage site and FITC-conjugated, was acquired from Biosource (Camarillo, Calif.). CaspACE FITC-VAD-FMK marker was purchased fiom Promega (Madison, Wis.).

Synthesis of Synthetic Tea Polyphenol Analogs. Synthesis of 1, 2, 2a, 3, 3a, 4, and 4a (FIG. 1)

1 was prepared according to literature procedures (Kohri, T.; Nanjo, F.; Suzuki, M.; Seto, R.; Matsumoto, N.; Yamakawa, M.; Hojo, H.; Hara, Y.; Desai, D.; Amin, S.; Conaway, C. C.; Chung, F. L. *J Agric Food Chem* 2001, 49: 1042-8), but the synthesis of 1 will be illustrated here. For the synthesis of 1, commercially available (−)-EGCG was used as a starting material. Treating the (−)-EGCG with acetic anhydride and pyridine overnight yielded the desired product 1 in 82% yield (FIG. 1). The structure of 1 was confirmed by 1H and 13C NMR, LRMS and HRMS.

Mp 157.1° C.

LRMS m/z (ESI) 817 (MNa$^+$)

HRMS found, 817.1544; $C_{38}H_{34}O_{19}$Na requires 817.1592.

$^1$H NMR (CDCl$_3$, 500 MHz) δ 7.62 (s, 2H), 7.24 (s, 2H), 6.73 (s, 1H), 6.61 (s, 1H), 5.64 (br s, 1H), 5.18 (s, 1H), 3.02 (m, 2H), 2.29 (s, 3H), 2.28 (s, 9H), 2.27 (s, 3H), 2.24 (s, 3H), 2.23 (s, 6H).

$^{13}$C NMR (CDCl$_3$, 100 MHz) δ 168.89, 168.40, 167.59, 167.43, 166.72, 166.20, 163.51, 154.71, 149.72, 149.64, 143.38, 143.29, 138.93, 135.06, 134.34, 127.41, 122.34, 118.79, 109.42, 109.00, 108.06, 76.46, 67.98, 25.85, 21.06, 20.75, 20.54, 20.11.

(2S*,3R*)-trans-5,7-Bis(benzyloxy)-2-[3,4,5-tris(benzyloxy)phenyl]chroman-3-ol (5)

This compound was synthesized according to literature procedures (Li, L. H.; Chan, T. H. *Org. Lett.* 2001, 3, 739-741).

(2S*,3R*)-trans-5,7-Bis(benzyloxy)-2-[3,4,5-tris(benzyloxy)phenyl]chroman-3-yl 3-(benzyloxy)benzoate (2b)

A quantity of (COCl)$_2$ (0.68 mL) was added to a solution of 3-(benzyloxy)benzoic acid (0.12 g, 0.53 mmol) in CH$_2$Cl$_2$ (10 mL). The mixture was refluxed for 2 hours. After which the excess (COCl)$_2$ and the solvent were removed by distillation and the resulting residue was dried under vacuum overnight. The residue was redissolved in CH$_2$Cl$_2$ (5 mL) and added to a solution of 5 (0.20 g, 0.26 mmol) and DMAP (0.08 g, 0.64 mmol) in CH$_2$C$_2$ (10 mL) at 0° C. The mixture was then stirred at room temperature overnight. Saturated NaHCO$_3$ was added. The organic layer was separated and the aqueous layer was extracted with ethyl acetate. The organic layers were combined, dried (Na$_2$SO$_4$) and evaporated. The residue was purified by column chromatography (hexane: ethyl acetate 4:1) to afford the compound 2b as a white solid (0.22 g, 88%).

LRMS m/z (ESI) 989 (MNa$^+$)

HRMS found, 989.3657; $C_{64}H_{54}O_9$Na requires 989.3666.

$^1$H NMR (CDCl$_3$, 500 MHz) δ 7.54-7.12 (m, 30H), 6.72 (s, 2H), 6.29 (d, J=4.5 Hz, 2H), 5.50 (q, J=7.0 Hz, 1H), 5.10 (d, J=6.5 Hz, 1H), 5.05-4.95 (m, 12H), 3.04 (dd, J=16.5, 6.0 Hz, 1H), 2.89 (dd, J=16.5, 6.5 Hz, 1H).

$^{13}$C NMR (CDCl$_3$, 100 MHz) δ 165.20, 158.81, 158.51, 157.53, 154.68, 152.73, 138.20, 137.60, 136.76, 136.64, 136.25, 133.24, 131.14, 129.32, 128.49, 128.42, 128.40, 128.29, 128.00, 127.96, 127.91, 127.80, 127.69, 127.62, 127.51, 127.43, 127.38, 127.10, 122.13, 119.93, 115.29, 106.13, 101.23, 94.25, 93.74, 78.38, 74.98, 71.07, 70.02, 69.81, 24.18.

(2S*,3R*)-trans-5,7-Bis(hydroxy)-2-[3,4,5-tris(hydroxy)phenyl]chroman-3-yl 3-(hydroxy)benzoate (2)

Suspension of 2b (0.23 g, 0.24 mmol) in THF/MeOH (28 mL/28 mL) and Pd(OH)$_2$ (0.19 g, 20% on carbon) was placed under an H$_2$ atmosphere. The resulting mixture was stirred at room temperature until tlc showed that the reaction was completed. Then the reaction mixture was filtered through cotton to remove the catalyst. After evaporation, the residue was purified by column chromatography (ethyl acetate: CH$_2$Cl$_2$ 2:1) to afford the product 2 as a white solid (80 mg, 79%).

LRMS m/z (ESI) 449 (MNa$^+$)

HRMS found, 449.0887; $C_{22}H_{18}O_9$Na requires 449.0849.

$^1$H NMR (CD$_3$OD, 500 MHz) δ 7.38-6.97 (m, 4H), 6.42 (s, 2H), 5.97 (q, J=2.5 Hz, 2H), 5.40 (q, J=6.0 Hz, 1H), 5.03 (d, J=6.0 Hz, 1H), 2.85 (dd, J=16.5, 5.0 Hz, 1H), 2.74 (dd, J=16.5, 6.0 Hz, 1H).

$^{13}$C NMR (CD$_3$OD, 100 MHz) δ 165.87, 157.00, 156.52, 156.03, 154.88, 145.42, 132.50, 130.91, 129.17, 120.29, 119.90, 115.45, 105.00, 98.07, 95.00, 94.12, 77.78, 70.15, 22.71.

(2S*,3R*)-trans-5,7-Bis(acetyloxy)-2-[3,4,5-tris(acetyloxy)phenyl]chroman-3-yl 3-acetyloxybenzoate (2a)

Suspension of 2b (0.1 g, 0.1 mmol) in THF/MeOH (12 mL/12 mL) and Pd(OH)$_2$ (0.08 g, 20% on carbon) was placed under an H$_2$ atmosphere. The resulting mixture was stirred at room temperature until tlc showed that the reaction was completed. Then the reaction mixture was filtered through cotton to remove the catalyst. The filtrate was evaporated to afford the debenzylated compound (2) which was used immediately in the next step without purification. The obtained debenzylated compound was dissolved in pyridine (4 mL) and acetic anhydride (2 mL). The resulting mixture was stirred at room temperature for overnight. After which, the acetic anhydride and pyridine were removed in vacuo. The resulting residue was taken up in 20 mL of CH$_2$Cl$_2$, and the solution was washed with 5×5 mL of H$_2$O and 5 mL of brine, dried over Na$_2$SO$_4$, and evaporated. The crude product was purified by column chromatography (hexane: ethyl acetate 1:1) to afford the compound 2a as a white powder (0.061 g, 85%).

Mp 71.6° C.

LRMS m/z (ESI) 701 (MNa$^+$)

HRMS found, 701.1541 $C_{34}H_{30}O_{15}$Na requires 701.1482.

$^1$H NMR (CDCl$_3$, 500 MHz) δ 7.79 (d, J=8.0 Hz, 1H), 7.64 (s, 1H), 7.42 (t, J=8.0 Hz, 1H), 7.28 (s, 1H), 7.17 (s, 2H), 6.69 (s, 1H), 6.64 (s, 1H), 5.46 (q, J=5.5 Hz, 1H), 5.32 (d, J=5.5 Hz, 1H), 3.02 (dd, J=17.0, 5.0 Hz, 1H), 2.80 (dd, J=17.0, 6.0 Hz, 1H), 2.32 (s, 3H), 2.29 (s, 3H), 2.27 (s, 3H), 2.26 (s, 9H).

$^{13}$C NMR (CDCl$_3$, 100 MHz) δ 169.10, 168.81, 168.24, 167.47, 166.61, 164.61, 154.00, 150.42, 149.76, 149.28, 143.47, 135.74, 134.48, 130.72, 129.42, 127.18, 126.68, 122.79, 118.58, 109.84, 108.81, 107.54, 69.17, 23.65, 20.96, 20.92, 20.65, 20.47, 20.10.

(2S*,3R*)-trans-5,7-Bis(benzyloxy)-2-[3,4,5-tris(benzyloxy)phenyl]chroman-3-yl 4-(benzyloxy)benzoate (3b)

The title compound was prepared in a similar manner as described for 2b, using 5 (0.08 g, 0.1 mmol) and 4-(benzyloxy)benzoic acid (0.049 g, 0.22 mmol) giving 3b as a white solid (0.087 g, 90%).

LRMS m/z (ESI) 989 (MNa$^+$)
HRMS found, 989.3666 $C_{64}H_{54}O_9Na$ requires 989.3666.
$^1$H NMR (CDCl$_3$, 500 MHz) δ 7.91 (d, J=9.0 Hz, 2H), 7.47-7.22 (m, 30H), 6.95 (d, J=9.0 Hz, 2H), 6.74 (s, 2H), 6.31 (dd, J=5.5, 2.5 Hz, 2H), 5.52 (q, J=6.5 Hz, 1H), 5.14 (d, J=6.5 Hz, 1H), 5.07-4.97 (m, 12H), 3.02 (dd, J=17.0, 5.5 Hz, 1H), 2.87 (dd, J=16.5, 7.0 Hz, 1H).
$^{13}$C NMR (CDCl$_3$, 100 MHz) δ 165.08, 162.49, 158.76, 157.53, 154.65, 152.69, 138.09, 137.63, 136.79, 136.70, 136.66, 136.00, 133.38, 131.61, 128.55, 128.49, 128.40, 128.29, 128.09, 127.96, 127.91, 127.78, 127.69, 127.62, 127.43, 127.38, 127.30, 127.09, 122.40, 114.33, 106.08, 101.30, 94.22, 93.67, 78.37, 74.98, 71.05, 69.95, 69.79, 69.26, 24.01.

(2S*,3R*)-trans-5,7-Bis(hydroxy)-2-[3,4,5-tris(hydroxy)phenyl]chroman-3-yl 4-(hydroxy)benzoate (3)

The title compound was prepared in a similar manner as described for 2 using 3b (0.24 g, 0.25 mmol) to afford 3 as a white solid (79 mg, 75%).

LRMS m/z (ESI) 449 (MNa$^+$)
HRMS found, 449.0840; $C_{22}H_{18}O_9Na$ requires 449.0849.
$^1$H NMR (CD$_3$OD, 500 MHz) δ 7.75 (d, J=8.5 Hz, 2H), 6.77 (d, J=8.5 Hz, 2H), 6.42 (s, 2H), 5.95 (dd, J=8.0, 2.5 Hz, 2H), 5.35 (q, J=6.0 Hz, 1H), 5.00 (d, J=6.0 Hz, 1H), 2.85 (dd, J=16.5, 5.0 Hz, 1H), 2.71 (dd, J=16.5, 6.5 Hz, 1H).
$^{13}$C NMR (CD$_3$OD, 100 MHz) δ 165.88, 161.99, 156.54, 156.05, 154.95, 145.41, 132.46, 131.31, 129.25, 120.61, 114.57, 104.98, 98.14, 94.91, 94.04, 78.00, 69.81, 22.98.

(2S*,3R*)-trans-5,7-Bis(acetyloxy)-2-[3,4,5-tris(acetyloxy)phenyl]chroman-3-yl 4-(acetyloxy)benzoate (3a)

The title compound was prepared in a similar manner as described for 2a, using 3b (0.15 g, 0.16 mmol) to afford 3a as a white solid (92.6 mg, 88%).

Mp 189.4° C.
LRMS m/z (ESI) 701 (MNa$^+$)
HRMS found, 701.1467; $C_{34}H_{30}O_{15}Na$ requires 701.1482.
$^1$HNMR (CDCl$_3$, 500 MHz) δ 7.94 (d, J=9.0 Hz, 2H), 7.17 (s, 2H), 7.13 (d, J=9.0 Hz, 2H), 6.69 (d, J=2.0 Hz, 1H), 6.63 (d, J=2.0 Hz, 1H), 5.45 (q, J=6.0 Hz, 1H), 5.32 (d, J=6.0 Hz, 1H), 3.01 (dd, J=16.5, 5.0 Hz, 1H), 2.79 (dd, J=16.5, 6.0 Hz, 1H), 2.31 (s, 3H), 2.29 (s, 3H), 2.27 (s, 3H), 2.26 (s, 9H).
$^{13}$C NMR (CDCl$_3$, 100 MHz) δ 168.81, 168.64, 168.26, 167.49, 166.62, 164.74, 154.48, 154.02, 149.76, 149.30, 143.49, 135.82, 134.50, 131.28, 126.76, 121.60, 118.59, 109.90, 108.80, 107.51, 69.01, 23.64, 20.97, 20.63, 20.46, 20.00.

(2S*,3R*)-trans-5,7-Bis(benzyloxy)-2-[3,4,5-tris(benzyloxy)phenyl]chroman-3-yl 3,5-bis(benzyloxy)benzoate (4b)

The title compound was prepared in a similar manner as described for 2b, using 5 (0.3 g, 0.4 mmol) and 3,5-bis(benzyloxy)benzoic acid (0.27 g, 0.81 mmol) giving 4b as a white solid (0.36 g, 85%).

LRMS m/z (ESI) 1095 (MNa$^+$)
HRMS found, 1095.4059; $C_{71}H_{60}O_{10}Na$ requires 1095.4084.
$^1$HNMR (CDCl$_3$, 500 MHz) δ 7.47-7.17 (m, 35H), 6.76 (s, 1H), 6.73 (s, 1H), 6.30 (d, J=4.5 Hz, 2H), 5.48 (q, J=7.0 Hz, 1H), 5.08 (d, J=7.0 Hz, 1H), 5.04-4.92 (m, 14H), 3.07 (dd, J=17.0, 5.5 Hz, 1H), 2.85 (dd, J=17.0, 7.0 Hz, 1H).
$^{13}$C NMR (CDCl$_3$, 100 MHz) δ 165.14, 159.73, 158.98, 157.67, 154.88, 152.87, 137.77, 136.91, 136.82, 136.78, 136.29, 133.35, 131.86, 128.61, 128.56, 128.52, 128.41, 128.15, 128.10, 128.02, 127.94, 127.81, 127.76, 127.67, 127.51, 127.24, 108.52, 106.93, 106.30, 101.38, 94.43, 93.93, 78.57, 75.12, 71.17, 70.26, 70.15, 70.11, 69.92, 24.58.

(2S*,3R*)-trans-5,7-Bis(hydroxy)-2-[3,4,5-tris(hydroxy)phenyl]chroman-3-yl 3,5-bis(hydroxy)benzoate (4)

The title compound was prepared in a similar manner as described for 2 using 4b (0.17 g, 0.16 mmol) to afford 4 as a white solid (50 mg, 71%).

LRMS m/z (ESI) 465 (MNa$^+$)
HRMS found, 465.0844; $C_{22}H_{18}O_9Na$ requires 465.0798.
$^1$H NMR (CD$_3$OD, 500 MHz) δ 6.85 (d, J=2.0 Hz, 2H), 6.44 (t, J=2.0 Hz, 1H), 6.41 (s, 2H), 5.96 (s, 2H), 5.40 (dd, J=10.5, 5.0 Hz, 1H), 5.05 (d, J=5.0 Hz, 1H), 2.80 (dd, J=16.5, 5.0 Hz, 1H), 2.73 (dd, J=16.5, 5.0 Hz, 1H).
$^{13}$C NMR (CD$_3$OD, 100 MHz) δ 165.81, 158.10, 156.56, 156.06, 154.83, 145.43, 132.44, 131.49, 129.28, 107.34, 106.86, 104.81, 97.93, 94.88, 94.06, 77.60, 69.95, 22.28.

(2S*,3R*)-trans-5,7-Bis(acetyloxy)-2-[3,4,5-tris(acetyloxy)phenyl]chroman-3-yl 3,5-bis(acetyloxy)benzoate (4a)

The title compound was prepared in a similar manner as described for 2a using 4b (0.15 g, 0.14 mmol) to afford 4a as a white solid (72 mg, 70%).

Mp 105.5° C.
LRMS m/z (ESI) 759 (MNa$^+$)
HRMS found, 759.1530; $C_{36}H_{32}O_{17}Na$ requires 759.1537.
$^1$H NMR (CDCl$_3$, 500 MHz) δ 7.54 (d, J=2.0 Hz, 2H), 7.17 (s, 2H), 7.13 (t, J=2.0 Hz, 1H), 6.69 (d, J=2.0 Hz, 1H), 6.64 (d, J=2.0 Hz, 1H), 5.45 (q, J=6.0 Hz, 1H), 5.29 (d, J=6.5 Hz, 1H), 3.01 (dd, J=17.0, 5.0 Hz, 1H), 2.79 (dd, J=17.0, 6.5 Hz, 1H), 2.30 (s, 6H), 2.28 (s, 3H), 2.27 (s, 3H), 2.26 (s, 3H), 2.25 (s, 6H).
$^{13}$C NMR (CDCl$_3$, 100 MHz) δ 168.80, 168.62, 168.21, 167.45, 166.60, 163.78, 153.96, 150.78, 149.77, 149.27, 143.46, 135.55, 134.48, 131.26, 120.57, 120.29, 118.56, 109.79, 108.86, 107.57, 69.48, 23.77, 20.94, 20.86, 20.64, 20.45, 19.99.

As the carboxylate or —OH groups of the compound 1, 2, 3 and 4 can readily undergo acyl exchange, one skilled in the art shall be able to replace the acyl groups on the carboxylate groups of these compounds.

Synthesis of Synthetic Tea Polyphenol Analogs

General

Starting materials and reagents, purchased from commercial suppliers, were used without further purification. Literature procedures were used for preparation of (2R,3S) trans and (2R,3R)-cis-5,7-bis(benzyloxy)-2-(4-bezyloxyphenyl)chroman-3-ol, (2R,3S) trans and (2R,3R)-cis-5,7-bis(benzyloxy)-2-[3,4-bis(benzyloxy)-phenyl]chroman-3-ol, (2R,3R)- cis-5,7-bis(hydroxyl)-2-(4-hydroxyphenyl)chroman-3-yl 3,4,5-trihydroxybenzoate (Sheng Biao Wan; Tak Hang Chan. *Tetrahedron*, 2004, 60, 8207).

Anhydrous THF was distilled under nitrogen from sodium benzophenone ketyl. Anhydrous methylene chloride was distilled under nitrogen from $CaH_2$. Anhydrous DMF was distilled under vacuum from $CaH_2$. Reaction flasks were flame-dried under a stream of $N_2$. All moisture-sensitive reactions were conducted under a nitrogen atmosphere. Flash chromatography was carried out using silica-gel 60 (70-230 mesh). The melting points were uncorrected. $^1$H-NMR and $^{13}$C NMR (400 MHz) spectra were measured with TMS as an internal standard when $CDCl_3$ and acetone-d6 were used as a solvent. High-resolution (ESI) MS spectra were recorded using a QTOF-2 Micromass spectrometer.

(+)-(2R,3S)-5,7-Bis(benzyloxy)-2-[3,4-bis(benzyloxy)phenyl]chroman-3-yl 4-benzyloxybenzoate (102)

Under an $N_2$ atmosphere, a solution of 4-benzyloxybenzoic acid (140 mg, 0.61 mmol) was refluxed with oxally chloride (1 mL) in dry $CH_2Cl_2$ (10 mL) and one drop of DMF for 3 h. The excess oxally chloride and solvent were removed by distillation and the residue was dried under vacuum for 3 h and dissolved in $CH_2Cl_2$ (2 mL). This solution was added dropwise to a solution of (2R,3S)-trans-5,7-bis(benzyloxy)-2-[3,4-bis(benzyloxy)phenyl]chroman-3-ol (195 mg, 0.3 mmol) and DMAP (75 mg, 0.62 mmol) in $CH_2Cl_2$ (15 mL) at 0° C. The mixture was stirred at rt overnight, then saturated $NaHCO_3$ aqueous solution was added. The organic layer was separated, and the aqueous layer was extracted with $CH_2Cl_2$. The organic phases were combined, dried ($MgSO_4$) and evaporated. The residue was purified by flash chromatography on silica gel (EtOAc/n-hexane=1/4 v/v) to afford the desired compound (220 mg, 85.0%). Recrystallization in EtOAc and n-hexane gave a white powder: mp 148-150° C.; $[\alpha]_D$=+18.3 (c=1, $CHCl_3$); $^1$H NMR ($CDCl_3$, 400 MHz): δ 7.88 (d, J=8.6 Hz, 2H), 7.43-7.28 (m, 25H), 7.01 (s, 1H), 6.93-6.88 (m, 4H), 6.28 (s, 2H), 5.53-5.50 (m, 1H), 5.14 (d, J=6.4 Hz, 1H), 5.11 (s, 2H), 5.07 (s, 2H), 5.04 (S, 2H), 5.02 (s, 2H), 5.01 (s, 2H), 3.04 (A of ABq, J=16.8, 4.6 Hz, 1H), 2.87 (B of ABq, J=16.8, 6.3 Hz, 1 H); $^{13}$C NMR ($CDCl_3$, 400 MHz): δ 165.0, 162.3, 158.6, 157.4, 154.6, 148.5, 136.9, 136.6, 136.5, 135.9, 131.4, 130.9, 128.4, 128.3, 128.2, 128.1, 127.9, 127.7, 127.6, 127.5, 127.3, 127.1, 126.9, 122.3, 119.5, 114.6, 114.1, 113.1, 101.1, 94.1, 93.4, 78.0, 71.0, 70.9, 69.9, 69.8, 69.6, 69.1, 23.8; HRMS (ESI) calcd for $C_{57}H_{48}O_8Na$ (M+Na) 883.3247. found 883.3241.

(−)-(2R,3R)-5,7-Bis(benzyloxy)-2-[3,4-bis(benzyloxy)phenyl]chroman-3-yl 4-benzyloxybenzoate (104)

Following the preparation procedure of 102, the esterification of (2R,3R)-cis-5,7-bis(benzyloxy)-2-[3,4-bis(benzyloxy)phenyl]chroman-3-ol with 4-benzyloxybenzoic acid afforded 104 with 86% yield. mp 149-151° C.; $[\alpha]_D$=−3.1 (c=1.5, $CHCl_3$); $^1$H NMR ($CDCl_3$, 400 MHz): δ 7.92 (d, J=8.8 Hz, 2H), 7.44-7.26 (m, 25H), 7.15 (d, J=1.6 Hz, 1H), 6.91-6.87 (m, 4H), 6.32 (d, J=2.1 Hz, 1H), 6.28 (d, J=2.1 Hz, 1H), 5.63 (bs, 1H), 5.08 9s, 2H), 5.06 (s, 1H), 5.03-5.00 (m, 6H), 4.92 (AB, J=11.6 Hz, 2H), 3.08 (bs, 2H); 13C NMR (CDCl3, 400 MHz): δ165.1, 162.5, 158.6, 157.9, 155.6, 148.9, 148.7, 137.1, 137.0, 136.8, 136.7, 136.0, 131.8, 131.1, 128.6, 128.5, 128.4, 128.3, 128.1, 127.9, 127.8, 127.6, 127.5, 127.4, 127.3, 127.2, 127.1, 122.5, 119.9, 114.6, 114.3, 113.5, 100.9, 94.6, 93.7, HRMS (ESI) calcd for $C_{57}H_{48}O_8Na$ (M+Na) 883.3244. found 883.3241.

(+)-(2R,3S)-5,7-Bis(benzyloxy)-2-(4-benzyloxyphenyl)chroman-3-yl 4-benzyloxybenzoate (110)

Following the preparation procedure of 102, the esterification of (2R,3S)-5,7-bis(benzyloxy)-2-(4-benzyloxyphenyl)chroman-3-ol with 4-benzyloxybenzoic acid afforded 110 with 86% yield. mp 117-119° C.; $[\alpha]_D$=+24.5 (c=1.2, $CHCl_3$); $^1$H NMR ($CDCl_3$, 400 MHz): δ 7.86 (d, J=8.8 Hz, 2H), 7.42-7.26 (m, 22H), 6.92 (AB, J=2.6 Hz, 4H), 6.29 (AB, J=1.9 Hz, 2H), 5.56-5.51 (m, 1H), 5.17 (d, J=6.5 Hz, 1H), 5.05 (s, 2 H), 4.98 (s, 4H), 4.97 (s, 2H), 3.10 (A of ABq, J=16.8, 5.4 Hz, 1H), 2.88 (B of ABq, J=16.8, 6.6 Hz, 1H); $^{13}$C NMR ($CDCl_3$, 400 MHz): δ165.2, 162.4, 158.8, 158.6, 157.6, 155.0, 136.8, 136.7, 136.1, 131.6, 130.3, 128.6, 128.5, 128.4, 128.1, 127.9, 127.8, 127.5, 127.3, 127.1, 122.5, 114.8, 114.3, 101.4, 94.3, 93.6, 78.3, 70.0, 69.9, 69.8, 69.4, 24.2; HRMS (ESI) calcd for $C_{50}H_{42}O_7Na$ (M+Na) 777.2828. found 777.2840.

(−)-(2R,3R)-5,7-Bis(benzyloxy)-2-(4-benzyloxyphenyl)chroman-3-yl 4-benzyloxybenzoate (111)

Following the preparation procedure of 102, the esterification of (2R,3R)-5,7-bis(benzyloxy)-2-(4-benzyloxyphenyl)chroman-3-ol with 4-benzyloxybenzoic acid afforded 111 with 88% yield. mp 129-131° C.; $[\alpha]_D$=−51.8 (c=3.9, $CHCl_3$); $^1$H NMR ($CDCl_3$, 400 MHz): δ 7.88 (d, J=8.8 Hz, 2H), 7.43-7.27 (m, 22H), 6.91 (s, 2H), 6.89 (s, 2 H), 6.33 (d, J=2.0 Hz, 1H), 6.27 (d, J=2.0 Hz, 1H), 5.62 (bs, 1H), 5.11 (bs, 1H), 5.05 (s, 2 H), 5.01 (s, 2H), 4.98 (s, 4H), 3.09 (d, J=2.9 Hz, 2H); $^{13}$C NMR ($CDCl_3$, 400 MHz): δ 165.3, 162.4, 158.6, 158.4, 157.9, 155.6, 136.8, 136.7, 136.1, 131.7, 130.1, 128.6, 128.5, 128.4, 128.1, 127.9, 127.8, 127.7, 127.5, 127.4, 127.3, 127.1, 122.5, 114.5, 114.3, 100.9, 94.6, 93.7, 77.4, 70.0, 69.9, 69.8, 68.1, 26.0; HRMS (ESI) calcd for $C_{50}H_{42}O_7Na$ (M+Na) 777.2828. found 777.2815.

(+)-(2R,3S)-5,7-dihydroxy-2-(3,4-dihydroxyphenyl)chroman-3-yl 4-hydroxybenzoate (11)

Under an $H_2$ atmosphere, $Pd(OH)_2$/C (20%, 100 mg) was added to a solution of 102 (200 mg, 0.23 mmol) in a solvent mixture of THF/MeOH (1:1 v/v, 20 mL). The resulting reaction mixture was stirred at r.t. under $H_2$ for 6 h, TLC showed that the reaction was completed. The reaction mixture was filtered to remove the catalyst. The filtrate was evaporated, and the residue was rapidly purified by flash chromatograph on silica gel (10% MeOH/$CH_2Cl_2$, then 20% MeOH/$CH_2Cl_2$) to afford 11 (82 mg, 87% yield): mp 220-222° C. (decomposed); $[\alpha]_D$=+87.2 (c=2.0, EtOH); $^1$H NMR (acetone-d$_6$, 400 MHz): δ 7.98 (d, J=8.8 Hz, 2H), 7.13 (s, 1H), 7.04 (d, J=8.8 Hz, 2H), 6.99-6.96 (m, 2H), 6.27 (d, J=2.2 Hz, 1H), 6.19 (d, J=2.2 Hz, 1H), 5.62 (dd, J=11.8, 6.3 Hz, 1H), 5.34 (d, J=6.3 Hz), 3.15 (A of ABq, J=16.5, 5.2 Hz, 1H), 3.00 (B of ABq, J=16.5, 6.4 Hz, 1H); $^{13}$C NMR (acetone-d6, 400 MHz): δ 163.3, 160.0, 155.2, 154.5, 153.6, 143.1, 129.9, 128.7, 119.6, 116.6, 113.4, 113.3, 111.8, 111.7, 96.7, 93.8, 93.0, 76.2, 67.9, 21.9; HRMS (ESI) calcd for $C_{22}H_{18}O_8Na$ (M+Na) 433.0899. found 433.0909.

(−)-(2R,3R)-5,7-dihydroxy-2-(3,4-dihydroxyphenyl)chroman-3-yl 4-hydroxybenzoate (12)

Following the preparation procedure of 11, the hydrogenolysis of 104 afforded 12 with 85% yield. mp 241-243° C.

(decomposed); $[\alpha]_D=-145.2$ (c=0.5, EtOH), (Lit −144.4, c=1 in Me$_2$CO);[4] $^1$H NMR (acetone-d$_6$, 400 MHz): δ 7.89 (d, J=8.8 Hz, 2H), 7.19 (d, J=1.9 Hz, 1H), 7.01 (A of ABq, J=8.2, 1.9 Hz, 1H), 6.97 (d, J=8.8 Hz, 2H), 6.89 (B of AB, J=8.2 Hz, 1H), 6.17 (d, J=2.3 Hz, 1H), 6.14 (d, J=2.3 Hz, 1H), 5.65 (m, 1H), 5.24 (bs, 1H), 3.19 (A of ABq, J=17.4, 4.5 Hz, 1H), 3.07 (B of AB, J=17.4, 2.0 Hz, 1H); 13C NMR (acetone-d$_6$, 400 MHz): δ 164.8, 161.6, 156.8, 156.4, 156.0, 144.6, 144.5, 131.5, 130.3, 121.4, 118.0, 114.9, 114.6, 113.8, 97.8, 95.4, 94.7, 76.9, 68.5, 25.5; HRMS (ESI) calcd for C$_{22}$H$_{18}$O$_8$Na (M+Na) 433.0899. found 433.0895.

(+)-(2R,3S)-5,7-dihydroxy-2-(4-hydroxyphenyl)chroman-3-yl 4-hydroxybenzoate (112)

Following the preparation procedure of 11, the hydrogenolysis of 110 afforded 112 with 90% yield. mp 253-255° C. (decomposed); $[\alpha]_D=+45.9$ (c=3.5, EtOH); $^1$H NMR (acetone-d$_6$, 400 MHz): δ 7.74 (d, J=8.7 Hz, 2H), 7.26 (d, J=8.5 Hz, 2H), 6.81 (d, J=8.7 Hz, 2H), 6.76 9d, J=8.5 Hz, 2H), 6.04 (d, J=2.2 Hz, 1H), 5.95 (d, J=2.2 Hz, 1H), 5.39 (dd, J=12.4, 6.9 Hz, 1H), 5.11 (d, J=6.9 Hz, 1H), 3.21 (A of ABq, J=16.3, 5.3 Hz, 1H), 2.98 (B of ABq, J=16.3, 7.0 Hz, 1H); 13C NMR (acetone-d$_6$, 400 MHz): δ 163.7, 160.6, 156.0, 155.9, 155.1, 154.3, 130.4, 128.3, 126.8, 120.1, 113.9, 97.3, 94.4, 93.5, 77.0, 68.5, 23.0; HRMS (ESI) calcd for C$_{22}$H$_{18}$O$_7$Na (M+Na) 417.0950. found 417.0946.

(−)-(2R,3R)-5,7-dihydroxy-2-(4-hydroxyphenyl)chroman-3-yl 4-hydroxybenzoate (10)

Following the preparation procedure of 11, the hydrogenolysis of 111 afforded 10 with 89% yield. mp 214-216° C. (decomposed); $[\alpha]_D=-116.1$ (c=2.0, EtOH); $^1$H NMR (acetone-d$_6$, 400 MHz): δ 7.94 (d, J=8.6 Hz, 2H), 7.56 (d, J=8.6 Hz, 2H), 7.01 (d, J=6.8 Hz, 2H), 6.95 (d, J=6.8 Hz, 2H), 6.22 (d, J=2.2 Hz, 1H), 6.20 (d, J=2.2 Hz, 1H), 5.73 (bs, 1H), 5.37 (bs, 1H), 3.26 (A of ABq, J=17.4, 4.5 Hz, 1H), 3.14 (B of ABq, J=17.4, 2.2 Hz, 1H); 13C NMR (acetone-d$_6$, 400 MHz): δ 164.5, 161.3, 156.6, 156.5, 156.1, 155.8, 131.2, 129.3, 127.5, 121.1, 114.7, 114.4, 97.5, 95.2, 94.5, 76.7, 68.2, 25.2; HRMS (ESI) calcd for C$_{22}$H$_{18}$O$_7$Na (M+Na) 417.0950. found 417.0946.

(+)-(2R,3S)-5,7-dihydroxy-2-(3,4-dihydroxyphenyl)chroman-3-yl 4-hydroxybenzoate pentaacetate (22*)

Under an N$_2$ atmosphere, to a solution of (+)-(2R,3S)-5,7-dihydroxy-2-(3,4-dihydroxyphenyl)chroman-3-yl 4-hydroxybenzoate 11 (20 mg, 0.048 mmol) in pyridine (1 ml), acetic anhydride (0.2 ml) was added dropwise at 0° C. The reaction mixture was stirred at rt overnight. The excess pyridine was distilled under vacuum. The residue was purified by flash chromatograph on silica gel (EtOAc/n-hexane, 1/1 in v/v) to afford 22* (34 mg, 95% yield). mp: mp 149-151° C.; $[\alpha]_D=+42.5$ (c=1.2, CHCl$_3$); $^1$H NMR (CDCl$_3$, 400 MHz): δ 7.96 9d, J=8.7 Hz, 2H), 7.31 (A of ABq, J=8.4, 1.8 Hz, 1H), 7.26 (d, J=1.8 Hz, 1H), 7.21 (B of AB, J=8.4 Hz, 1H), 7.15 (d, J=8.7 Hz, 2H), 6.70 (d, J=2.2 Hz, 1H), 6.63 (d, J=2.2 Hz, 1H), 5.51 (dd, J=11.2, 6.0 Hz, 1H), 5.33 (d, J=6.0 Hz, 1H), 3.04 (A of ABq, J=16.8, 5.0 Hz, 1H), 2.83 (B of ABq, J=16.8, 6.0 Hz, 1H), 2.31 (s, 3H), 2.29 (s, 3H), 2.28 (s, 3H), 2.27 (s, 6H); $^{13}$C NMR (CDCl$_3$, 400 MHz): δ 168.8, 168.7, 168.3, 167.9, 164.8, 154.5, 154.3, 149.8, 149.4, 142.2, 142.1, 136.1, 131.3, 126.9, 124.3, 123.7, 122.0, 121.6, 121.3, 110.0, 108.7, 107.6, 77.7, 69.1, 23.9, 21.0, 20.7, 20.5; HRMS (ESI) calcd for C$_{32}$H$_{28}$O$_{13}$Na (M+Na) 643.1428. found 643.1437.

(−)-(2R,3R)-5,7-dihydroxy-2-(3,4-dihydroxyphenyl)chroman-3-yl 4-hydroxybenzoate pentaacetate (23*)

Following the preparation procedure of 22*, the acetylation of 12 afforded 23* with 96% yield. mp 91-93° C.; $[\alpha]_D=-26.5$ (c=0.5, CHCl$_3$); $^1$H NMR (CDCl$_3$, 400 MHz): δ 7.89 (d, J=8.7 Hz, 2H), 7.37 (d, J=1.9 Hz, 1H), 7.34 (A of ABq, J=8.4, 1.9 Hz, 1H), 7.21 (B of ABq, J=8.4 Hz, 1H), 7.10 (d, J=8.7 Hz, 2H), 6.74 (d, J=2.2 Hz, 1H), 6.59 (d, J=2.2 Hz, 1H), 5.64 (bs, 1H), 5.22 (bs, 1H), 3.11 (A of ABq, J=18.0, 4.5 Hz, 1H), 3.04 (B of ABq, J=18.0, 2.4 Hz, 1H), 2.29 (s, 3H), 2.28 (s, 6H), 2.26 (s, 3H), 2.25 (s, 3H); $^{13}$C NMR (CDCl$_3$, 400 MHz): δ 168.8, 168.6, 168.3, 167.9, 167.8, 164.9, 154.9, 154.4, 149.7, 142.0, 141.8, 135.7, 131.3, 126.9, 124.2, 123.4, 121.7, 121.5, 109.5, 108.8, 108.0, 67.5, 26.0, 21.0, 20.7, 20.5; HRMS (ESI) calcd for C$_{32}$H$_{28}$O$_{13}$Na (M+Na) 643.1428. found 643.1420.

(+)-(2R,3S)-5,7-dihydroxy-2-(3,4-dihydroxyphenyl)chroman-3-yl 3,4,5-trihydroxybenzoate heptaacetate (24*)

Following the preparation procedure of 22*, the acetylation of (+)-(2R,3S)-5,7-dihydroxy-2-(3,4-dihydroxyphenyl)chroman-3-yl 3,4,5-trihydroxybenzoate (Sheng Biao Wan; Di Chen; Q. Ping Dou and Tak Hang Chan. *Bioorganic & Medicinal Chemistry*, 2004, 12, 3521) afforded 24* with 95% yield. mp 140-142° C.; $[\alpha]_D=+35.3$ (c=3.0, CHCl$_3$); $^1$H NMR (CDCl$_3$, 400 MHz): δ 7.67 (s, 2H), 7.28-7.26 (m, 2H), 7.20 (d, J=8.3 Hz, 1H), 6.68 (d, J=2.2 Hz, 1H), 6.62 (d, J=2.2 Hz, 1H), 5.47 (dd, J=11.8, 6.2 Hz, 1H), 5.27 (d, J=6.2 Hz, 1H), 3.02 (A of ABq, J=16.8, 5.2 Hz, 1H), 2.81 (B of ABq, J=16.8, 6.6 Hz, 1H), 2.29 (m, 9H), 2.27 (s, 3H), 2.26 (s, 3H), 2.25 (s, 6H); $^{13}$C NMR (CDCl$_3$, 400 MHz): δ 168.8, 168.2, 167.8, 167.5, 166.2, 163.3, 154.2, 149.8, 149.3, 143.3, 142.1, 138.9, 135.7, 127.5, 124.2, 123.7, 122.2, 121.6, 109.9, 108.8, 107.6, 77.5, 69.7, 24.0, 21.0, 20.7, 20.5, 20.0; HRMS (ESI) calcd for C$_{36}$H$_{32}$O$_{17}$Na (M+Na) 759.1537. found 759.1552.

(−)-(2R,3R)-5,7-dihydroxy-2-(3,4-dihydroxyphenyl)chroman-3-yl 3,4,5-trihydroxybenzoate heptaacetate (25*)

Following the preparation procedure of 22*, the acetylation of (−)-(2R,3R)-5,7-dihydroxy-2-(3,4-dihydroxyphenyl)chroman-3-yl 3,4,5-trihydroxybenzoate (Sheng Biao Wan; Di Chen; Q. Ping Dou and Tak Hang Chan. *Bioorganic & Medicinal Chemistry*, 2004, 12, 3521) afforded 25* with 93% yield. mp 105-107° C.; $[\alpha]_D=-14.5$ (c=1.2, CHCl$_3$); $^1$H NMR (CDCl$_3$, 400 MHz): δ 7.62 (s, 2H), 7.33 (d, J=1.2 Hz, 1H), 7.31 (A of AB, J=8.4 Hz, 1H), 7.20 (B of AB, J=8.4 Hz, 1H), 6.73 (d, J=2.0 Hz, 1H), 6.60 (d, J=2.0 Hz, 1H), 5.63 (bs, 1H), 5.20 (bs. 1H), 3.10 (A of ABq, J=18.0, 4.5 Hz, 1H), 3.00 (B of AB, J=18.0 Hz, 1H), 2.28-2.27 (m, 15H), 2.25 (s, 3H), 2.23 (s, 3H); $^{13}$C NMR (CDCl$_3$, 400 MHz): δ 168.8, 168.3, 167.9, 167.4, 166.2, 163.5, 154.9, 149.7, 143.3, 142.0, 141.9, 138.9, 135.3, 127.4, 124.3, 123.5, 122.2, 121.8, 109.4, 108.9, 108.0, 68.1, 25.9, 21.0, 20.7, 20.5, 20.1; HRMS (ESI) calcd for C$_{36}$H$_{32}$O$_{17}$Na (M+Na) 759.1537. found 759.1571.

(+)-(2R,3S)-5,7-dihydroxy-2-(4-hydroxyphenyl)chroman-3-yl 4-hydroxybenzoate tetraacetate (114)

Following the preparation procedure of 22*, the acetylation of 112 afforded 114 with 91% yield. mp 167-169° C.;

[α]$_D$=+3.2 (c=1.0, CHCl$_3$); $^1$H NMR (CDCl$_3$, 400 MHz): δ 7.94 (d, J=8.7 Hz, 2H), 7.42 (d, J=8.5 Hz, 2H), 7.14 (d, J=8.7 Hz, 2H), 7.09 (d, J=8.5 Hz, 2H), 6.69 (d, J=2.2 Hz, 2H), 6.61 (d, J=2.2 Hz, 2H), 5.53 (dd, J=11.5, 6.3 Hz, 1H), 5.31 (d, J=6.3 Hz, 2H), 3.01 (A of ABq, J=16.7, 5.1 Hz, 1H), 2.81 (B of ABq, J=16.7, 6.3 Hz, 1H), 2.30 (s, 3H), 2.28 (s, 3H), 2.27 (s, 3H), 2.25 (s, 3H); $^{13}$C NMR (CDCl$_3$, 400 MHz): δ 169.1, 168.8, 168.7, 168.3, 164.7, 154.6, 154.5, 150.7, 149.8, 149.4, 134.8, 131.2, 127.5, 127.0, 121.8, 121.6, 110.2, 108.6, 107.6, 78.1, 69.1, 24.1, 21.0, 20.7; HRMS (ESI) calcd for C$_{30}$H$_{27}$O$_{11}$ (M+H) 563.1553. found 563.1567; and calcd for C$_{30}$H$_{26}$O$_{11}$Na (M+Na) 585.1373. found 585.1387.

(−)-(2R,3R)-5,7-dihydroxy-2-(4-hydroxyphenyl) chroman-3-yl 4-hydroxybenzoate tetraacetate (21*)

Following the preparation procedure of 22*, the acetylation of 10 afforded 21* with 89% yield. mp 144-145° C.; [α]$_D$=−30.7 (c=2.5, CHCl$_3$); $^1$H NMR (CDCl$_3$, 400 MHz): δ 7.90 (d, J=8.7 Hz, 2H), 7.49 (d, J=8.5 Hz, 2H), 7.10 (d, J=8.5 Hz, 2H), 7.08 (d, J=8.7 Hz, 2H), 6.74 (d, J=2.2 Hz, 2H), 6.59 (d, J=2.2 Hz, 2H), 5.64 (bs, 1H), 5.22 (s, 1 H), 3.12 (A of ABq, J=17.7, 4.4 Hz, 1H), 3.02 (B of ABq, J=17.7, 1.8 Hz, 1H), 2.28 (s, 6H), 2.27 (s, 3H), 2.25 (s, 3H); $^{13}$C NMR (CDCl$_3$, 400 MHz): δ 169.1, 168.9, 168.7, 168.4, 164.8, 155.2, 154.4, 150.5, 149.7, 134.5, 131.2, 127.4, 126.9, 121.6, 109.7, 108.7, 108.0, 67.7, 26.2, 21.0, 20.7; HRMS (ESI) calcd for C$_{30}$H$_{26}$O$_{11}$Na (M+Na) 585.1373. found 585.1371.

(+)-(2R,3S)-5,7-dihydroxy-2-(4-hydroxyphenyl) chroman-3-yl 3,4,5-trihydroxybenzoate hexaacetate (16*)

Following the preparation procedure of 22*, the acetylation of (+)-(2R,3S)-5,7-dihydroxy-2-(4-hydroxyphenyl) chroman-3-yl 3,4,5-trihydroxybenzoate (Sheng Biao Wan; Tak Hang Chan. *Tetrahedron*, 2004, 60, 8207) afforded 16* with 93% yield. mp 96-98° C.; [α]$_D$=+17.7 (c=1.0, CHCl$_3$); $^1$H NMR (CDCl$_3$, 400 MHz): δ 7.66 (s, 2 H), 7.41 (d, J=8.5 Hz, 2H), 7.10 (d, J=8.5 Hz, 2H), 6.68 (d, J=2.2 Hz, 2H), 6.62 (d, J=2.2 Hz, 2 H), 5.51 (dd, J=12.2, 6.7 Hz, 1H), 5.26 (d, J=6.7 Hz, 1H), 3.02 (A of ABq, J=16.7, 5.3 Hz, 1 H), 2.81 (B of ABq, J=16.7, 6.6 Hz, 1H), 2.30 (s, 6H), 2.29 (s, 3H), 2.28 (s, 3H), 2.27 (s, 6H); $^{13}$C NMR (CDCl$_3$, 400 MHz): δ 169.1, 168.8, 168.3, 167.5, 166.2, 163.3, 154.5, 150.7, 149.9, 149.4, 143.4, 138.9, 134.5, 127.5, 122.2, 121.8, 110.1, 108.7, 107.7, 78.0, 69.8, 24.3, 21.0, 20.7, 20.5, 20.1; HRMS calcd for C$_{34}$H$_{30}$O$_{15}$Na (M+Na) 701.1482. found 701.1490.

(−)-(2R,3R)-5,7-dihydroxy-2-(4-hydroxyphenyl) chroman-3-yl 3,4,5-trihydroxybenzoate hexaacetate (19*)

Following the preparation procedure of 22*, the acetylation of (−)-(2R,3R)-5,7-dihydroxy-2-(4-hydroxyphenyl) chroman-3-yl 3,4,5-trihydroxybenzoate (Sheng Biao Wan; Tak Hang Chan. *Tetrahedron*, 2004, 60, 8207) afforded 19* with 91% yield. mp 152-154° C.; [α]$_D$=−35.5 (c=2.5, CHCl$_3$); $^1$H NMR (CDCl$_3$, 400 MHz): δ 7.62 (s, 2H), 7.46 (d, J=8.5 Hz, 2H), 7.11 (d, J=8.5 Hz, 2H), 6.73 (d, J=2.1 Hz, 1H), 6.60 (d, J=2.1 Hz, 1H), 5.60 (bs, 1 H), 5.21 (s, 1H), 3.10 (A of ABq, J=17.8, 4.5 Hz, 1H), 3.00 (B of ABq, J=17.8, 1.8 Hz, 1H), 2.28-2.26 (m, 18H); $^{13}$C NMR (CDCl$_3$, 400 MHz): δ 169.1, 168.8, 168.3, 167.4, 166.2, 163.5, 155.1, 150.6, 149.7, 143.3, 138.8, 134.2, 127.5, 127.4, 122.2, 121.7, 109.5, 108.8, 108.0, 77.2, 68.3, 26.0, 21.0, 20.7, 20.5, 20.1; HRMS (ESI) calcd for C$_{34}$H$_{30}$O$_{15}$Na (M+Na) 701.1482. found 701.1452.

(E)-3-[2,4-Bis(benzyloxy)-6-hydroxyphenyl]-1-phenyl-propene (#a)

Following the procedure in the literature (Li, L.; Chan, T. H. *Org. Lett.* 2001, 5, 739), cinnamyl alcohol was reacted with 3,5-dibenzyloxyphenol to yield (#a) as a white solid (62% yield); mp 76-78° C.; $^1$H NMR (CDCl$_3$, 400 MHz) δ 7.40-7.24 (m, 15H), 6.48 (A of AB, J=15.9 Hz, 1H), 6.35 (B of ABt, J=15.9, 5.5 HZ, 1H), 6.27 (d, J=2.1 Hz, 1H), 6.16 (d, J=2.1 Hz, 1H), 5.07 (s, 1H), 5.02 (s, 2H), 4.99 (s, 2H), 3.59-3.57 (d, J=5.5 Hz, 2 H); $^{13}$C NMR (CDCl$_3$, 400 MHz) δ 158.5, 157.6, 155.4, 137.0, 136.8, 136.6, 130.2, 128.3, 128.2, 128.1, 128.0, 127.8, 127.6, 127.3, 127.0, 126.8, 125.8, 106.6, 94.8, 93.4, 70.1, 69.9, 26.2; HRMS (ESI) calcd for C$_{29}$H$_{26}$O$_3$Na (M+Na) 445.1780. found 445.1793.

(+)-(1S,2S)-3-[2,4-Bis(benzyloxy)-6-hydroxyphenyl]-1-phenylpropane-1,2-diol ((+)-#b)

Following the procedure in the literature (Li, L.; Chan, T. H. *Org. Lett.* 2001, 5, 739), but with (#a) as starting material and AD-mix-α as dihydroxylation regent, (+)-#b was obtained (47% yield) as a white solid; mp 121-123° C.; [α]$_D$=+4.7 (c=0.6, CHCl$_3$); $^1$H NMR (CDCl$_3$, 400 MHz) δ 7.38-7.19 (m, 13H), 7.10 (m, 2H), 6.23 (d, J=2.3 Hz, 1 H), 6.17 (d, J=2.3 Hz, 1H), 4.94 (s, 2H), 4.82 (AB, J=11.7 Hz, 2H), 4.47 (d, J=6.6 Hz, 1 H), 3.97 (m, 1 H), 2.88 (A of ABt, J=14.6, 3.6 Hz, 1H), 2.72 (b of ABt, J=14.6, 8.6 Hz, 1H); $^{13}$C NMR (CDCl$_3$, 400 MHz): δ 158.8, 157.6, 157.0, 140.0, 136.6, 136.5, 128.3, 128.2, 128.1, 128.0, 127.7, 127.4, 127.3, 126.8, 126.5, 105.9, 95.6, 93.2, 76.6, 69.8, 69.7, 26.2; HRMS (ESI) calcd for C$_{29}$H$_{28}$O$_5$Na (M+Na) 479.1834. found 479.1841.

(+)-(2S,3S)-cis-5,7-Bis(benzyloxy)-2-phenylchroman-3-ol ((+)-#c)

Following the procedure in the literature (Li, L.; Chan, T. H. *Org. Lett.* 2001, 5, 739), but with (+)-#b as starting material, (+)-#c was obtained (47% yield) as a white solid; mp 60-62° C.; [α]$_D$=+0.9 (c=1.0, ethyl acetate); $^1$H NMR (CDCl$_3$, 400 MHz) δ 7.49-7.30 (m, 15H), 6.29 d, J=2.2 Hz, 1H), 6.27 (d, J=2.2 Hz, 1H), 5.02 (bs, 1H), 4.99 (s, 4 H), 4.25 (bs, 1H), 3.03 (A of ABt, J=17.2, 1.4 Hz, 1H), 2.96 (B of ABt, J=17.2, 4.2 Hz, 1H); $^{13}$C NMR (CDCl$_3$, 400 MHz): δ 158.7, 158.2, 155.2, 138.1, 136.9, 136.8, 128.5, 128.4, 128.0, 127.9, 127.8, 127.4, 127.1, 126.2, 100.9, 94.6, 94.0, 78.6, 70.0, 69.8, 66.2, 28.2; HRMS (ESI) calcd for C$_{29}$H$_{26}$O$_4$Na (M+Na) 461.1729. found 461.1741.

(+)-(2S,3S)-5,7-dihydroxy-2-phenylchroman-3-yl 3,4,5-trihydroxybenzoate ((+)-15)

Following the procedure in the literature (Li, L.; Chan, T. H. *Org. Lett.* 2001, 5, 739), but with (+)-#c as starting material, compound (+)-15 was obtained (90% yield): mp 258-260° C. (decomposed); [α]$_D$=+13.9 (c=3.5, ethanol); $^1$H NMR (acetone-d$_6$, 400 MHz): δ 7.73-7.71 (m, 2H), 7.49-7.45 (m, 2H), 7.41-7.38 (m. 1H), 7.17 (s, 2 H), 6.24 (d, J=2.2 Hz, 1 H), 6.23 (d, J=2.2 Hz, 1H), 5.76 (bs, 1H), 5.44 (bs, 1H), 3.27 (A of ABt, J=17.4, 4.5 Hz, 1 H), 3.14 (B of ABt, J=17.4, 1.4 Hz, 1H); $^{13}$C NMR (acetone-d$_6$, 400 MHz): δ 164.7, 156.6, 156.3, 155.7, 144.7, 138.5, 137.6, 127.6, 127.3, 126.3, 120.4, 108.7, 97.7, 95.4, 94.6, 77.0, 68.1, 25.3; HRMS (ESI) calcd for $C_{22}H_{18}O_8Na$ (M+Na) 433.0899. found 433.0904.

2-Benzyl-3,5-bis(benzyloxy)phenol (#d)

Ethanethiol (10 g, 216 mmol) was added dropwise to a stirred suspension of sodium hydride (60% dispersion in mineral oil, 2.4 g, 100 mmol) in dry DMF (120 mL) at 0° C. After 1 h, 1,3,5-tribenzyloxybezene (24 g, 60 mmol) was added in 10 batches and the mixture was heated to 150° C. for 1.5 h. After the reaction was cooled, water (500 mL) was added and the mixture was extracted with EtOAc. The combined organic layers were dried ($MgSO_4$) and evaporated. The residue was purified by flash chromatography on silica gel (benzene) to give 3,5-dibenzyloxyphenol as white solid (11%) after recrystallization from carbon tetrachloride and product #d as white solid (56%) after recrystallization from EtOAc and hexane. Compound #d was identified by mp 107-109° C.; $^1$H NMR ($CDCl_3$, 400 MHz) δ 7.36-7.23 (m, 15H), 6.25 (d, J=2.2 Hz, 1H), 6.07 (d, J=2.2 Hz, 1H), 4.96 (s, 2H), 4.92 (s, 2 H), 3.99 (s, 2H); $^{13}$C NMR ($CDCl_3$, 400 MHz) δ 158.4, 157.9, 154.9, 140.7, 136.7, 136.6, 128.4, 128.2, 128.1, 127.8, 127.5, 127.3, 127.0, 125.6, 108.5, 94.7, 93.3, 70.2, 69.9, 28.3; HRMS (ESI) calcd for $C_{27}H_{24}O_3Na$ (M+Na) 419.1623. found 419.1645.

(E)-3-[2,4-Bis(benzyloxy)-5-benzyl-6-hydroxyphenyl]-1-[3,4-bis(beznyloxy)phenyl]-propene (#e)

At rt under an $N_2$ atmosphere, 25% $H_2SO_4/SiO_2$ (1.6 g, 4 mmol) was added in one batch to the stirred mixture of 2-benzyl-3,5-bis(benzyloxy)phenol (3.96 g, 10 mmol) and (E)-3,4-bis(benzyloxy)cinnamyl alcohol (3.46 g, 10 mmol) in dry $CH_2Cl_2$ (80 mL). The resulting mixture was stirred at rt overnight. After filtration and evaporation, the residue was purified by column chromatography on silica gel (EtOAc/n-hexane=1/7 v/v) and recrystalized from EtOAc and n-hexane to give a white solid, (3.4 g, 46.0% yield): mp 93-95° C.; $^1$H NMR ($CDCl_3$, 400 MHz) δ 7.41-7.22 (m, 30H), 6.92 (s, 1H), 6.79 (s, 1H), 6.78 (d, J=4.0 Hz, 1 H), 6.35 (A of AB, J=15.8 Hz, 1H), 6.26 (s, 1H), 6.13-6.07 (B of ABt, J=15.8, 5.0 Hz, 1H), 5.08 (s, 2H), 5.07 (s, 2H), 4.99 (s, 4H), 4.02 (s, 2H), 3.55 (d, J=5.0 Hz, 2H); $^{13}$C NMR ($CDCl_3$, 400 MHz) δ 156.1, 155.6, 154.0, 148.9, 148.2, 141.1, 137.2, 137.1, 131.0, 130.1, 128.5, 128.4, 128.2, 127.8, 127.7, 127.6, 127.3, 127.2, 127.1, 126.5, 125.7, 119.7, 114.9, 112.4, 109.6, 107.3, 91.4, 71.1, 70.5, 70.3, 28.8, 26.6; HRMS (ESI): calcd for $C_{50}H_{44}O_5Na$ (M+Na) 747.3086. found 747.3096.

(−)-(1R,2R)-3-[2,4-Bis(benzyloxy)-5-benzyl-6-hydroxy-phenyl]-1-[3,4-bis(benzyloxy)phenyl]propane-1,2-diol ((−)-#f)

The propene (#e) (3.4 g, 4.6 mmol) was dissolved in dry DMF (30 mL), and to this solution imidazole (1.03 g, 15.2 mmol) and TBSCl (1.2 g, 7.8 mmol) were added successively. The resulting mixture was stirred at rt for 3 days, and then saturated $Na_2CO_3$ solution was added to quench the reaction. The mixture was extracted with EtOAc. The organic layers were combined, dried ($MgSO_4$), and evaporated. The residue was purified by flash chromatograph on silica gel (n-hexane and EtOAc=9/1 v/v) to afford [3,5-bis(benzyloxy)-6-benzyl-2-[3-[3,4-bis(benzy loxy)phenyl]allyl]phenoxy]-tert-butyldimethylsilane. This material was used in next step without further purification.

AD-mix-β (13.0 g) and methanesulfonamide (0.87 g) were dissolved in a solvent mixture of t-BuOH (50 mL) and $H_2O$ (50 mL). The resulting mixture was stirred at rt for 5 min, then the mixture was cooled to 0° C. and a solution of [3,5-bis(benzyloxy)-6-benzyl-2-[3-[3,4-bis(benzyloxy)phenyl]-allyl]phenoxy]-tert-butyldimethylsilane in dichloromethane (50 mL) was added. After the mixture had been stirred overnight, two more batches of AD-mix-β (13.0 g each) and methanesulfonamide (0.87 g each) were added in each 24 h intervals. After another 24 h of stirring at 0° C., TLC showed that the reaction was completed. Then a 10% $Na_2S_2O_3$ solution was added to quench the reaction. The mixture was extracted with EtOAc. The organic phases were combined, dried ($MgSO_4$) and evaporated. The residue was purified by flash chromatograph on silica gel (n-hexane and EtOAc=4/1 v/v) to afford [3,5-bis(benzyloxy)-6-benzyl-2-[3-[3,4-bis (benzyloxy)phenyl]-1,2-dihydroxyl-propyl]phenoxy]-tert-butyldimethylsilane. The resulting compound was dissolved in THF (75 mL), and TBAF (10 mL, 1 M in THF) was added. The resulting mixture was stirred at rt for 4 h, and saturated $NaHCO_3$ solution was added. The mixture was extracted with EtOAc, and the organic layers were combined, dried (MgSO4) and evaporated. The residue was purified by flash chromatography on silica gel (EtOAc/hexane=1/2 v/v) and then recrystallized from EtOAc and hexane to give a white solid (2.4 g, 67% yield) (−)-#f: mp 157-159° C.; $[α]_D$=−5.5 (c=1.1, $CHCl_3$); $^1$H NMR ($CDCl_3$, 400 MHz) δ 7.41-7.09 (m, 25H), 6.91 (d, J=1.6 Hz, 1H), 6.77 (m, 2H), 6.17 (s, 1H), 5.06 (s, 4H), 4.98 (s, 2H), 4.82 (AB, J=11.9 Hz, 2 H), 4.42 (d, J=6.6 Hz, 1H), 4.05 (s, 2H), 3.91 (b, 1H), 2.93 (A of ABt, J=14.5, 3.2 Hz, 1 H), 2.72 (B of ABt, 14.5, 8.5 Hz, 1H); $^{13}$C NMR ($CDCl_3$, 400 MHz) δ 156.4, 155.6, 155.3, 148.9, 148.8, 142.1, 137.2, 137.1, 137.0, 133.5, 128.6, 128.5, 128.4, 128.0, 127.8, 127.7, 127.6, 127.3, 127.2, 127.1, 126.7, 125.3, 119.9, 114.5, 113.6, 112.1, 111.2, 106.7, 90.9, 77.2, 76.7, 71.1, 70.9, 70.3, 70.2, 29.1, 26.8; HRMS (ESI) calcd for $C_{50}H_{46}O_7Na$ (M+Na) 781.3141. found 781.3110.

(−)-(2S,3R)-trans-5,7-Bis(benzyloxy)-8-benzyl-2-[3,4-bis-(benzyloxy)phenyl]chroman-3-ol ((−)-#g)

To a suspension of (−)-#f (2.4 g, 3.1 mmol) in 1,2-dichloroethane (50 mL) was added triethyl orthoformate (1 mL), followed by PPTS (450 mg, 1.8 mmol). The mixture was stirred at rt for 20 min until the solid dissolved. The mixture was then heated to 55° C. for 5 h until TLC showed the reaction had been completed. After evaporation of the solvent, the residue was dissolved in DME (30 mL) and MeOH (30 ml), $K_2CO_3$ (450 mg) was added. The mixture was stirred at rt overnight. After evaporation of the solvent, the residue was purified by flash chromatography on silica gel (EtOAc/hexane, 1/3 v/v) to afford the desired product as white solid (1.8 g, 77% yield): mp 145-146° C.; $[α]_D$=−20.1 (c=1.3, $CHCl_3$); $^1$H NMR ($CDCl_3$, 400 MHz) δ 7.42-7.15 (m, 25H), 6.93 (d, J=1.6 Hz, 1H), 6.88 (A of AB, J=8.3 Hz, 1H), 6.82 (B of ABt, J=8.3, 1.6 Hz, 1H), 6.24 (s, 1H), 5.13 (s, 2H), 5.02 (s, 2 H), 5.00 (s, 2 H), 4.98 (s, 2H), 4.63 (d, J=8.1 Hz, 1H), 4.04 (AB, J=14.2 Hz, 2H), 3.86 (m, 1 H), 3.10 (A of ABt, J=5.6, 16.4 Hz, 1H), 2.67 (B of ABt, J=9.0, 16.4 Hz, 1H); $^{13}$C NMR ($CDCl_3$, 400 MHz) δ 155.8, 155.5, 152.9, 148.9, 148.8, 142.2, 137.2, 137.1, 137.0, 136.9, 131.2, 128.7, 128.5, 128.4, 128.3, 127.9, 127.8, 127.7, 127.4, 127.2, 127.1, 127.0, 125.2, 120.2, 114.5, 113.2, 110.2, 102.4, 91.1, 81.2, 71.1, 70.9, 70.4, 69.9, 68.2, 28.6, 27.6. HRMS (ESI) calcd for $C_{50}H_{44}O_6Na$ (M+Na) 763.3036. found 763.3032.

(+)-(2R)-5,7-Bis(benzyloxy)-8-benzyl-2-[3,4-bis (benzyl-oxy)-phenyl]chroman-3-one ((−)-#h))

Dess-Martin periodinane (6.3 mL, 15% g/mL in $CH_2Cl_2$, 2.2 mmol) was added in one batch to a stirred solution of (−)-#g (900 mg, 1.2 mmol) in CH$_2$Cl$_2$ (30 mL) under an N$_2$ atmosphere. The mixture was stirred at rt for about 2 h till TLC showed the absence of starting marterial. Subsequently, saturated NaHCO$_3$ solution (15 mL) and 10% Na$_2$S$_2$O$_3$ aqueous solution (15 mL) were added to quench the reaction. The organic layer was separated, and the aqueous layer was extracted with CH$_2$Cl$_2$. The combined organic phases were dried (MgSO$_4$) and evaporated. The residue was purified by flash chromatography on silica gel (benzene) and then recrystallized in CHCl$_3$ and ether to afford the desired compound (770 mg, 86%): mp 143-145° C., [α]$_D$=−17.1 (c=1.1, CHCl$_3$); $^1$H NMR (CDCl$_3$, 400 MHz): δ 7.43-7.07 (m, 25H), 6.89 (s, 1H), 6.84 (AB, J=8.5 Hz, 2 H), 6.33 (s, 1H), 5.13-5.04 (m, 6H), 5.02 (s, 1H), 4.99 (s, 2H), 4.05 (AB J=14.2 Hz, 2 H), 3.67 (AB, J=20.8 Hz, 2H); $^{13}$C NMR (CDCl$_3$, 400 MHz) δ 205.8, 156.5, 154.8, 152.5, 149.0, 148.7, 141.7, 137.1, 136.9, 136.8, 136.5, 128.6, 128.5, 128.4, 128.1, 128.0, 127.8, 127.7, 127.3, 127.1, 125.4, 120.0, 114.5, 113.2, 111.9, 102.4, 92.6, 82.9, 71.0, 70.5, 70.2, 34.0, 28.8; HRMS (ESI) calcd for C$_{50}$H$_{42}$O$_6$Na (M+Na) 761.2879. found 761.2843.

(+)-(2S,3S)-cis-5,7-Bis(benzyloxy)-8-benzyl-2-[3,4-bis-(benzyloxy)phenyl]chroman-3-ol ((+)-#i)

Under an N$_2$ atmosphere, the ketone (−)-#h (700 mg, 0.95 mmol) was dissolved in dry THF (15 mL), and the solution was cooled to −78° C. Then L-selectride (1.5 mL, 1 M solution in THF, 1.5 mmol) was added dropwise. The resulting solution was stirred at −78° C. for 8 h. When TLC showed the reaction was completed, saturated NaHCO$_3$ aqueous solution (10 mL) was added to quench the reaction. The organic layer was separated and the aqueous layer was extracted with EtOAc. The combined organic phases were dried (MgSO$_4$) and evaporated. The residue was purified by flash chromatography on silca gel (5% EtOAC/benzene) and then recrystalized with ethanol and EtOAC to afford the desired product (630 mg, 90%) as a white solid: mp 129-131° C., [α]$_D$=+5.3 (c=1.2, CHCl$_3$); $^1$H NMR (CDCl$_3$, 400 MHz): δ 7.44-7.07 (m, 25H), 7.05 (s, 1H), 6.93 (AB, J=8.4 Hz, 2 H), 6.26 (s, 1 H), 5.15 (s, 2H), 5.02 (s, 2H), 5.00 (s, 4H), 4.92 (bs, 1H), 4.20 (bs, 1 H), 4.10 (AB, J=14.5 Hz, 2H), 3.07 (A of AB, J=17.2 Hz, 1H), 2.92 (B of ABt, J=17.2, 4.2 Hz, 1H); $^{13}$C NMR (CDCl$_3$, 400 MHz): δ 156.2, 155.9, 152.8, 148.9, 148.5, 142.1, 137.2, 137.1, 137.0, 131.6, 128.5, 128.4, 128.0, 127.8, 127.7, 127.4, 127.2, 125.2, 118.9, 114.9, 112.9, 110.2, 101.1, 91.4, 78.0, 71.2, 71.0, 70.5, 70.0, 66.1, 28.6, 28.2; HRMS (ESI) calcd for C$_{50}$H$_{44}$O$_6$Na (M+Na) 763.3036 found 763.3024.

(+)-(2S,3S)-5,7-Bis(benzyloxy)-8-benzyl-2-[3,4-bis-(benzyloxy)-phenyl]chroman-3-yl 3,4,5-tris(benzyloxy)-benzoate ((+)-#j)

Under an N$_2$ atmosphere, a solution of 3,4,5-tris(benzyloxy)benzoic acid (170 mg, 0.39 mmol) was refluxed with oxally chloride (1 mL) in dry CH$_2$Cl$_2$ (10 mL) and one drop of DMF for 3 h. The excess oxally chloride and solvent were removed by distillation and the residue was dried under vacuum for 3 h and dissolved in CH$_2$Cl$_2$ (2 mL). This solution was added dropwise to a solution of (+)-#i (150 mg, 0.20 mmol) and DMAP (75 mg, 0.62 mmol) in CH$_2$Cl$_2$ (15 mL) at 0° C. The mixture was stirred at rt overnight, then saturated NaHCO$_3$ aqueous solution was added. The organic layer was separated, and the aqueous layer was extracted with CH$_2$Cl$_2$. The organic phases were combined, dried (MgSO$_4$) and evaporated. The residue was purified by flash chromatography on silica gel (5% EtOAc/benzene) to afford the desired compound (215 mg, 91%). Recrystallization in CHCl$_3$ and ether gave a white powder: mp 52-54° C.; [α]$_D$=+37.5 (c=1.0, CHCl$_3$); $^1$H NMR (CDCl$_3$, 400 MHz): δ 7.39-7.10 (m, 42H), 6.99 (t, J=7.4 Hz, 1H), 6.93 (AB, J=8.3 Hz, 2H), 6.31 (s, 1H)<5.65 (bs, 1H), 5.13 (bs, 1H), 5.07 (s, 2H), 5.02 (s, 4H), 5.00 (s, 2 H), 4.92 (s, 4H), 4.83 (AB, J=11.8 Hz, 2H), 4.11 (s, 1H), 3.15 (bs, 1H); $^{13}$C NMR (CDCl$_3$, 400 MHz): δ 165.2, 156.0, 155.9, 153.2, 152.3, 148.8, 148.6, 142.6, 142.2, 137.4, 137.2, 137.0, 136.5, 131.4, 128.7, 128.6, 128.5, 128.4, 128.2, 128.0, 127.9, 127.7, 127.3, 127.2, 125.4, 125.1, 119.4, 114.6, 113.2, 110.3, 109.2, 101.0, 91.2, 75.1, 71.1, 70.5, 70.0, 68.6, 28.7, 26.2; HRMS (ESI) calcd for C$_{78}$H$_{66}$O$_{10}$Na (M+Na) 1185.4554. found 1185.4542.

(−)-(2S,3R)-5,7-Bis(benzyloxy)-8-benzyl-2-[3,4-bis-(benzyloxy)-phenyl]chroman-3-yl 3,4,5-tris(benzyloxy)-benzoate ((−)-#k)

Following the procedure used for the preparation of (−)-#j but with (−)-#g as starting material, (−)-(2S,3R)-5,7-bis(benzyloxy)-8-benzyl-2-[3,4-bis(benzyl-oxy)phenyl]-chroman-3-yl 3,4,5-tris(benzyloxy)benzoate was obtained (90% yield) as a white solid: mp 103-105° C., [α]$_D$=−9.8 (c=1.3, CHCl$_3$); $^1$H NMR (CDCl$_3$, 400 MHz): δ 7.37-7.11 (m, 42 H), 6.90 (s, 1H), 6.77 (m, 2H), 6.27 (s, 1H), 5.42 (m, 1H), 5.18 (d, J=6.3 Hz, 1H), 5.06 (s, 4H), 5.05-4.99 (m, 4H), 4.97 (s, 4H), 4.88 (s, 2H), 4.12 (AB, J=14.1 Hz, 2H), 3.01 (a of ABt, J=16.8, 5.0 Hz, 1H), 2.89 (B of ABt, J=16.8, 6.4 Hz, 1H); $^{13}$C NMR (CDCl$_3$, 400 MHz): δ 156.0, 155.9, 155.4, 152.5, 152.3, 148.8, 148.6, 142.3, 142.1, 137.3, 137.1, 137.0, 136.9, 136.5, 131.3, 128.7, 128.5, 128.4, 128.3, 128.1, 128.0, 127.9, 127.8, 127.7, 127.5, 127.3, 127.2, 127.1, 125.3, 124.9, 114.6, 112.8, 110.2, 108.9, 101.5, 91.0, 78.0, 75.0, 71.2, 71.1, 71.0, 70.4, 70.0, 69.9, 28.6, 24.0; HRMS (ESI) calcd for C$_{78}$H$_{66}$O$_{10}$Na (M+Na) 1185.4554. found 1185.4573.

(+)-(2S,3S)-5,7-dihydroxy-8-benzyl-2-[3,4-dihydroxy-phenyl]chroman-3-yl 3,4,5-trihydroxybenzoate ((+)-#I)

Under an H$_2$ atmosphere, Pd(OH)$_2$/C (20%, 400 mg) was added to a solution of (+)-#j (200 mg, 0.17 mmol) in a sovlent mixture of THF/MeOH (1:1 v/v, 20 mL). The reaction mixture was stirred at rt under H$_2$ for 6 h when TLC showed that the reaction was completed. The reaction mixture was filtered to remove the catalyst. The filtrate was evaporated, and the residue was rapidly purified by flash chromatograph on silica gel (10% MeOH/CH$_2$Cl$_2$, then 20% MeOH/CH$_2$Cl$_2$) to afford (+)-8-benzylcatechin gallate ((+)-#1) (82 mg, 90% yield): mp 243-245° C. (decomposed); [α]$_D$=+123 (c=1.8, acetone); $^1$H NMR (acetone-d$_6$, 400 MHz): δ 7.53 (d, J=7.4 Hz, 2H), 7.42 (t, J=7.6 Hz, 2H), 7.26-7.21 (m, 4H), 7.04 (AB, J=8.2 Hz, 2H), 6.31 (s, 1H), 5.75 (bs, 1H), 5.32 (bs, 1H), 4.22 (AB, J=14.3 Hz, 2H), 3.29 (a of ABt, J=17.4, 4.4 Hz, 1H), 3.17 (b of AB, J=17.4, 1H); $^{13}$C NMR (acetone-d$_6$, 400 MHz): δ 165.2, 154.2, 154.1, 153.6, 144.9, 144.6, 144.3, 142.6, 137.9, 130.6, 128.4, 127.8, 125.0, 120.9, 118.1, 114.7, 113.7, 109.1, 106.7, 98.0, 95.3, 77.1, 68.3, 25.9; HRMS (ESI) calcd for C$_{29}$H$_{24}$O$_{10}$Na (M+Na) 555.1267. found 555.1279.

(−)-(2S,3R)-5,7-dihydroxy-8-benzyl-2-[3,4-dihydroxy-phenyl]chroman-3-yl 3,4,5-trihydroxybenzoate ((−)-16)

Following the procedure for the preparation (+)-#I, but with (−)-#k as starting material, (−)-8-benzylcatechin gallate ((−)-16) was obtained (91% yield): mp 239-241° C. (decomposed); [α]$_D$=−35 (c=2.0, acetone); $^1$H NMR (acetone-d$_6$, 400 MHz): δ 7.44 (d, J=7.1 Hz, 2H), 7.33 (t, J=7.5 Hz, 2H), 7.23 (s, 2H), 7.21 (t, J=7.3 Hz, 1H), 6.92-6.86 (m, 2 H), 6.34 (s, 1H), 5.56 (m, 1H), 5.35 (d, J=6.2 Hz, 1H), 4.17 (AB, J=14.3 Hz, 2H), 3.12 (A of ABt, J=16.5, 5.2 HZ, 1H), 2.98 (b of ABt, J=16.5. 6.2 HZ, 1H); $^{13}$C NMR (acetone-$d_6$, 400 MHz): δ 165.0, 154.1, 153.7, 152.8, 144.9, 144.7, 144.6, 142.2, 137.8, 130.2, 128.3, 127.5, 124.8, 120.5, 117.9, 114.8, 113.2, 108.8, 106.2, 98.2, 95.1, 77.7, 69.4, 23.5; HRMS (ESI) calcd for $C_{29}H_{24}O_{10}Na$ 555.1267. found 555.1285.

Stability Tests of (−)-EGCG and 1

(−)-EGCG or 1 (0.1 mM) was incubated with RPMI 1640 culture medium at 37° C. At different time points, 15 µL of the medium was injected into an HPLC equipped with a C-18 reverse phase column (CAPCELL PAK C18 UG 120, Shiseido Co., Ltd., 4.6 mm i.d.×250 mm); flow rate, 1 mL/min; detection, UV 280 nm; for (−)-EGCG, time points were 0, 10, 20, 40, 60, 90, 120 minutes and the mobile phase, 20% aqueous acetonitrile and 0.01% TFA; for prodrug 1, time points were 0, 30, 60, 90, 120 minutes and mobile phase, 50% aqueous acetonitrile and 0.01% TFA.

Enzymatic Hydrolysis of 1

Lysis buffer (pH 5) (0.25 mL) was added to 2×106 Jurkat T cells. This could break the cell membrane of the cells and release the cytoplasmic enzymes. PBS (0.75 mL) was added which neutralized the medium to the optimum pH value (pH 7) for the enzymes. Prodrug 1 (0.25 mM) was added into the reaction mixture and incubated at 37° C. At different time points (0, 30, 60, 90, 120, 150, 180, 210, 240, 300 and 360 minutes), an aliquot (0.06 mL) of the reaction mixture was taken out, filtered and injected into the HPLC and analyzed as outlined above.

Hydrolysis of 1 in the Presence of Vitamin C in Culture Medium With or Without Lysates Compound 1 (35 µM) was incubated with dulbecco's modified eagle medium (DMEM) (1 mL containing 1.67 mg/mL vitamin C) at 37° C. At different time points, 10 µL of the solution was injected into an HPLC equipped with a C-18 reverse phase column; flow rate, 1 mL/min; detection, UV 280 nm; mobile phase, 0-8 minutes (20% aqueous acetonitrile and 0.016% TFA), 8-13 minutes (varying from 20% aqueous acetonitrile with 0.016% TFA to 60% aqueous acetonitrile with 0.008% TFA).

For the investigation of hydrolysis of 1 in the presence of lysates, same concentration of 1 was incubated with DMEM (2 mL containing 1.67 mg/mL vitamin C) in the presence of the lysates (5×105 breast cancer cells with 0.15 mL lysis buffer). At different time points, an aliquot (0.06 mL) of the reaction mixture was taken out, filtered, injected into the HPLC and analyzed as outlined above.

Cell Cultures

Human Jurkat T and LNCaP cells were cultured in RPMI supplemented with 10% (v/v) fetal bovine serum, 100 U/ml penicillin, and 100 µg/ml streptomycin. The non-transformed natural killer cells (YT line) were grown in RPMI medium containing with 10% (v1v) fetal bovine serum, 100 U/ml penicillin, 100 µg/ml streptomycin, 1 mM MEM sodium pyruvate, and 0.1 mM MEM nonessential amino acids solution. Human breast cancer MCF-7 cells, normal (WI-38) and simian virus-transformed (VA-13) human fibroblast cells were grown in Dulbecco's modified Eagle's mediums supplemented with 10% (v1v) fetal bovine serum, 100 U/ml penicillin, 100 pg/ml streptomycin. All cell cultures were maintained in a 5% $CO_2$ atmosphere at 37° C.

Cell Extract Preparation and Western Blotting

Whole cells extracts were prepared as described previously (An B, Goldfarb R H, Siman R, Dou Q P. Novel dipeptidyl proteasome inhibitors overcome Bcl-2 protective function and selectively accumulate the cyclin-dependent kinase inhibitor p27 and induce apoptosis in transformed, but not normal, human fibroblasts. Cell Death Differ 1998; 5: 1062-75.). Analysis of Bax, IKBa, p27, PAW, and ubiquitinated protein expression were performed using monoclonal or polyclonal antibodies according to previously reported protocols (An B et. al.).

Inhibition of Purified 20s Proteasome Activity by (−)-EGCG or Synthetic Tea Polyphenols Measurement of the chyrnotrypsin-like activity of the 20s proteasome was performed by incubating 0.5 µg of purified rabbit 20s proteasome with 40 µM fluorogenic peptide substrate, Suc-Leu-Leu-Val-Tyr-AMC, with or without various concentrations of natural and synthetic tea polyphenols as described previously (Nam S et. al.).

Inhibition of Proteasome Activity in Intact Cells by Natural/Synthetic Tea Polyphenols VA-13 or WI-38 cells were grown in 24 well plates (2 ml/well) to 70-80% confluency, followed by 24 h treatment with 25 pM (−)-EGCG, 2, or 2a. 40 pM Suc-Leu-Leu-Val-Tyr-AMC substrate was then added for 2.5 h at 37° C. and the chyrnotrypsin-like activity was measured as described above. Alternatively, cells were treated with each compound at 25 µM for 4 or 24 h, and harvested and lysed. Suc-Leu-Leu-Val-Tyr-AMC (40 µM) was then incubated with the prepared cell lysates for 2.5 h and the chymotrypsin-like activity was measured as described above.

Immunostaining of Apoptotic Cells with Anti-Cleaved PARP Conjugated to FITC

Immunostaining of apoptotic cells was performed by addition of a FITC-conjugated polyclonal antibody that recognizes cleaved poly(ADP-ribose) polymerase (PARP) and visualized on an Axiovert 2 5 (Zeiss; Thornwood, N.Y.) microscope. Cells were grown to about 80% confluency in 60 mm dishes. VA-13 cells were then treated with VP-16, 2, or 2a (25 µM) for 24 h. Following treatment, both suspension and adhering cells were collected and washed twice in PBS pH 7.4. The cells were washed between all steps listed below and all washes are 1 min duration with PBS. Cells were then fixed in ice-cold 70% ethanol, permeabilized in 0.1% Triton-X-100 and blocked for 30 min in 1% bovine serum albumin (BSA) at room temperature. Incubation with the primary FITC-conjugated-p85/PARP antibody was for 30 min at 4° C. in the dark with mild shaking. Cell suspension was then transferred to glass slides in the presence of Vector Shield mounting medium with DAPI. Images were captured using AxioVision 4.1 and adjusted using Adobe Photoshop 6.0 software. Cell death was quantified by counting the number of apoptotic cells over the total number of cells in the same field. Data are mean of duplicate experiments ±SD.

Trypan Blue Assay

Trypan blue assay was used to ascertain cell death in Jurkat T cells treated with natural and synthetic polyphenols as indicated. Apoptotic morphology was assessed using phase-contrast microscopy as described previously (Kazi A, Hill R, Long T E, Kuhn D J, Twos E, Dou Q P. Novel N-thiolated beta-lactam antibiotics selectively induce apoptosis in human tumor and transformed, but not normal or nontransformed, cells. Biochem Pharmacol 2004; 67:365-74; Kuhn D J, Smith D M, Pross S, Whiteside T L, Dou Q P. Overexpression of interleukin-2 receptor alpha in a human squamous cell carcinoma of the head and neck cell line is associated with increased proliferation, drug resistance, and transforming ability. J Cell Biochem 2003; 89:824-36).

MTT Assay

MTT was used to determine effects of polyphenols on overall proliferation of tumor cells. Human breast MCF-7 cells were plated in a 96 well plate and grown to 70-80% confluency, followed by addition of analogs for 24 h. MTT (1 mg/ml) in PBS was then added to wells and incubated at 37° C. for 4 hours to allow for complete cleavage of the tetrazolium salt by metabolically active cells. Next, the MTT was removed and 100 μl of DMSO was added and colorimetric analysis performed using a multilabel plate reader at 560 nm (Victor[3]; Perkin Elmer). Absorbance values plotted are the mean from triplicate experiments.

Soft Agar Assay

LNCaP cells ($2\times10^4$) were plated in soft agar on 6 well plates in the presence of (−)-EGCG or protected tea analogs (25 pM) or in DMSO (control) to determine cellular transformation activity as described previously (Kazi A et al).

Nuclear Staining

After each drug treatment, both detached and attached VA-13 and WI-38 cells were stained Hoechst 33342 to assess for apoptosis. Briefly, cells were washed 2× in PBS, fixed for 1 h with 70% ethanol at 4° C., washed 3× in PBS, and stained with 50 pM Hoechst for 30 min in the dark at room temperature. Detached cells were plated on a slide and attached cells were visualized on the plate with a fluorescent microscope at 10× or 40× resolution (Zeiss, Germany). Digital Scientific obtained images with AxioVision 4.1 and adjusted using Adobe Photoshop 6.0.

Induction of Caspase-3 Activity by Synthetic Tea Polyphenols

Cells were treated with each compound at 25 μM for 4 or 24 h, and then harvested and lysed. Ac-DEVD-AMC (40 μM) was added to the cell lysates for 2.5 h and the caspase-3 activity.

Results

Chemical Stability and Enzymatic Hydrolysis of Peracetate (−)-EGCG, 1

Figure 2:
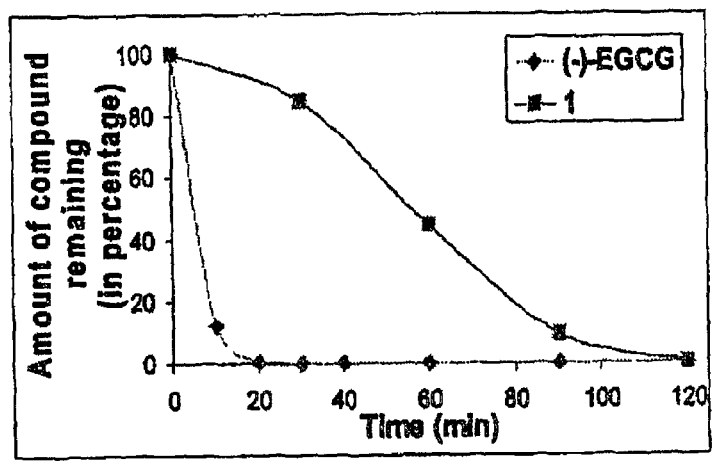
FIG. 2 shows the degradation curve of (−)-EGCG and 1.

The stability of 1 with (−)-EGCG in a culture medium (RMPI) is compared, which mimics the body fluid with a pH value around 8. (−)-EGCG or 1 at 0.1 mM was incubated in 1 mL RMPI at 37° C. at indicated times. At different time points, the medium was analyzed by HPLC for the amount of tested compound remaining. Degradation curves are shown in FIG. 2.

When (−)-EGCG was dissolved in the culture medium, it was found to degrade rapidly within 20 minutes, demonstrating the low stability of (−)-EGCG in the medium. Although 1 also degraded in the medium, as seen in FIG. 2, the rate of its degradation was much slower when compared with (−)-EGCG. 1 disappeared completely after 2 hours, indicating that it is 6 times more stable than (−)-EGCG in this medium. Therefore, peracetate protection of the phenol groups of (−)-EGCG assists in stabilizing 1 in culture (presumably physiological) conditions.

Figure 3:
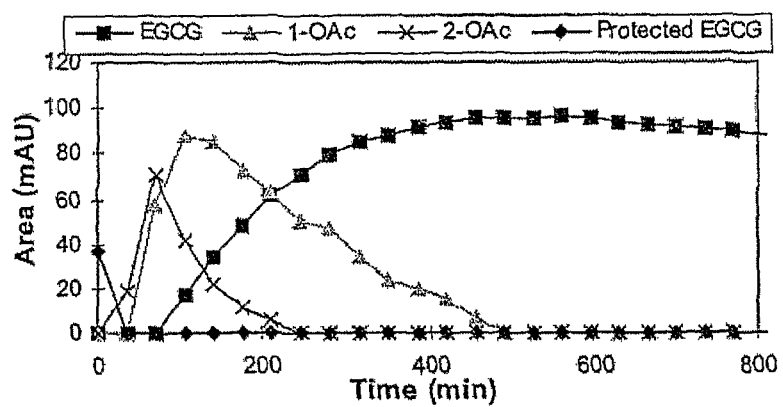
FIG. 3 shows the time-course results of peracetate EGCG (1) in culture medium with the presence of vitamin C (area vs time). Compound 1: ◆; compound A (di-acetate): x; compound B (mono-acetate): ▲; EGCG: ■.

In order to determine if 1 was hydrolysed to EGCG under the culture medium conditions, the experiment was repeated but now with added vitamin C (at 1.67 mg/mL) to prevent the rapid degradation of the generated EGCG. As 1 disappeared, a new peak A was observed by HPLC to increase and then decline in intensity with time. This was followed by the appearance of another peak B in the HPLC which also eventually declined. Finally, a peak in the HPLC identical in retention time to EGCG was observed to be formed. The time course results of these components were shown in FIG. 3. The identity of EGCG was confirmed by UV spectroscopy as well as mass spectrometry. Furthermore, mass spectrometric analyses of peaks A and B showed that they were the di-acetate and mono-acetate of EGCG respectively. These results suggested that compound 1 was first hydrolysed to the diacetate, then mono-acetate and eventually EGCG under the culture medium conditions.

Figure 4:
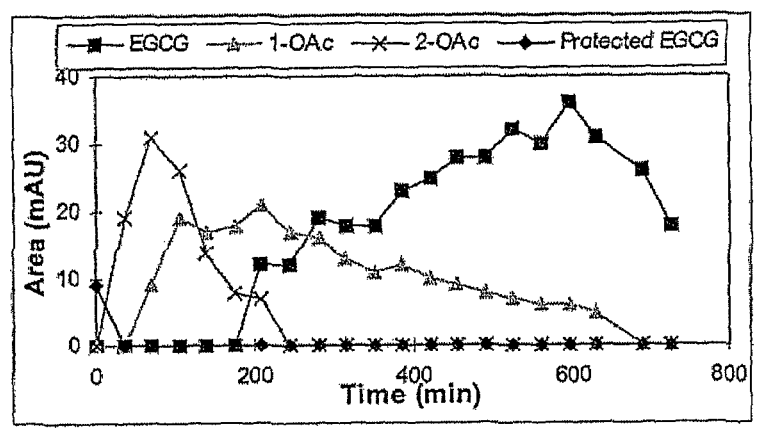
FIG. 4 shows the time-course results of peracetate EGCG (1) in culture medium with the presence of vitamin C with the addition of lysate (area vs time). Compound 1: ◆; compound A (di-acetate): x; compound B (mono-acetate): ▲; EGCG: ■.

The generation of (−)-EGCG from compound 1 under cellular conditions could be more clearly demonstrated by the addition of vitamin C to prevent the rapid disappearance of (−)-EGCG. In this case, we performed the experiment in medium with breast cancer cell lysate. HPLC analyses showed the disappearance of 1, together with the transient formation of A (the di-acetate), B (the mono-acetate) and then (−)-EGCG in a time-course results (FIG. 4) similar to FIG. 3. Therefore, it is believed that that in medium with the addition of lysate, compound 1 underwent hydrolysis forming the di-acetate of EGCG, then the mono-acetate, then EGCG, and eventually gallic acid. (Scheme 1)

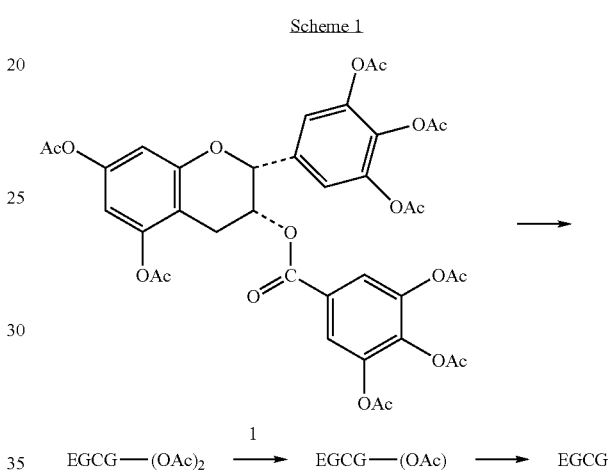

Scheme 1

Inhibition of the Proteasomal Activity In Vitro and In Vivo by 1 and (−)-EGCG

Figure 5:
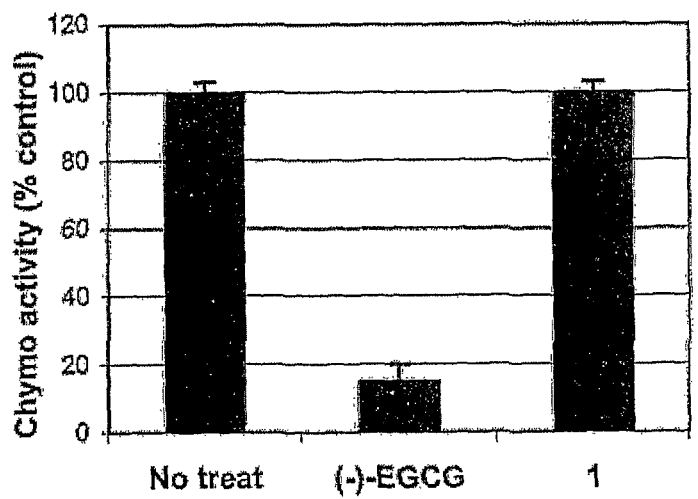
FIG. 5 shows the inhibition of the chymotrypsin-like activity of the purified 20S proteasome by 1 and (−)-EGCG.

If 1 is to function as the prodrug of (−)-EGCG, it should remain biologically inactive until de-acetylation inside the cell where it is converted into its parent compound. In order to test this hypothesis, proteasome activity was tested both in vitro and in intact Jurkat T cells with either 1 or (−)-EGCG (as a positive control). First, 1 and commercial (−)-EGCG were dissolved in DMSO and their effects on the chymotrypsin-like activity of purified 20S proteasomes were measured. At 10 μM, 1 was completely inactive in inhibiting the chymotrypsin-like activity of the purified 20S proteasome (FIG. 5). In contrast, (−)-EGCG at 10 μM inhibited 80-90% of the proteasomal chymotrypsin-like activity. Therefore, as predicted, 1 outside of a cellular system is not a proteasome inhibitor.

Figure 6A:
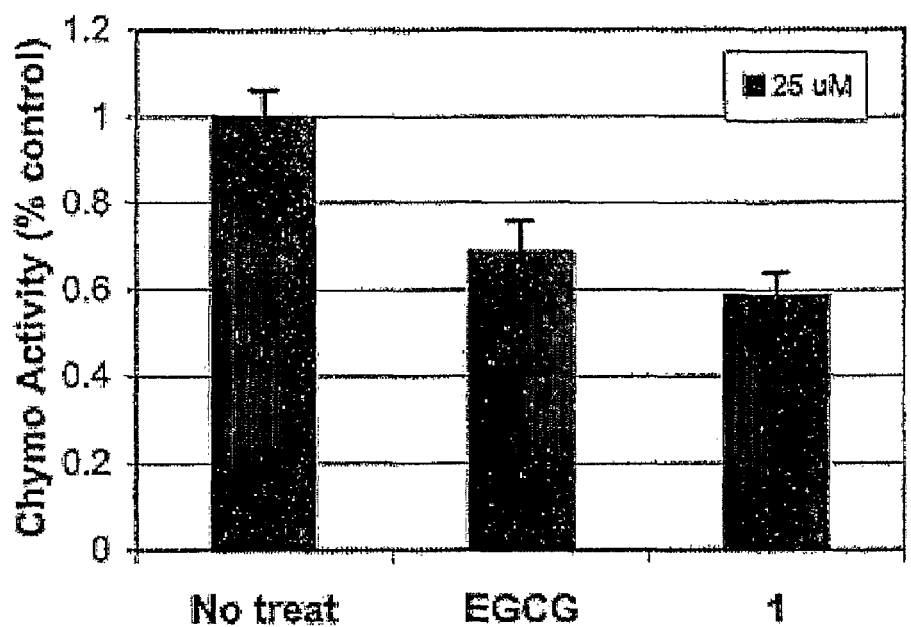
FIG. 6 shows (a) the inhibition of Proteasome Actvitiy by 1 and (−)-EGCG in vivo; (b) Western blot assay of ubiquitin after treatment with 1 and (−)-EGCG.
Figure 6B:

If 1 converts to (−)-EGCG inside the cells, proteasome inhibition in vivo should be detected. To examine this possibility, human Jurkat cells was treated with 25 μM of 1 or (−)-EGCG for 12 or 24 h, followed by measurement of proteasome activity by using a chymotrypsin-like specific fluorogenic substrate in intact cells (FIG. 6a) or Western blot for ubiquinated proteins (FIG. 6b). Treatment of Jurkat T cells with (−)-EGCG for 24 h inhibited proteasome activity by 31% versus 42% inhibition with 1 (FIG. 6a). To analyze the intracellular level of polyubiquitinated proteins, cells were lysed after 12 hours incubation and subjected to Western blotting. 1 showed comparable levels of ubiquitinated proteins to that of natural (−)-EGCG (FIG. 6b). Therefore, 1 is equally potent to, if not more potent than, (−)-EGCG in inhibiting the proteasomal activity in intact cells. On the other hand, even though 1 is six times more stable compared with EGCG, the potency of its biological activities in cells did not increase to a similar extent. It is possible that the amount of EGCG generated from 1, and thus its biological activity inside the cells depends on a combination of factors: the relative permeability of 1 into the cells, the amount of esterase enzymes and the amount of anti-oxidants that may be present in the cells at any time.

Figure 7:
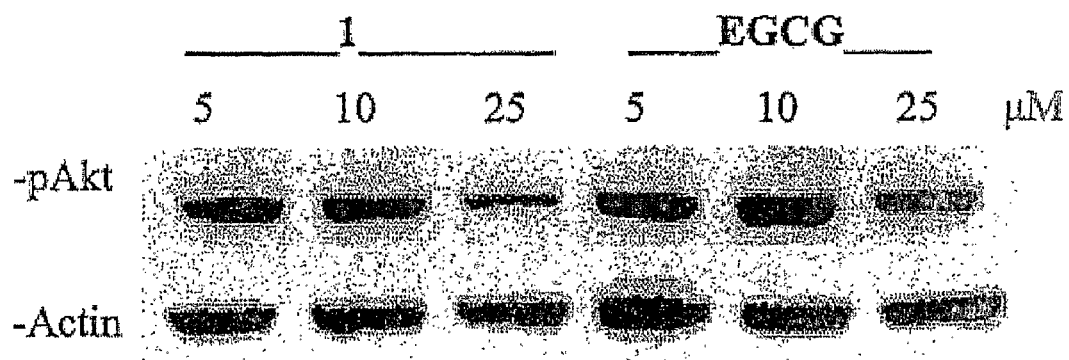
FIG. 7 shows the amount of p-Akt levels with 1 and (−)-EGCG treatment.

Dephosphorylation of Akt in Jurkat Cells by 1 and (−)-EGCG (−)-EGCG and 1 were incubated with Jurkat T cells for 24 h at 5, 10 and 25 µM, followed by Western blot analysis using a specific antibody to phosphorylated Akt (FIG. 7). (−)-EGCG at 25 µM was found to reduce the level of p-Akt by 32% compared to treatment with 1, which lead to a 73% decrease in activated Akt at 25 µM as indicated by densitometric analysis (FIG. 7). Actin was used as a loading control.

Cell Death Induced by 1 and (−)-EGCG

Figure 8:
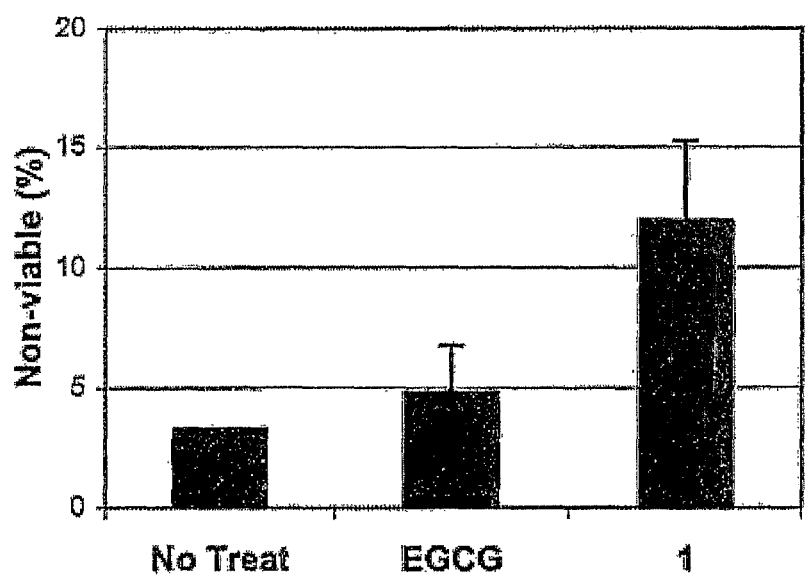
FIG. 8 shows the cell viability in Jurkat cells treated with 1 and (−)-EGCG.

The abilities of (−)-EGCG and 1 to induce cell death in Jurkat T cells treated with 10 µM for 24 h are also accessed. While (−)-EGCG had a minimal effect on cell death (5%), 1 was capable of inducing up to 15% cell death at that concentration (FIG. 8). Therefore, the greater abilities of 1 to inhibit cellular proteasome activity (FIG. 6) and to inactivate Akt (FIG. 7) are associated with its increased cell death-inducing activity (FIG. 8).

Acetylated Synthetic Tea Polyphenols Do Not Inhibit the Purified 20s Proteasome Activity Up to 25 µM of all protected and unprotected compounds were incubated with a purified 20s proteasome and a fluorogenic substrate for chymotrypsin activity for 30 min. The half-maximal inhibitory concentration or $IC_{50}$ was then determined. (−)-EGCG showed to be the most potent with an $IC_{50}$ of 0.2 µM, followed by 2 ($IC_{50}$ about 9.9 µM). $IC_{50}$ values of compounds 3 and 4 were found to be 14-15 µM. In contrast, the protected analogs were much less active: <35% inhibition at 25 µM. This is consistent with the results above.

Figure 9A:
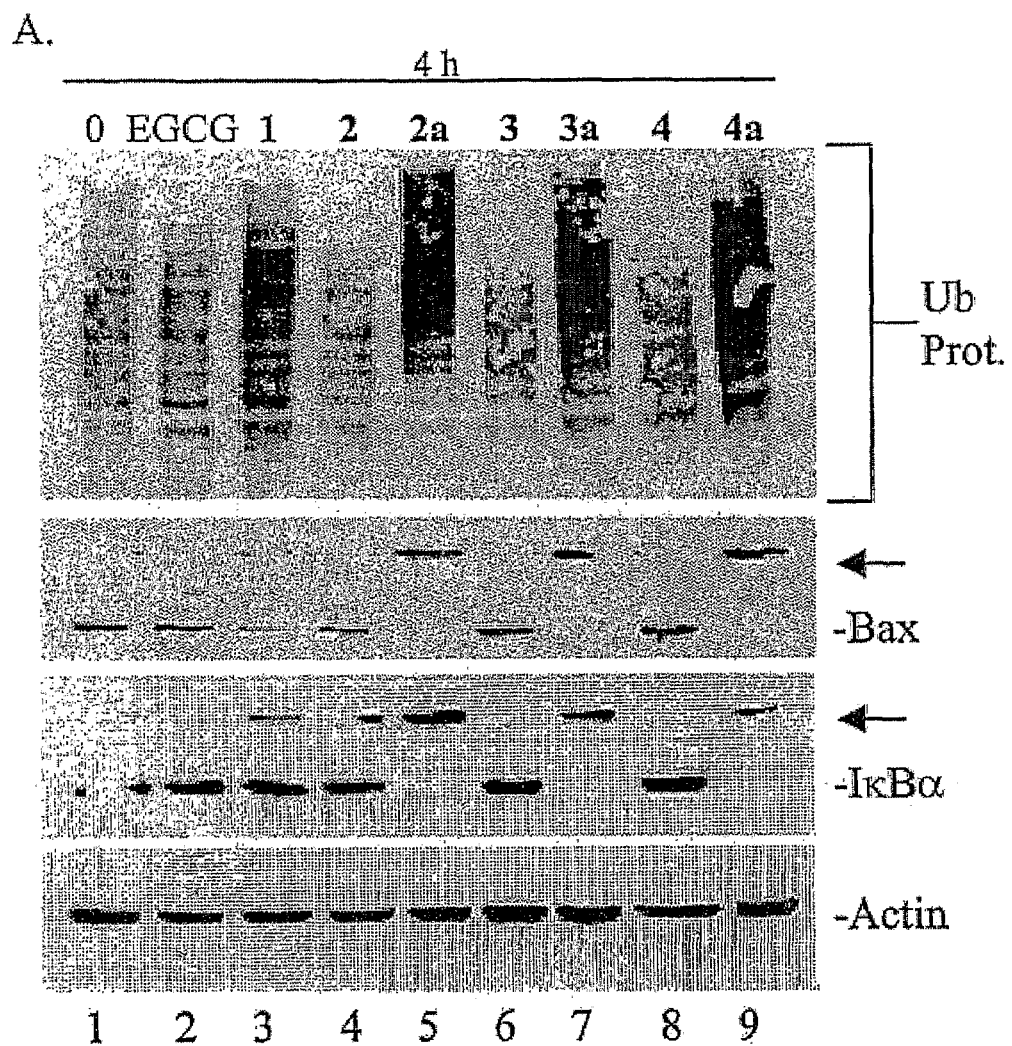
FIG. 9 shows the results of treating Jurkat cells with 25 µM of each indicated polyphenol for 4 h (A), up to 8 (C), or 24 h (B), or of LNCaP cells treated with 25 µM of indicated compound for 24 h (D), followed by Western blot analysis using specific antibodies to Ubiquitin, Bax, IκBα, p27 and Actin. The bands indicated by an arrow are possible ubiquitinated forms of Bax and IκBα. A, Lane 4, Ub-IκBα band may be result of spillage from Lane 5. Data shown are representative from three independent experiments.
Figure 9B:
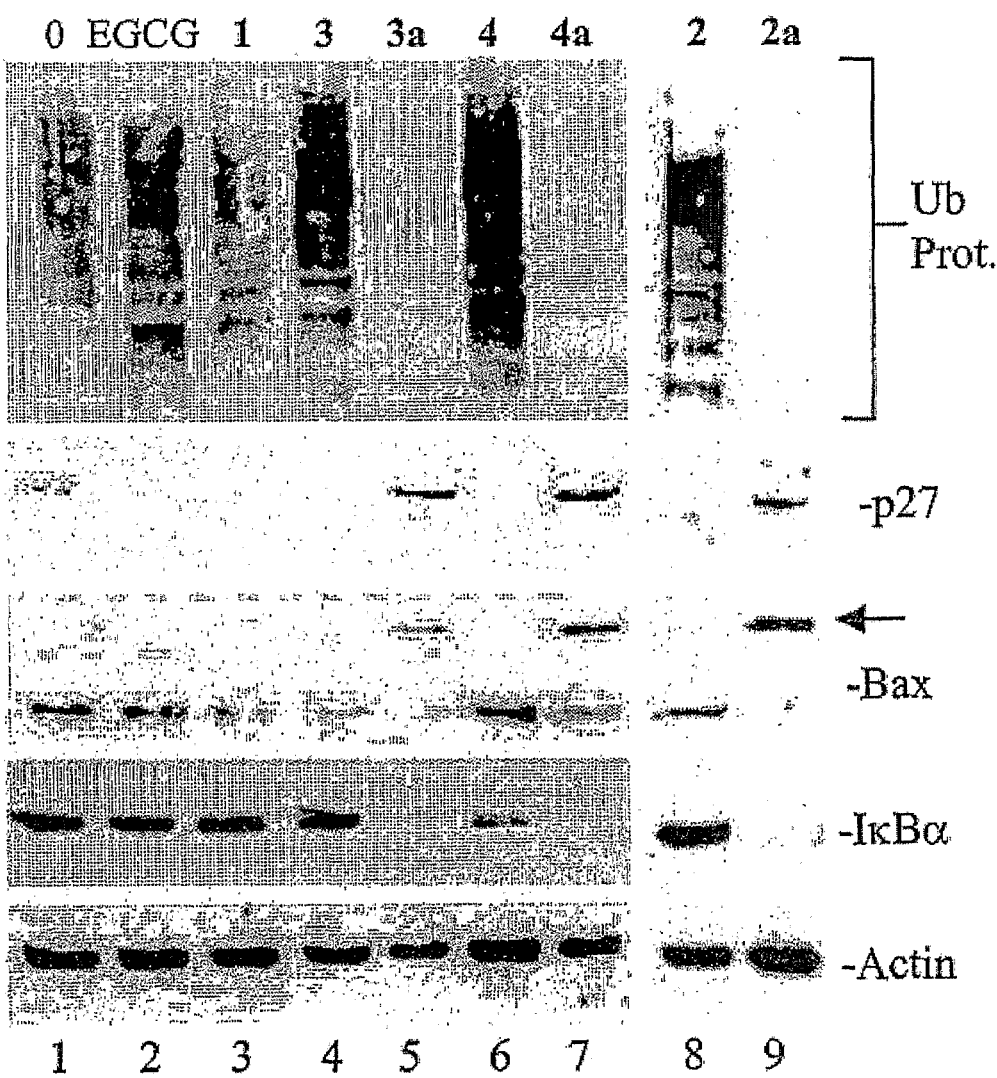

Protected Tea Analogs Exhibit Greater Proteasome-Inhibitory Potency in Intact Tumor Cells To determine what effects the synthetic tea analogs had on the proteasome in vivo, Jurkat cells were treated with 25 µM of each synthetic compound for either 4 or 24 h, with (−)-EGCG as a control (FIGS. 9A and 9B). After 4 h of treatment, Western blot analysis shows that the acetate-protected analogs induced a greater amount of ubiquitinated proteins (FIG. 9A, Lanes 5, 7, and 9), indicating that proteasome activity is abrogated. 1 was used as a control based on the above previous data showing that peracetate-protected (−)-EGCG is more potent than natural (−)-EGCG (FIG. 9A, Lanes 3 vs. 2). Additionally, Western blots for Bax and IκBα, known as two proteasome targets, revealed the disappearance of these proteins and the appearance of a higher molecular weight band, which is speculated to be multi-ubiquinated forms of the proteins (FIG. 9A, lanes 3, 5, 7, and 9). However, after 24 h treatment, (−)-EGCG and its unprotected analogs exhibited a greater amount of ubiquitinated proteins (FIG. 9B. Lanes 2, 4, 6, and 8). This is consistent with the idea that protected analogs are potent inhibitors of the proteasome at an earlier time point and that after 24 h of treatment the ubiquitinated proteins are being depleted by deubiquitinating enzymes. Accumulation of p27, another proteasome target, is also found in Jurkat cells treated with the protected analogs 2a, 3a and 4a (FIG. 9B, Lanes 9, 5, 7). The putative ubiquitinated IκBα band is still found in cells treated with 2a, 3a, and 4a (FIG. 9B, Lanes 9, 5, 7). The presumed ubiquinated IκBα band is now absent in the 24 h treatment, possibly due to deubiquitination (FIG. 9B). Actin was used as a loading control in this experiment.

Protected Analogs Induce Greater Cell Death in Leukemic Cells

Figure 9C:
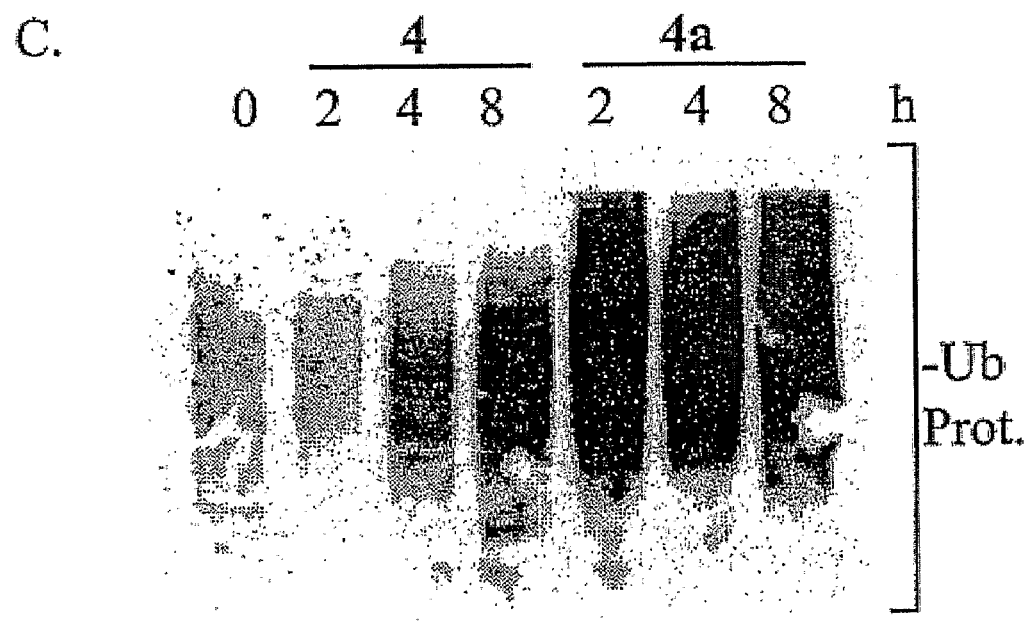
Figure 9D:
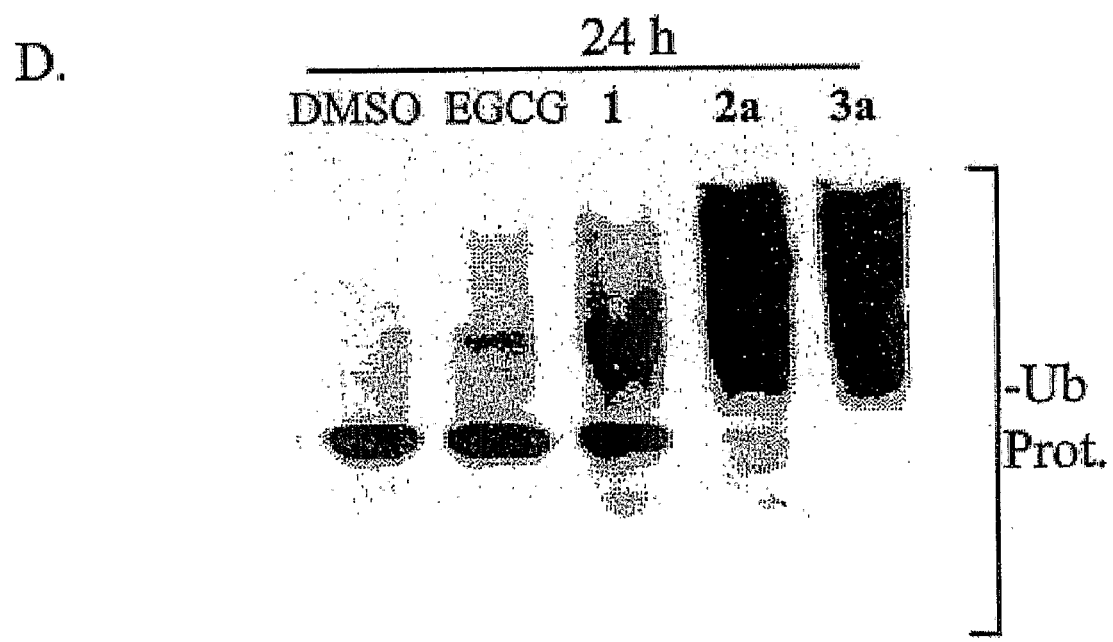

In a kinetics experiment using a pair of analogs, 4 and 4a, it was found that the unprotected analog 4 induced accumulation of ubiquitinated proteins with highest expression after 8 hours of polyphenol treatment (FIG. 9C). Conversely, the protected 4a showed increased ubiquitinated protein accumulation as early as 2 h and lasting up to 8 h (FIG. 9C). To determine if acetate-protected analogs are potent proteasome inhibitors in other cancer cell systems, prostate cancer LNCaP cells were treated for 24 h with 25 µM of (−)-EGCG, 1, 2a, or 3a, with DMSO as a control. Indeed, ubiquitin-conjugated proteins were observed, with the greatest increase found in cells treated with 2a and 3a (FIG. 9D).

Protected Analogs are More Potent Apoptosis Inducers

Figure 10A:
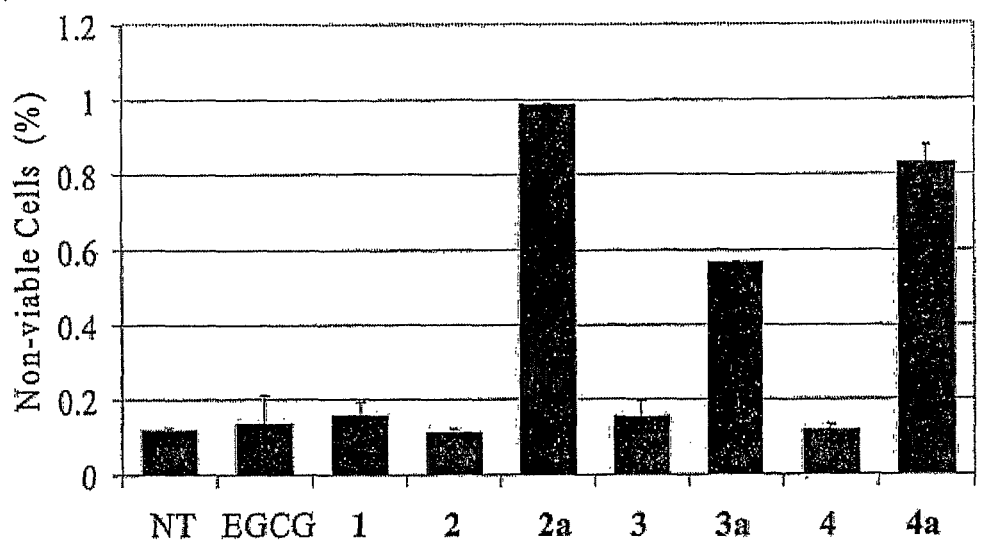
FIG. 10 shows the results of treating Jurkat T cells (A and B) or VA-13 (C and D) cells with 25 µM of indicated polyphenols for 24 h. A, Trypan blue incorporation assay. The data represented are as the mean number of dead cells over total cell population ±SD. B, Western blot for PARP cleavage. C, Fluorescent microscopy studies of late-stage apoptosis using a specific antibody to the p85 cleaved PARP fragment conjugated to FITC. Counterstaining with DAPI is used as a control for non-apoptotic cells. Images were obtained with AxioVision software utilizing an inverted fluorescent microscope (Zeiss, Germany). D, Quantification of apoptotic cells in C by counting the number of apoptotic cells over the total number of cells in the same field. Data are mean of duplicate experiments ±SD.
Figure 10B:
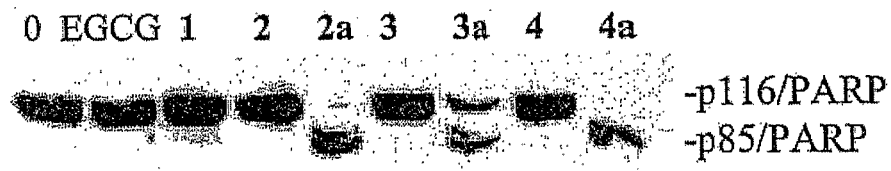
Figure 10C:
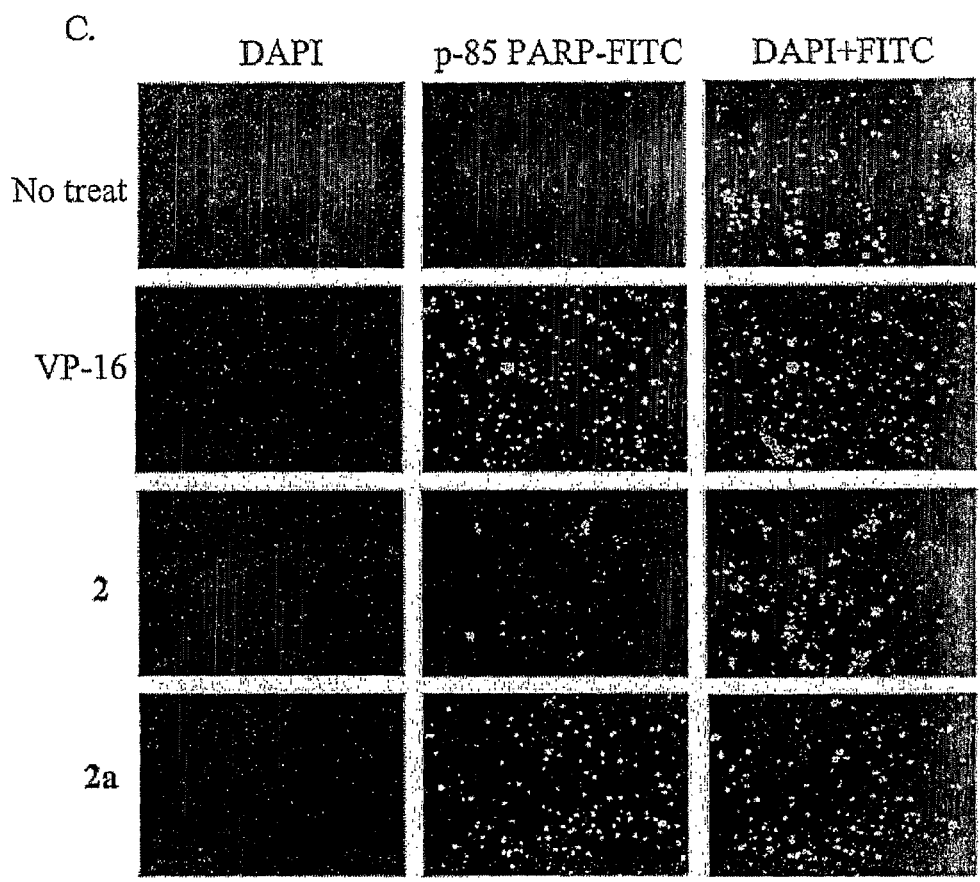
Figure 10D:
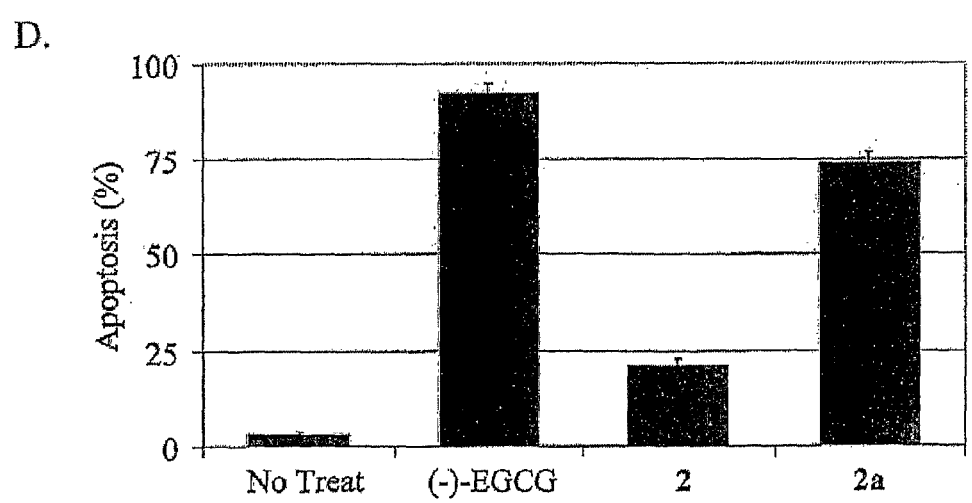

It has been shown that proteasome inhibition can induce apoptosis in a wide variety of cancer cells, but not in normal, non-transformed cells (An B et al). Jurkat T cells are treated with 25 µM of each of the selected polyphenols and their protected analogs for 24 h to investigate their abilities to induce apoptotic cell death. Trypan blue incorporation assay revealed that 2a, 3a and 4a, but not others, induced death in 99, 57, and 83% of Jurkat cells, respectively (FIG. 10A). Similarly, Western blot analysis showed that only 2a, 3a, and 4a induced apoptosis-specific PARP cleavage after 24 h (FIG. 10B). An immunofluorescent stain that detects only the cleavage PARP figment (p85; green) showed that SV40-transformed VA-13 cells are highly sensitive to apoptosis induced by 2a with 73% apoptotic cells after 24 h treatment (FIGS. 10C and 10D). The unprotected 2 induced much less apoptosis (21%), while 25 µM VP-16, used as a positive control, induced 92% apoptosis (FIGS. 10C and 10D). Counterstain with DAPI, which binds to the minor groove in A-T rich regions of DNA, was decreased drastically in apoptotic cells (FIG. 10C), consistent with DNA fragmentation in late stage apoptosis.

Inhibition of Tumor Cell Proliferation by Protected Polyphenols

Figure 11A:
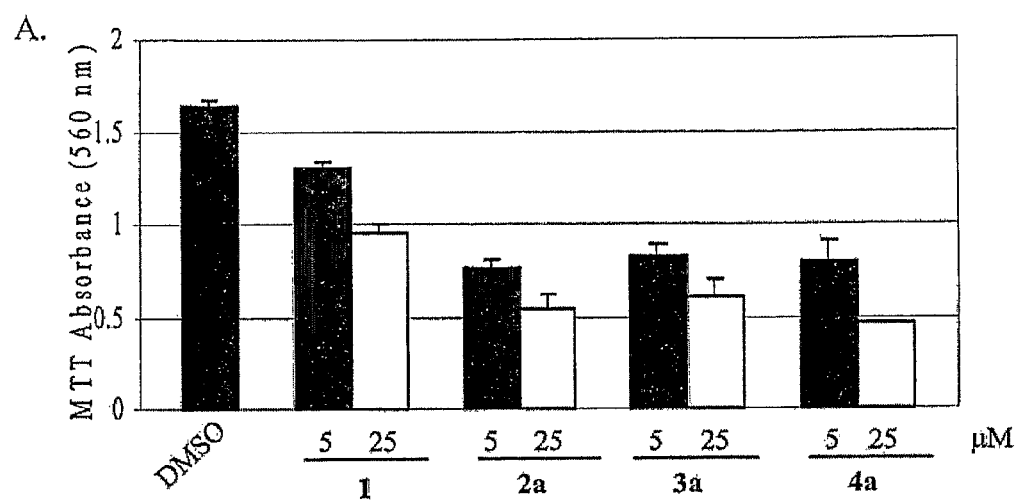
FIG. 11 shows the effects of synthetic acetylated polyphenols on breast and prostate cancer cells. A, MTT assay. Breast cancer MCF-7 cells were treated with each indicated compound at 5 or 25 µM for 24 h. B, Morphological changes. Prostate cancer LNCaP cells were treated with 25 µM of (−)-EGCG or a protected analog for 24 h, followed by morphological assessment. Images were obtained using a phase-contrast microscope at 40× magnification (Leica, Germany). C, Soft agar assay. LNCaP cells were plated in soft agar with the solvent DMSO or 25 pM of (−)-EGCG or protected analogs. Cells were cultured for 21 days without further addition of drug. Data shown are representative scanned wells from triplicate experiments. D, Colonies in C were quantified with an automated counter and presented as mean values ±SD.

Treated breast cancer (MCF-7) cells were then treated with 5 or 25 µM of peracetate-protected analogs for 24 h, followed by MTT analysis to determine their effects on cell proliferation. Compound 1 at 25 µM inhibited cellular proliferation by 40% (FIG. 11A). The protected compounds 2a, 3a, and 4a caused 50% inhibition at 5 µM and 70% at 25 µM, respectively (FIG. 11A).

Figure 11B:
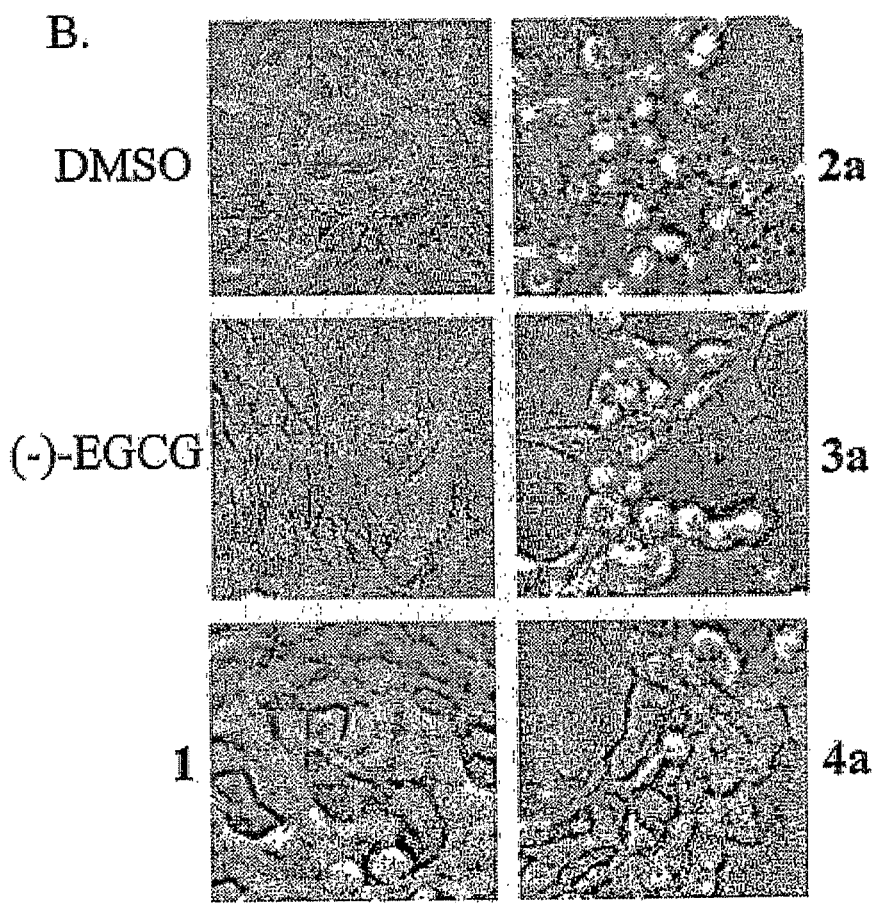

Human prostate cancer LNCaP cells were then treated for 24 h with each selected tea polyphenol protected analogs 1, 2a, 3a, 4a at 25 µM, followed by determining the apoptotic morphological changes. Again, the protected analogs 2a, 3a, and 4a caused dramatic round-up, detachment, and cellular fragmentation (FIG. 11B). 1 induced mild morphological changes, while (−)-EGCG treatment led to enlarged, flattened cells, indicating growth arrest.

Figure 11C:
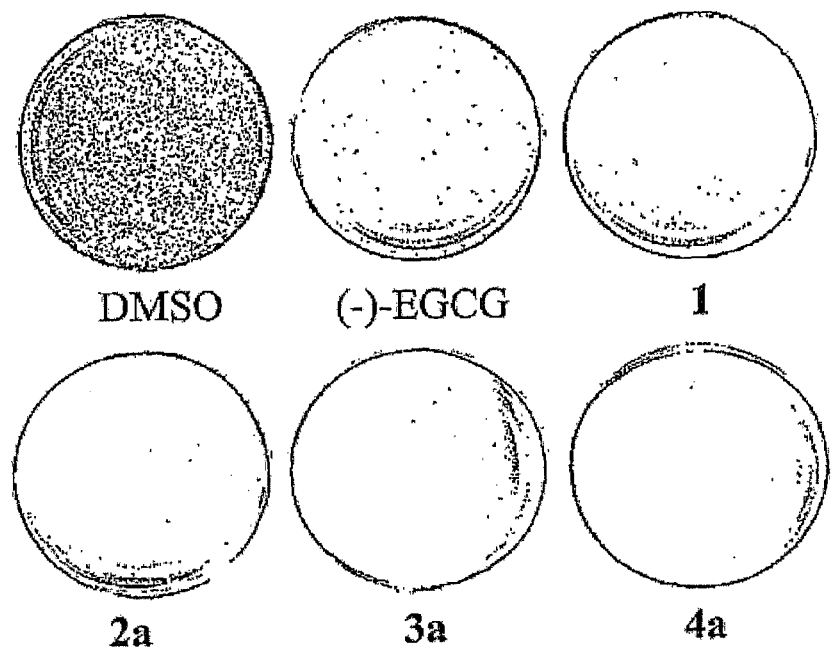
Figure 11D:
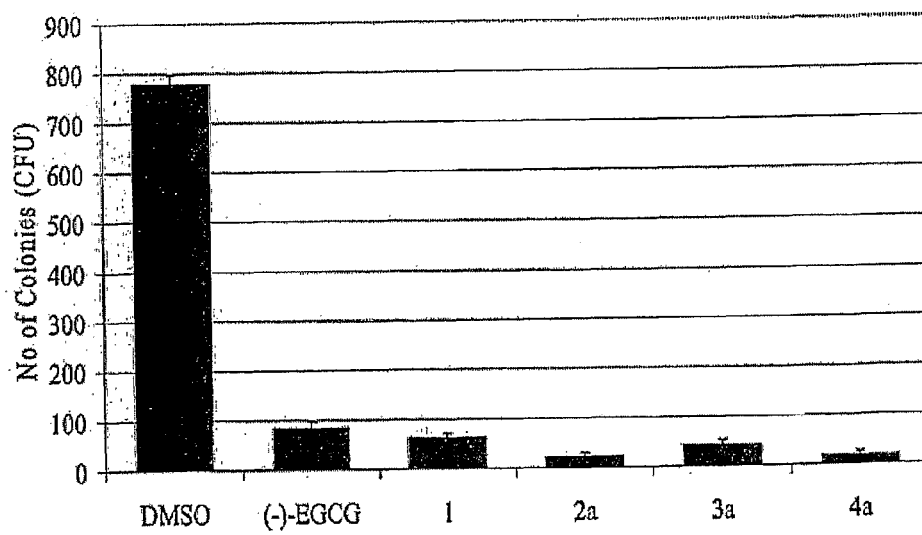

Soft agar assay is used to determine the transforming activity of tumor cells. Abrogation of colony formation is linked to GI arrest and/or apoptosis. LNCaP cells were added to soft agar in 6-well plates, and were then treated one time at initial plating with 25 µM of (−)EGCG or a protected analog (FIG. 11C). After 21 days, colony formation was evaluated. Cells treated with (−)-EGCG showed a significant decrease in colony formation compared to the control cells treated with DMSO (FIGS. 11C and 11D). Protected polyphenols also inhibited tumor cell transforming activity, with 2a and 4a being the most potent inhibitors of colony formation (FIG. 11D).

Preferential Induction of Apoptosis in Tumor Cells by Protected Analogs

Figure 12A:
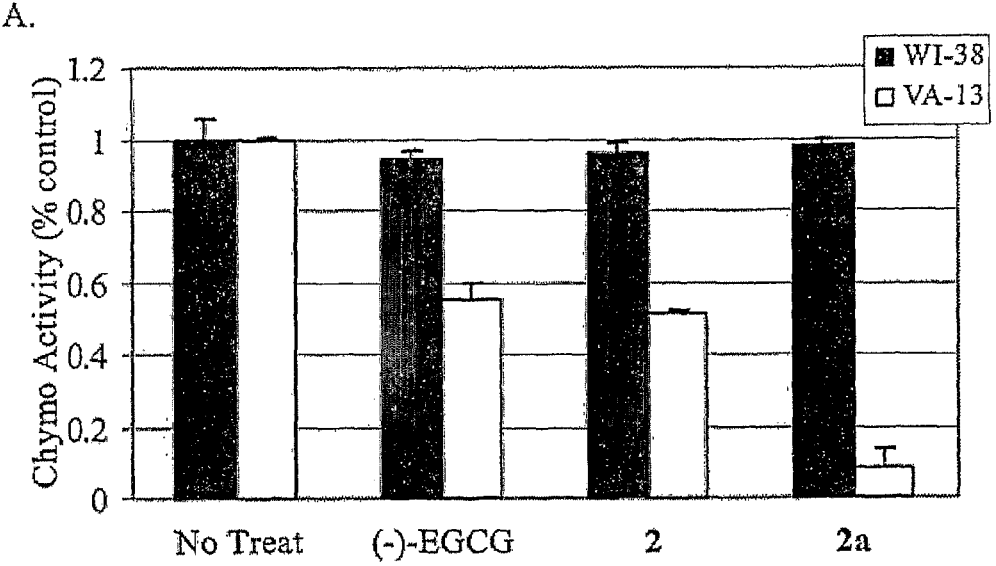
FIG. 12 shows the results of treating normal WI-38 and SV-40-transformed VA-13 cells with 25 µM of indicated compounds for 24 h (A and B) or 36 h (C), or leukemic Jurkat T and non-transformed YT cells were treated with each compound at 25 µM for 24 h (D). A, Chymotrypsin-like activity of the proteasome in intact cells. B and C, Nuclear staining for apoptotic morphology of both detached and attached cells at 10× (B) or 40× (C) magnification. Missing panels indicate that no detachment of cells occurred. D, Western blot analysis using specific antibody to PARP.

The ability to induce apoptosis in tumor cells, but not normal cells is an important measure for novel anti-cancer drugs. To determine whether the protected compounds also affect normal cells, both VA-13 and WI-38 cells were treated with 25 µM of (−)-EGCG, 2, or 2a for 24 h and examined proteasome activity, nuclear morphological changes, and detachment. A differential decrease was found in the chymotrypsin-like activity of the proteasome in VA-13 cells over normal WI-38 cells (FIG. 12A). A 42-48% decrease in proteasome activity was observed in VA-13 cells treated with (−)-EGCG and 2, while 2a inhibited 92% of the proteasomal activity. Conversely, the proteasome activity in WI-38 cells was decreased by only −5% with all three polyphenol treatments.

Figure 12B:
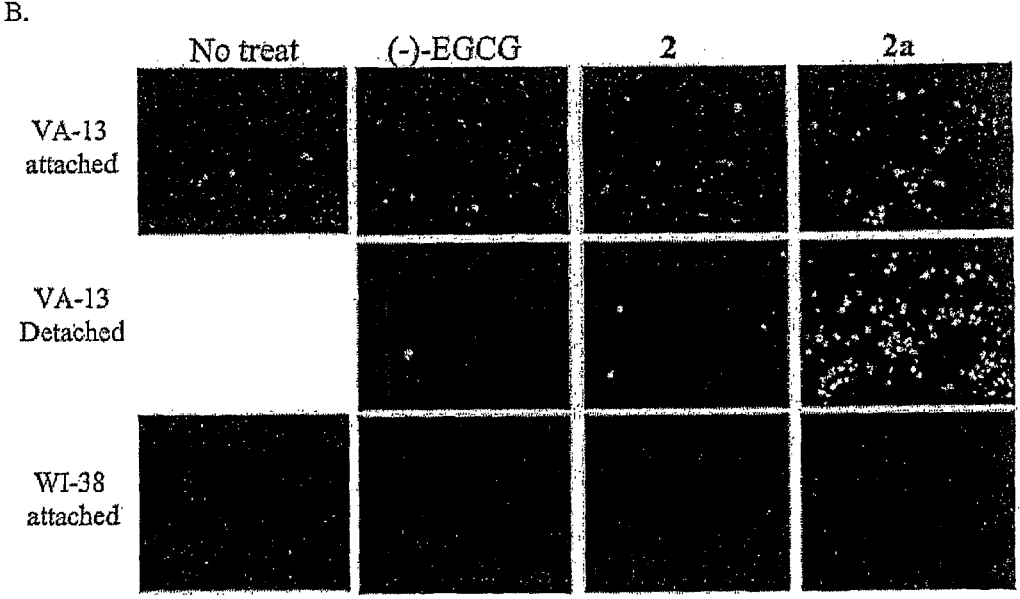
Figure 12C:
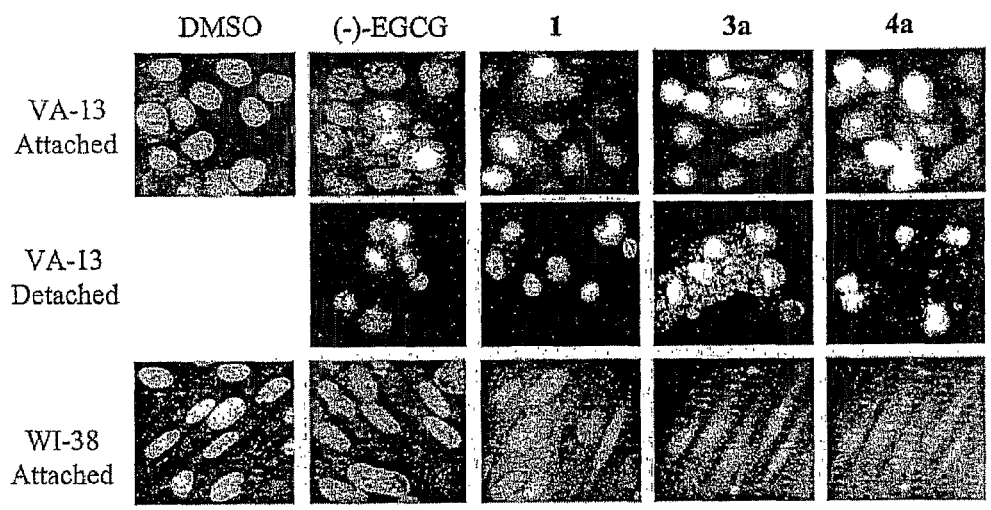
Figure 12D:
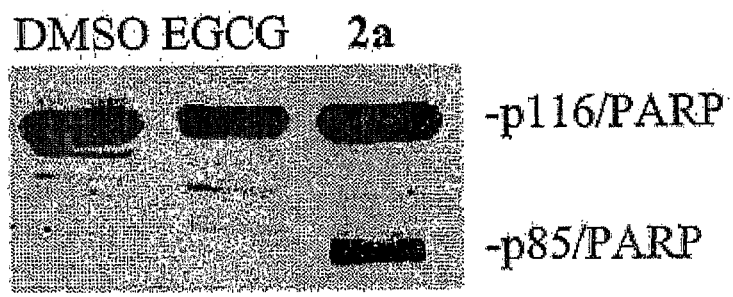
Figure 12D:
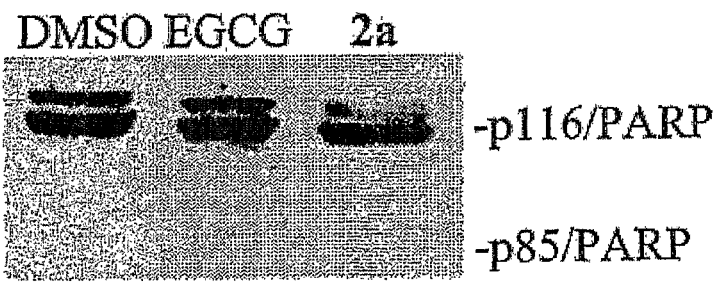

Next, apoptotic nuclear morphology is examined after treatment with natural (−)-EGCG, 2, and 2a (FIG. 12B). While (−)-EGCG and 2 exhibited little or no apoptosis, 2a markedly induced apoptosis in SV-40-transformed VA-13 cells. In contrast, normal WI-38 fibroblasts treated with all the compounds did not undergo apoptosis and very little detachment was visible. A comparison among all the protected analogs was then performed using 25 µM for 24 h. After 36 h, (−)-EGCG did initiate apoptosis in VA-13 cells (FIG. 12C). All of the protected analogs induced apoptosis in transformed (VA-13), but not normal (WI-38) cells (FIGS. 12B and 12C). Similarly, when leukemic (Jurkat T) and normal, non-transformed natural killer (YT) cells were treated with (−)-EGCG and 2a for 24 h, only Jurkat cells underwent apoptosis as evidenced by PAW cleavage (FIG. 12D).

Inhibition of Purified 20S Proteasome Activity by New Synthetic Tea Polyphenol Analogs.

The green tea polyphenol (−)-EGCG contains a B-ring with three —OH groups (FIG. 1) and has an $IC_{50}$ value of 0.3 µM to a purified 20S proteasome (Table 1).

TABLE 1

Inhibition of proteasome activity to synthetic tea polyphenols[1,2]

| Unprotected | $IC_{50}$ (µM) | Protected | $IC_{50}$ (µM) |
|---|---|---|---|
| (−)-EGCG | 0.30 ? 0.02 | | |
| No 16 | 0.59 ? 0.17 | No 24* | n.a.[3] |
| No 6 | 2.69 ? 1.07 | No 19* | n.a.[3] |
| No 15 | 4.56 ? 1.20 | | |
| No 12 | 5.99 ? 0.13 | No 23* | n.a.[3] |
| No 11 | 7.70 ? 0.14 | No 22* | n.a.[3] |
| No 10 | 8.51 ? 0.47 | No 21* | n.a.[3] |

[1]Inhibition of purified 20S proteasome was assessed using a chymotrypsin-like specific fluorogenic substrate (Suc-Leu-Leu-Val-Tyr-AMC). 20S proteasomes were incubated with polyphenols for 2 h.
[2]Results obtained from 3 independent experiments performed in triplicate.
[3]n.a. indicates that the inhibitory activity of the purified 20S proteasome at 25 µM was <20%.

Removal of an —OH from B-ring of (−)-EGCG generates (−)-ECG that has decreased proteasome-inhibitory potency in vitro (0.58 µM). To further examine the effects of B-ring —OH group deletion on proteasome-inhibitory and cell death-inducing abilities, we synthesized several novel EGCG analogs with eliminated —OH groups on the B-ring as well as their putative prodrugs, the peracetate-protected counterparts. By using a purified 20S proteasome and a chymotrypsin-like fluorogenic substrate, the proteasome-inhibitory effects of the following unprotected polyphenol analogs are determined:

TABLE 2

Effects of natural and synthetic tea polyphenols on 20S prokaryotic proteasome activities. Reference a is Smith, D. M.; Daniel, K. G.; Wang, Z.; Guida, W. C.; Chan, T. H.; Dou, Q. P. Proteins: Structure, Function, and Bioinformatics, 2004, 54, 58

| Compound | $IC_{50}$ (µM) | Reference |
|---|---|---|
| (−)-EGCG | 0.30 | This work |
| (−)-ECG, 8 | 0.58 | Reference a |
| (+)-CG, 7 | 0.73 | Reference a |
| (−)-EZG, 6 | 2.69 | This work |
| (+)-ZG, #m | 4.56 | This work |
| #n | 0.84 | This work |
| #o | 1.22 | This work |
| 15 | 4.56 | This work |
| (+)-ECG | 0.73 | Reference a |
| #1 | 0.39 | This work |
| (−)-CG | 0.75 | Reference a |
| 16 | 0.59 | This work |

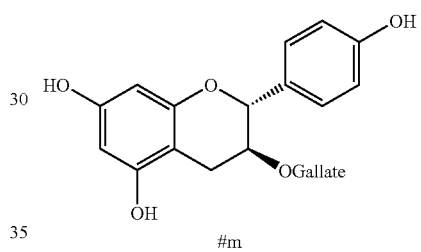

m

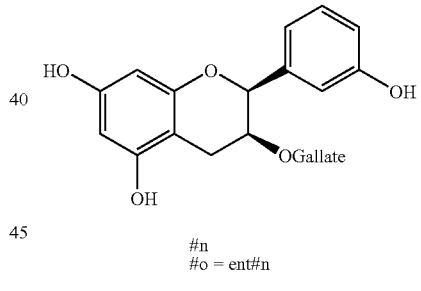

n
o = ent#n

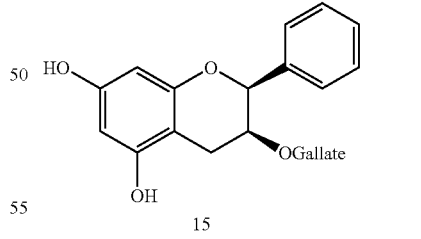

15

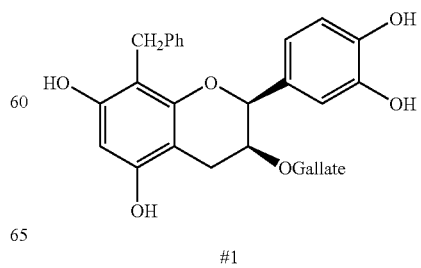

1

TABLE 2-continued

Effects of natural and synthetic tea polyphenols on 20S prokaryotic proteasome activities. Reference a is Smith, D. M.; Daniel, K. G.; Wang, Z.; Guida, W. C.; Chan, T. H.; Dou, Q. P. Proteins: Structure, Function, and Bioinformatics, 2004, 54, 58

| Compound | IC50 (µM) | Reference |
| --- | --- | --- |

16

Figure 13:
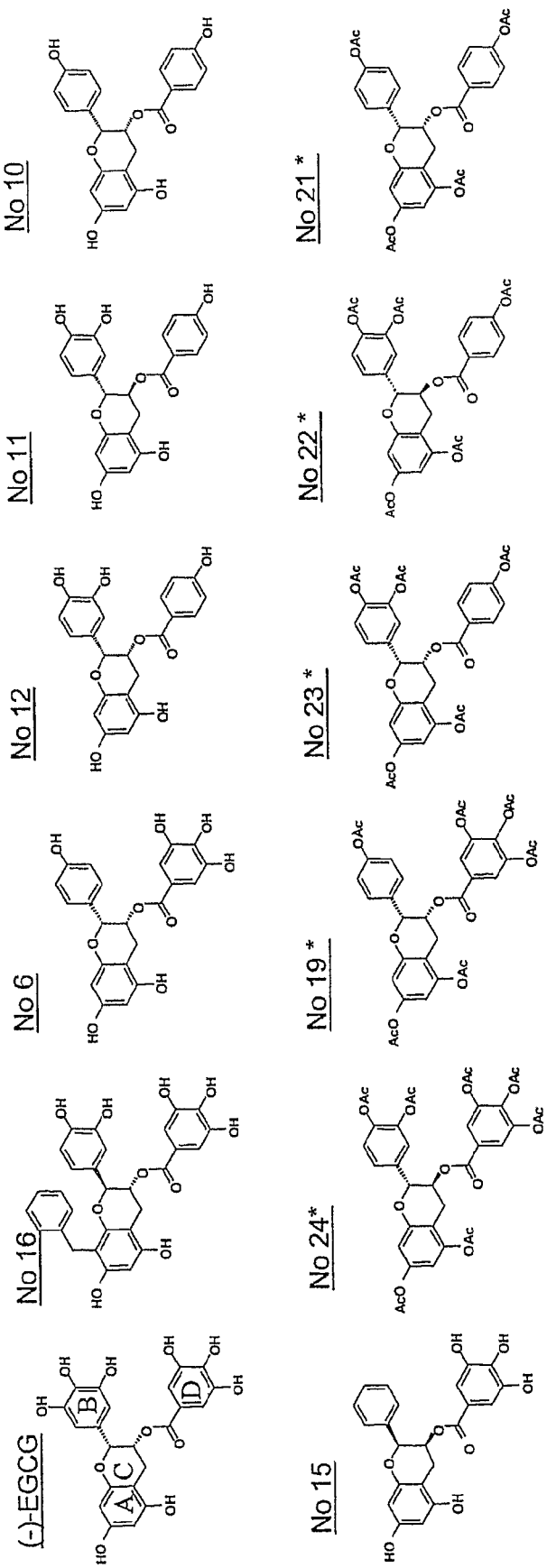
FIG. 13 shows the structures of the (−)-EGCG, and examples of the (−)-EGCG peracyloxyl derivatives of this invention.
Figure 13A:
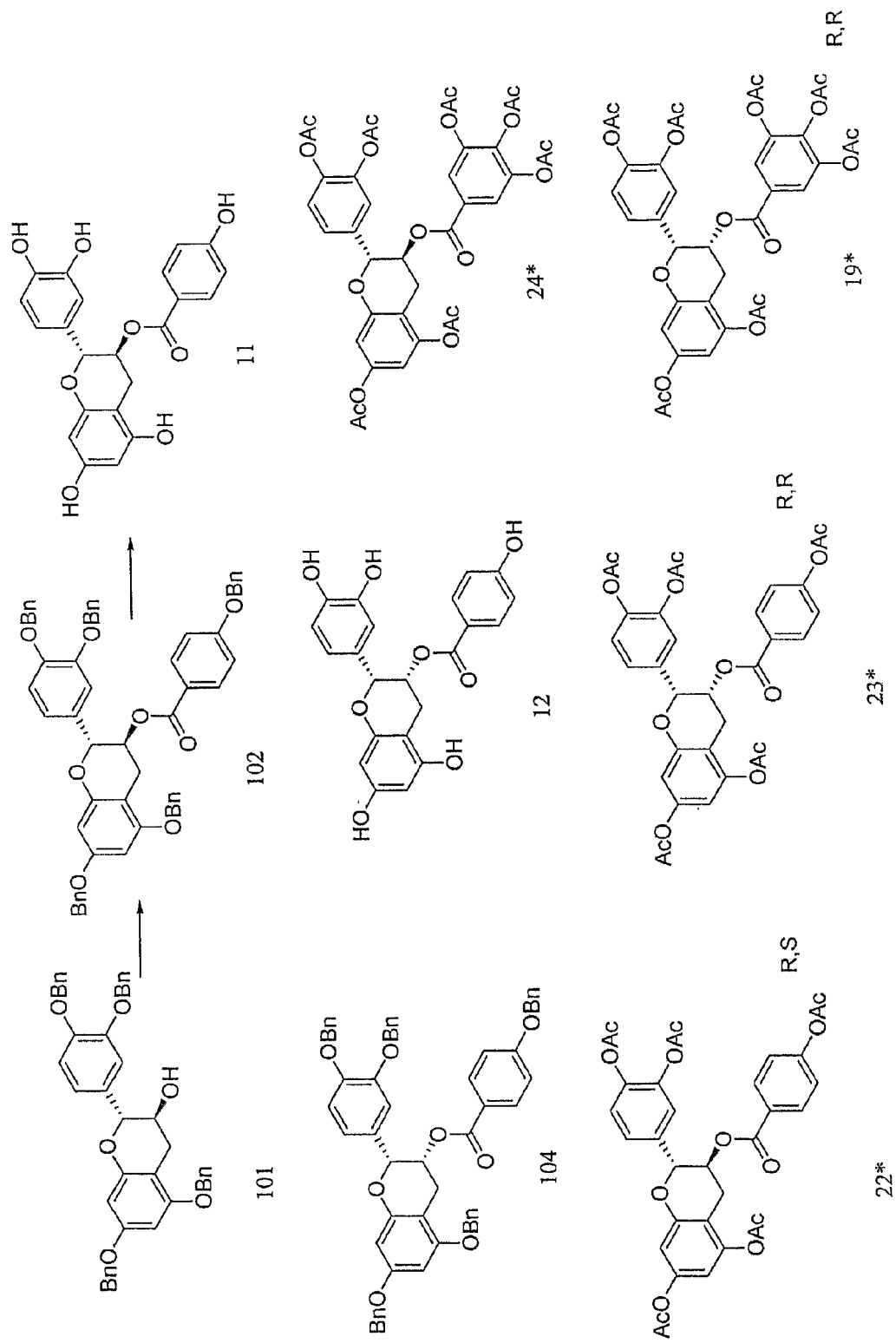
FIGS. 13a and 13b show the intermediates when synthesizing the (−)-EGCG peracyloxyl derivatives of this invention.
Figure 13B:
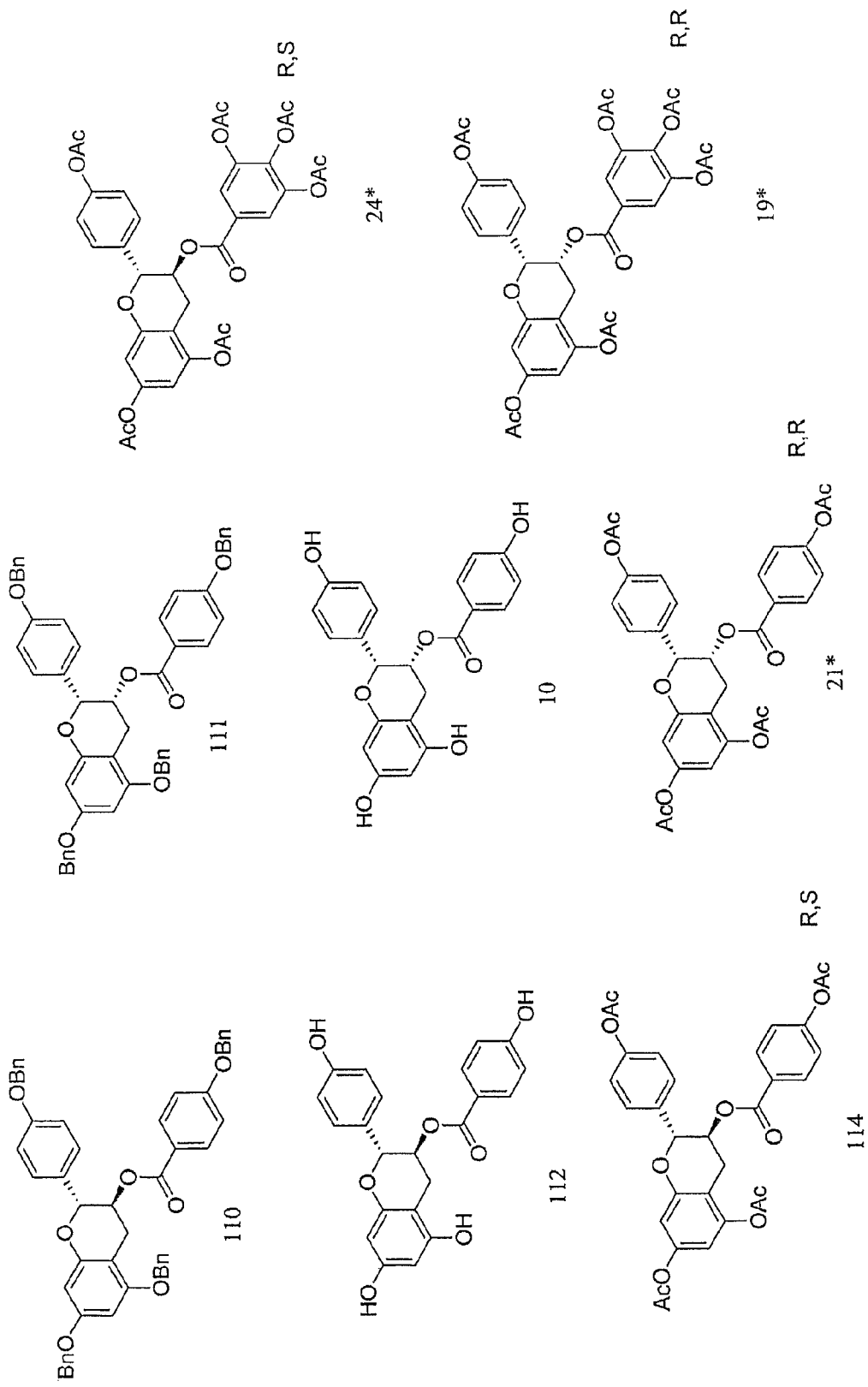

A good correlation between proteasome-inhibitory activity and the number of —OH groups on the B-ring and on the D-ring is observed. As individual —OH groups were eliminated from the B-ring, the $IC_{50}$ values increased stepwise and the order of potency observed was: (−)-EGCG ($IC_{50}$ 0.30 µM)>(−)-ECG (0.58 µM)>6 (2.69 µM)>#m (4.56 µM) (FIG. 13 and Table 1). Consistently, in the series of compounds 12, 11 (an epimer of 12) and 10 which contain one —OH on the D-ring (FIG. 13), 12 and 11 with two B-ring —OH groups are more potent than 10 with only one B-ring —OH group (5.99, 7.70, and 8.51 µM, respectively; Table 1).

Additional SAR analysis also revealed that when more —OH groups were removed from the D-ring, the inhibitory potency was further decreased as compared to B-ring —OH eliminations alone. For example, 6 is more potent than 10 (2.69 vs. 8.51 µM), and (−)-ECG as well as (−)-CG are more potent than No 12 [0.58 and 0.75 vs. 5.99 µM;]. Finally, we have included compound 16 to probe the hydrophobic effect around the A ring. Indeed, compound 16 was found to be more active than the counterpart (−)-CG [0.59 vs. 0.75 µM; FIG. 13; Table 1 and 2].

As a comparison, the inhibitory activities of the protected polyphenol analogs to purified proteasome are also determined. As expected, the peracetate-protected analogs (indicated by *) were not potent inhibitors of the chymotrypsin-like activity of the purified 20S proteasome, compared to their unprotected analogs, perhaps due to the lack of cellular esterases required for conversion. All the protected analogs at 25 µM inhibited <20% of the purified 20S proteasome activity (Table 1).

Inhibition of Cellular Proteasome Activity by Synthetic Tea Polyphenols

Figure 14:
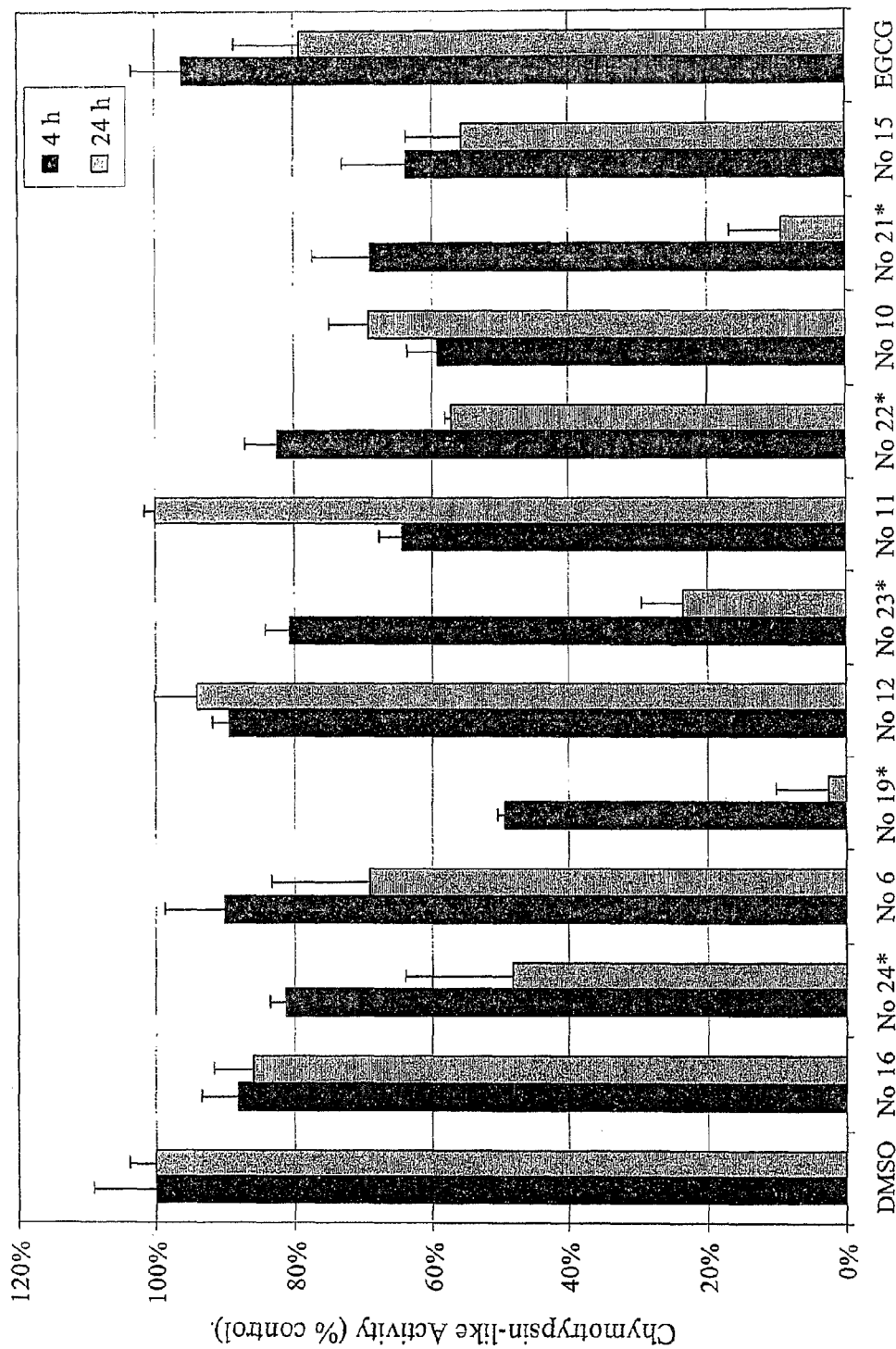
FIG. 14 shows the chymotrypsin-like activity when Jurkat T cells were preincubated with the solvent (DMSO), 25 µM of the compounds in FIG. 13.

To determine whether the unprotected and protected polyphenol analogs could inhibit the proteasomal activity in intact cells, leukemia Jurkat T cells were treated with each compound at 25 µM for 4 and 24 h, followed by collection of cell pellets and measurement of the proteasomal chymotrypsin-like activity in the prepared lysates. The unprotected compounds show limited proteasome inhibition in intact Jurkat T cells although 10 and 15 showed moderate potency (FIG. 14). These data suggest that most, if not all, of the unprotected compounds are only moderately active in the cellular environment, similar to (−)-EGCG, presumably because of their cellular instability.

Importantly, all of the peracyloxyl-protected, particularly, peracetate-protected polyphenols tested were much more potent inhibitors of the proteasomal chymotrypsin-like activity than their unprotected counterparts after 24 h treatment (FIG. 14). Especially, 19* inhibited 97% of the chymotrypsin-like activity while its unprotected polyphenol counterpart, 6, inhibited only 30% of the chymotrypsin-like activity after a 24 h treatment.

Figure 15:
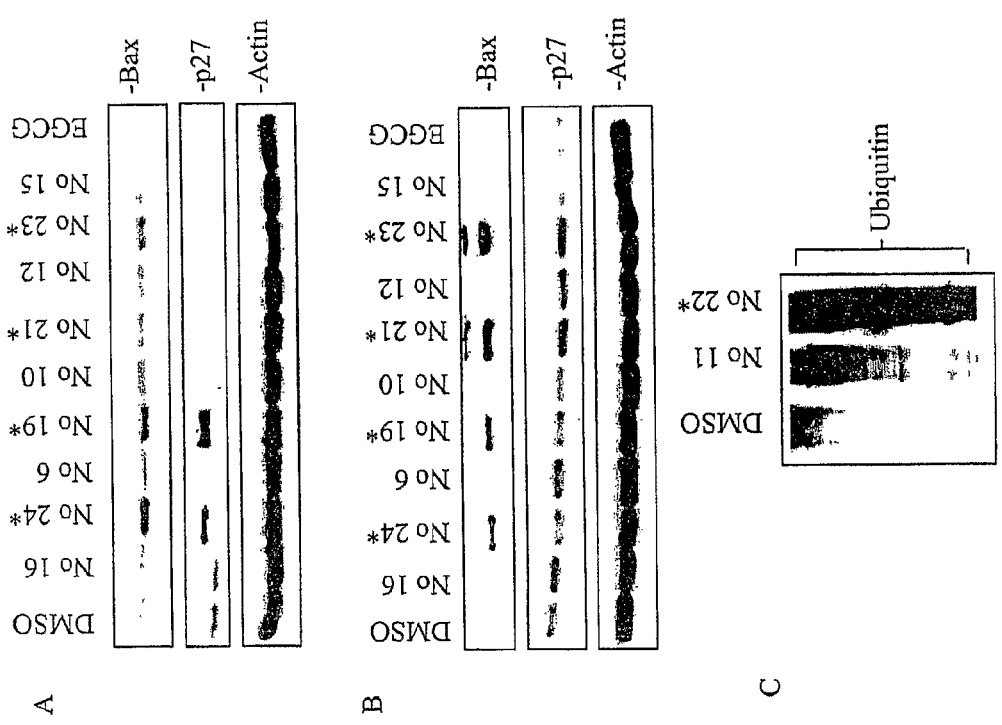
FIG. 15 shows the accumulation of proteasome target and ubiquitinated proteins when Jurkat T cells were treated with the solvent (DMSO), and 25 µM of the compounds in FIG. 13.

The pro-apoptotic protein Bax and the cyclin-dependent kinase inhibitor p27 are natural proteasome targets. If the peracetate-protected polyphenols inhibit the intact proteasome activity, we would expect accumulation of Bax and p27 in these cells. To test this idea, Jurkat T cells were treated with both protected and unprotected compounds and lysates were analyzed by Western blot using specific antibodies to Bax and p27 (FIG. 15). After 4 h of treatment, the peracetate-protected analogs 24* and 19*, but not their unprotected analogs, were able to increase accumulation of both Bax (by 3- and 2.5-fold, respectively) and p27 (6- and 11-fold, respectively) (FIG. 15A). After 24 h treatment, Bax levels were increased in cells treated with all of the peracetate-protected compounds (13-, 12-, 40- and 36-fold, respectively, by 24*, 19*, 21* and 23*). However, p27 increase was observed with treatment of mainly 21* (2-fold) and 23* (2-fold) after 24 h (FIG. 15B). In addition, levels of ubiquitinated proteins, an indicator of proteasome inhibition, were significantly increased by the protected 22*, but not its corresponding, unprotected 11, after 4 h treatment (FIG. 15C). These data are consistent with the profile of the proteasome-inhibitory activities of these compounds (FIG. 14). It is suggested the protected analogs can be converted into active proteasome inhibitors in cultured tumor cells.

Induction of Apoptotic Cell Death by Synthetic Tea Polyphenol Analogs.

Figure 16:
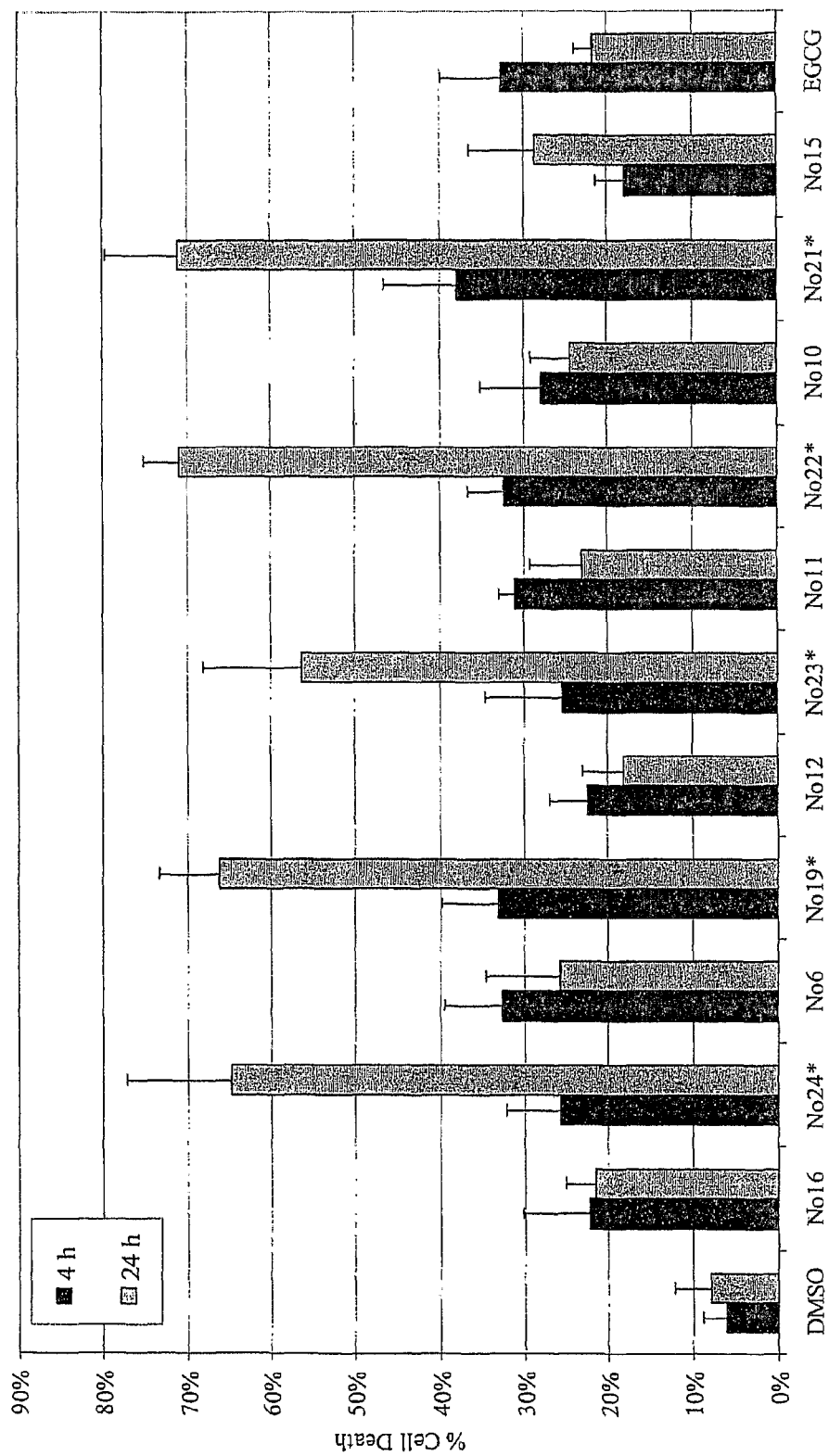
FIG. 16 shows the percentage cell death when Jurkat T cells were treated with the solvent (DMSO), and 25 µM of the compounds in FIG. 13.

It has previously been shown that proteasome inhibition is associated with apoptosis induction. To determine if the B-ring/D-ring protected analogs were capable of inducing cell death, Jurkat T cells were first treated with all the protected and unprotected analogs at 25 µM for 24 h, followed by trypan blue exclusion assay (FIG. 16). Changes in cell morphology (shrunken cells and characteristic apoptotic blebbing) were observed after 4 h treatment with both protected and unprotected analogs and these changes were greatly increased after 24 h treatment with protected analogs (data not shown). Furthermore, the peracetate-protected analogs induced a 5- to 10-fold increase in cell death after 4 h incubation and up to 20-fold increase at 24 h (FIG. 16). In contrast, the unprotected polyphenols caused much less cell death, only 3- to 5-fold increase after even 24 h treatment (FIG. 16).

To determine if the cell death observed (FIG. 16) was due to the induction of apoptosis, a similar experiment was performed in Jurkat T cells, followed by measurement of caspase-3 activation and PARP cleavage. The peracetate-protected polyphenols induced the highest levels of caspase-3 activity (FIG. 17A): 24* treatment for 4 h resulted in an 16-fold increase while the unprotected 16 resulted in only a 4-fold increase. Furthermore, the protected 19* treatment increased the caspase-3 activity by 16-fold, while the unprotected counterpart, 6, had much less effect (4-fold). Consistently, PARP cleavage was detected in cells treated with 24* and 19*, but not with the unprotected counterparts 16 and 6 (FIG. 17B). Furthermore, the protected compound 22*, but not its unprotected counterpart 11, was able to induce PARP cleavage in cells after 4 h treatment (FIG. 17C).

Preferential Induction of Apoptosis in Tumor Cells by Peracetate-Protected (−)-EGCG Analogs.

Figure 18:
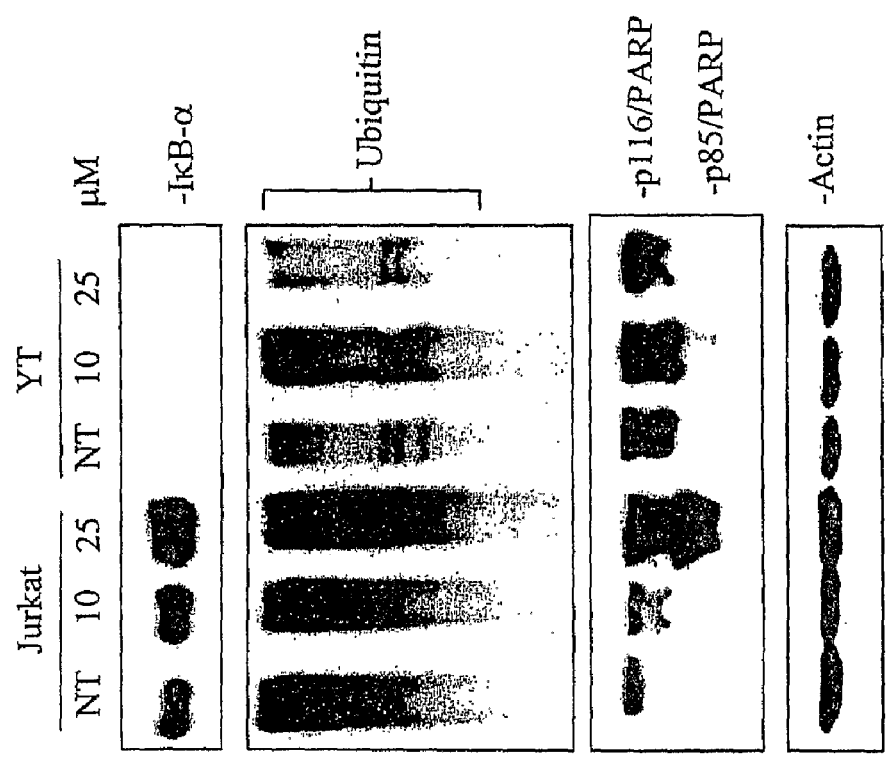
FIG. 18 shows the induction of apoptosis in tumor cells when Jurkat T cells and non-transformed human natural killer (YT) cells were treated for 4 h with 10 and 25 µM of the 19*, followed by Western blot analysis using specific antibodies to IκB-α, PARP and Actin.

Apoptosis induction in tumor cells but not in normal cells is an important aspect of anti-cancer drugs. To determine whether the peracetate-protected analogs affect normal cells, we treated both leukemic Jurkat T cells and non-transformed immortalized natural killer (YT) cells with the seemingly most potent peracetate-protected analog, 19*. Again, levels of proteasome target proteins Bax, p27 (data not shown), and IκBα (FIG. 18) were increased in leukemia Jurkat T cells. However, levels of these proteins were not increased in the non-transformed immortalized YT cells. In addition, levels of ubiquitinated proteins were accumulated in a dose-dependent manner in Jurkat T cells. In contrast, only a slight, transient increase in levels of ubiqitinated proteins was detected in the YT cells. Consistent with the selective inhibition of the proteasome activity, the apoptosis-specific PARP cleavage was found only in the Jurkat T, but not YT cells. Thus, potent peracetate-protected polyphenols apparently do not induce proteasome inhibition and subsequent apoptosis in non-transformed YT cells.

Discussion

Natural (−)-EGCG from green tea has been converted to its peracetate compound 1. In addition, several synthetic analogs to (−)-EGCG that possess deletions of the hydroxyl groups on the gallate ring are synthesized. Additionally, the hydroxyl groups were converted to acetate groups to create a prodrug, which could be cleaved via esterases inside the cell and converted to the parent drug. Surprisingly, the protected analogs were much more potent proteasome inhibitors in intact tumor cells than their unprotected counterparts. Consistently, the protected analogs were also more potent apoptosis inducers than unprotected partners, when tested in leukemic (Jurkat), solid tumor and transformed cell lines. SAR analysis of the protected analogs revealed that the order of their potency is as follows: 2a=4a>3a>1>(−)-EGCG.

Protected analogs of (−)-EGCG were designed and synthesized. Unexpectedly, these compounds appear to have proteasome inhibitory activity in vivo.

The peracyloxyl, particularly peracetate-protected analogs are also found to be more potent proteasome inhibitors than their unprotected, hydroxylated counterparts. It was suggested that the N-terminal Thr of the chymotrypsin-like subunit (β5) of the proteasome executes a nucleophilic attack on the ester-bonded carbon of (−)-EGCG, which initiates irreversible acylation to the β5-subunit and inhibits its protease activity (Nam S, Smith D M and Dou Q P: *J Biol Chem* 276: 13322-13330, 2001.). However, addition of the peracetate moieties reduces the electrophilic character of the ester-bond carbon, leading to much reduced inhibition to the purified 20S proteasome. Unsurprisingly, the protected polyphenols examined here also exhibited limited inhibition to the chymotrypsin-like activity of purified 20S proteasome (Table 1).

A correlation is shown between the activity of proteasome inhibition and the number of —OH groups on the B-ring (Table 2). The $IC_{50}$ values of unprotected analogs increased stepwise as individual —OH groups were eliminated (Table 1). Although, 16 contains an additional benzene ring off the $C_8$ carbon on the A ring of (−)-CG, it has slightly increased proteasome-inhibitory potency to (−)-CG (0.59 vs. 0.75 μM).

Another important SAR found is that further elimination of —OH groups from the D-ring leads to further decreased proteasome-inhibitory potency in vitro (Table 1).

As shown in FIG. 14, the peracetate-protected polyphenols were much more potent inhibitors of the proteasomal chymotrypsin-like activity than the unprotected polyphenols. Peracetate-protected analogs appear to be stable for extended time points evidenced by the decrease in cellular proteasomal chymotrypsin-like activity at 24 h. In contrast, the unprotected analogs appear to lose stability after 24 h treatment. Cellular proteasomal chymotrypsin-like activity was inhibited 97% by analog 19* after 24 h while its unprotected counterpart, 6, inhibited only 30% of the activity. Compared to other pairs of protected vs. unprotected compounds, 22* displayed relatively small increase in chymotrypsin-inhibitory potency from its counterpart 11, indicating possible conversion of 22* to the parent drug in cells. Although the mechanism is not fully understood, other peracetate-protected green tea analogs seem to be converted to distinct potent compounds in a cellular environment.

Several proteasome target proteins were also evaluated after proteasome inhibition with synthetic tea polyphenols (FIG. 15). The data provided another piece of evidence that peracetate-protected analogs require the milieu of the cell and/or cell extract to be converted into effective proteasome inhibitors, represented by the accumulation of Bax, p27, and ubiquitinatied proteins. The protected analogs were able to accumulate target proteins with greater efficacy than their unprotected counterparts in a cellular model compared to the in vitro model. In contrast, the unprotected analogs did not appear to accumulate target proteins to the extent of the protected analogs, which may be a result of proton donation from the —OH groups and subsequent degradation. The data further indicates that the peracetate-protected analogs undergo conversion to a new compound and act as prodrugs in vivo.

Figure 17:
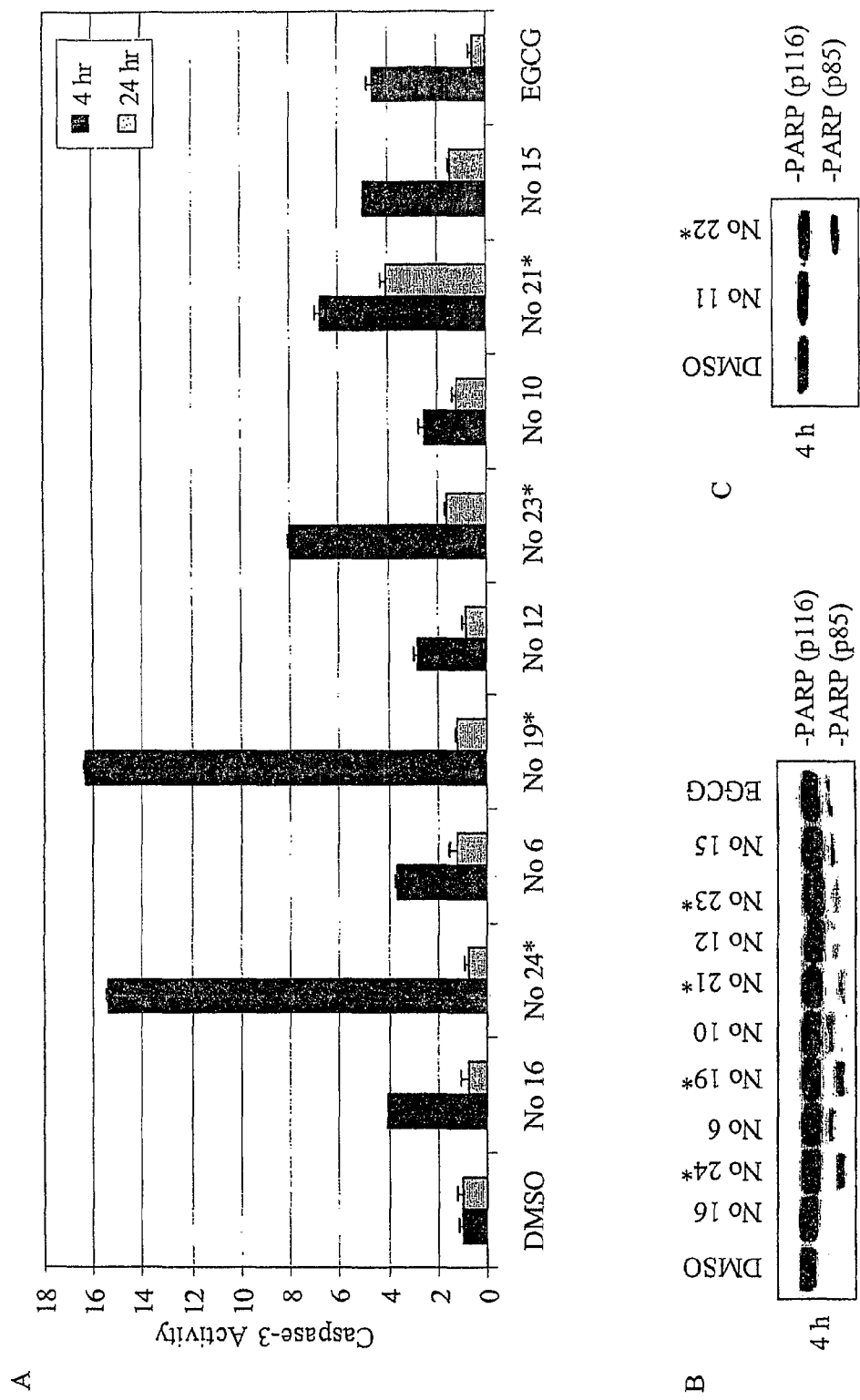
FIG. 17 shows the activation of caspase-3 when Jurkat T cells were treated with the solvent (DMSO), and 25 µM of the compounds in FIG. 13.

Trypan blue analysis confirmed the occurrence of cell death and the characteristic apoptotic morphological changes induced after treatment with mainly protected analogs (FIG. 16). The protected analogs again appeared more stable at 24 h (cell death greater than 50% in all) than the unprotected analogs. Caspase-3 activity confirms that apoptosis occurred after 4 h incubation with the protected compounds; caspase-3 activity was increased up to 16-fold compared to the control (FIG. 17). Western blot analysis for PARP cleavage further showed appearance after 4 h treatment with the protected analogs such as 19*, 24*, and 22*. Most importantly, the peracetate-protected (−)-EGCG analog, 19*, preferentially induced apoptosis in Jurkat T cells while the non-transformed YT cells remained less unaffected (FIG. 18), suggesting a potential for the protected analogs to be developed into novel anti-cancer agents.

In summary, epidemiological studies have suggested the anti-cancer benefits of green tea consumption. The proteasome has been indicated in the pathological state of cancer (Ciechanover A: *Embo J* 17: 7151-7160, 1998.), and green tea polyphenols as inhibitors of the proteasome may be a viable treatment for some cancers. Our current study further suggest that synthetic green tea polyphenols containing peracetate-protected —OH groups are potent proteasome inhibitors and that further examination of these compounds may elucidate additional benefits from this form of therapeutics.

This invention provides a variety of derivatives of (−)-EGCG that is at least as potent as (−)-EGCG. The carboxylate protected forms of (−)-EGCG and its derivatives are found to be more stable than the unprotected forms, which can be used as proteasome inhibitors to reduce tumor cell growth. Further, from the structures of 1, 2, 3, 4, 19*, 21*, 22* and 23* it can be seen that some of the hydroxyl groups of the gallate ring of (−)-EGCG may not be important to the potency.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

The invention claimed is:

1. A compound for inhibiting proteasome having the formula:

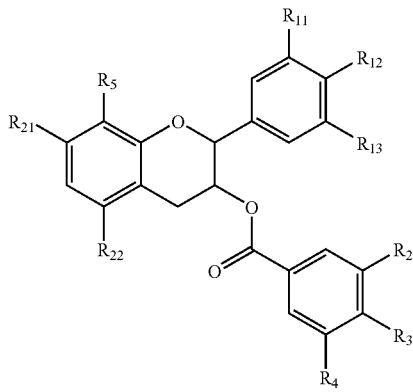

wherein $R_5$ is selected from the group consisting of —H, $C_1$-$C_{10}$ alkyl, $C_2$-$C_{10}$ alkenyl, $C_2$-$C_{10}$ alkynyl, $C_3$-$C_7$ cycloalkyl, phenyl, benzyl and $C_3$-$C_7$ cycloalkenyl, wherein each of the $C_1$-$C_{10}$ alkyl, $C_2$-$C_{10}$ alkenyl, $C_2$-$C_{10}$ alkynyl, $C_3$-$C_7$ cycloalkyl, phenyl, benzyl and $C_3$-$C_7$ cycloalkenyl can be substituted with any combination of one to six halogen atoms; and wherein the formula satisfies one of the following conditions (1) to (6):
(1) each of $R_{11}$, $R_2$, and $R_4$ is —H, and each of $R_{12}$, $R_{13}$, $R_{21}$, $R_{22}$, and $R_3$ is a benzoate group;
(2) each of $R_{11}$, $R_{13}$, $R_2$, and $R_4$ is —H, and each of $R_{12}$, $R_{21}$, $R_{22}$, and $R_3$ is an acetate group;
(3) each of $R_{11}$, $R_{13}$, $R_2$, and $R_4$ is —H, and each of $R_{12}$, $R_{21}$, $R_{22}$, and $R_3$ is a benzoate group;
(4) each of $R_{11}$ and $R_{13}$ is —H, and each of $R_{12}$, $R_{21}$, $R_{22}$, $R_2$, $R_3$, and $R_4$ is an acetate group;
(5) wherein $R_5$ is —H, each of $R_{11}$, $R_{12}$, $R_{13}$, $R_{21}$, and $R_{22}$ is an acetate group, $R_2$ is an acetate group, and each of $R_3$ and $R_4$ is —H; or
(6) wherein $R_5$ is —H, each of $R_{11}$, $R_{12}$, $R_{13}$, $R_{21}$, and $R_{22}$ is an acetate group, each of $R_2$ and $R_4$ is an acetate group, and $R_3$ is —H.

2. The compound of claim 1, wherein each of $R_{11}$, $R_2$, and $R_4$ is —H, and each of $R_{12}$, $R_{13}$, $R_{21}$, $R_{22}$, and $R_3$ is a benzoate group.

3. The compound of claim 1, wherein each of $R_{11}$, $R_{13}$, $R_2$, and $R_4$ is —H, and each of $R_{12}$, $R_{21}$, $R_{22}$, and $R_3$ is an acetate group.

4. The compound of claim 1, wherein each of $R_{11}$, $R_{13}$, $R_2$, and $R_4$ is —H, and each of $R_{12}$, $R_{21}$, $R_{22}$, and $R_3$ is a benzoate group.

5. The compound of claim 1, wherein each of $R_{11}$ and $R_{13}$ is —H, and each of $R_{12}$, $R_{21}$, $R_{22}$, $R_2$, $R_3$, and $R_4$ is an acetate group.

6. A compound for inhibiting proteasome having the formula:

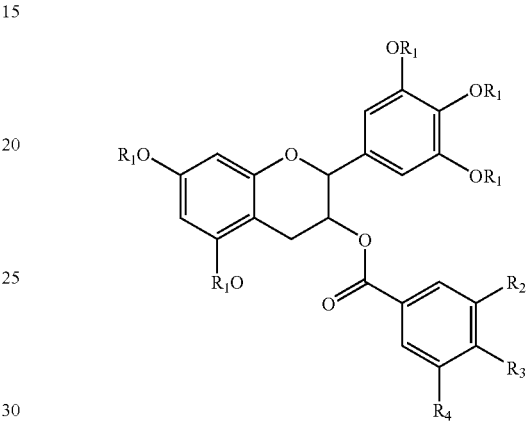

wherein the formula satisfies one of conditions (1) to (4):
(1) $R_1$ is —H, $R_2$ is —OH, and each of $R_3$ and $R_4$ is —H;
(2) $R_1$ is —H, each of $R_2$ and $R_4$ is —OH, and $R_3$ is —H;
(3) $R_1$ is —Ac, $R_2$ is —OAc, and each of $R_3$ and $R_4$ is —H; or
(4) $R_1$ is —Ac, each of $R_2$ and $R_4$ is —OAc, and $R_3$ is —H.

7. The compound of claim 6, wherein $R_2$ is —OH, and each of $R_3$ and $R_4$ is —H.

8. The compound of claim 1, wherein the formula satisfies one of conditions (2), (4), (5) or (6).

9. The compound of claim 1, wherein the formula satisfies condition (2) or condition (4).

10. The compound of claim 6, wherein the formula satisfies condition (3) or condition (4).

* * * * *